US009181582B2

(12) United States Patent
Kurn

(10) Patent No.: US 9,181,582 B2
(45) Date of Patent: *Nov. 10, 2015

(54) COMPOSITIONS FOR AMPLIFICATION OF RNA SEQUENCES USING COMPOSITE PRIMERS

(71) Applicant: NUGEN TECHNOLOGIES, INC., San Carlos, CA (US)

(72) Inventor: Nurith Kurn, Palo Alto, CA (US)

(73) Assignee: NUGEN TECHNOLOGIES, INC., San Carlos, CA (US)

( * ) Notice: Subject to any disclaimer, the term of this patent is extended or adjusted under 35 U.S.C. 154(b) by 76 days.

This patent is subject to a terminal disclaimer.

(21) Appl. No.: 13/922,146

(22) Filed: Jun. 19, 2013

(65) Prior Publication Data

US 2014/0038188 A1 Feb. 6, 2014

Related U.S. Application Data

(63) Continuation of application No. 13/282,732, filed on Oct. 27, 2011, now Pat. No. 8,492,095, which is a continuation of application No. 12/615,958, filed on Nov. 10, 2009, now Pat. No. 8,071,311, which is a continuation of application No. 12/020,434, filed on Jan. 25, 2008, now Pat. No. 7,771,946, which is a continuation of application No. 10/934,890, filed on Sep. 3, 2004, now Pat. No. 7,354,717, which is a continuation of application No. 10/100,321, filed on Mar. 11, 2002, now Pat. No. 6,946,251.

(60) Provisional application No. 60/274,550, filed on Mar. 9, 2001.

(51) Int. Cl.
*C07H 21/04* (2006.01)
*C12Q 1/68* (2006.01)

(52) U.S. Cl.
CPC .................................... *C12Q 1/6853* (2013.01)

(58) Field of Classification Search
USPC ....................................................... 536/24.33
See application file for complete search history.

(56) References Cited

U.S. PATENT DOCUMENTS

| | | | |
|---|---|---|---|
| 3,996,345 A | 12/1976 | Ullman et al. |
| 3,999,345 A | 12/1976 | McKelvey |
| 4,174,384 A | 11/1979 | Ullman et al. |
| 4,261,968 A | 4/1981 | Ullman et al. |
| 4,362,867 A | 12/1982 | Paddock |
| 4,458,066 A | 7/1984 | Caruthers et al. |
| 4,582,788 A | 4/1986 | Erlich |
| 4,683,194 A | 7/1987 | Saiki et al. |
| 4,786,600 A | 11/1988 | Kramer et al. |
| 4,876,187 A | 10/1989 | Duck et al. |
| 4,908,385 A | 3/1990 | Bar-Tana et al. |
| 4,996,143 A | 2/1991 | Heller et al. |
| 5,011,769 A | 4/1991 | Duck et al. |
| 5,043,272 A | 8/1991 | Hartley |
| 5,090,591 A | 2/1992 | Long |
| 5,106,727 A | 4/1992 | Hartley et al. |
| 5,130,238 A | 7/1992 | Malek et al. |
| 5,169,766 A | 12/1992 | Schuster et al. |
| 5,175,243 A | 12/1992 | Ash |
| 5,185,243 A | 2/1993 | Ullman et al. |
| 5,194,370 A | 3/1993 | Berninger et al. |
| 5,262,311 A | 11/1993 | Pardee et al. |
| 5,270,184 A | 12/1993 | Walker et al. |
| 5,328,985 A | 7/1994 | Sano et al. |
| 5,340,716 A | 8/1994 | Ullman et al. |
| 5,399,491 A | 3/1995 | Kacian et al. |
| 5,403,711 A | 4/1995 | Walder et al. |
| 5,409,818 A | 4/1995 | Davey et al. |
| 5,427,911 A | 6/1995 | Ruano |
| 5,427,929 A | 6/1995 | Richards et al. |
| 5,427,930 A | 6/1995 | Birkenmeyer et al. |
| 5,437,990 A | 8/1995 | Burg et al. |

(Continued)

FOREIGN PATENT DOCUMENTS

| | | |
|---|---|---|
| EP | 0050424 A1 | 4/1982 |
| EP | 0084796 B1 | 8/1983 |

(Continued)

OTHER PUBLICATIONS

U.S. Appl. No. 60/255,638, filed Dec. 13, 2000, Kurn.
U.S. Appl. No. 60/381,457, filed May 17, 2003, Kurn.
U.S. Appl. No. 60/533,381, filed Dec. 29, 2003, Kurn et al.
U.S. Appl. No. 13/918,636, filed Jun. 14, 2013, Kurn et al.
U.S. Appl. No. 13/938,059, filed Jul. 9, 2013, Schroeder et al.
U.S. Appl. No. 13/939,025, filed Jul. 10, 2013, Kurn et al.
U.S. Appl. No. 14/030,761, filed Sep. 18, 2013, Kurn et al.
Abravaya et al. Detection of point mutations with a modified ligase chain reaction (GAP-LCR). Nucleic Acids Research. 1995;23(4):675-682.

(Continued)

*Primary Examiner* — Kenneth Horlick
(74) *Attorney, Agent, or Firm* — Wilson Sonsini Goodrich & Rosati, PC

(57) ABSTRACT

The invention provides methods for isothermal amplification of RNA. The methods are particularly suitable for amplifying a plurality of RNA species in a sample. The methods employ a composite primer, a second primer and strand displacement to generate multiple copies of DNA products comprising sequences complementary to an RNA sequence of interest. In another aspect, the methods employ a single primer (which is a composite primer) and strand displacement to generate multiple copies of DNA products comprising sequences complementary to an RNA sequence of interest. In some embodiments, a transcription step is included to generate multiple copies of sense RNA of an RNA sequence of interest. The methods are useful for preparation of nucleic acid libraries and substrates for analysis of gene expression of cells in biological samples. The invention also provides compositions and kits for practicing the amplification methods, as well as methods which use the amplification products.

15 Claims, 19 Drawing Sheets

(56) References Cited

U.S. PATENT DOCUMENTS

| | | |
|---|---|---|
| 5,455,166 A | 10/1995 | Walker |
| 5,480,784 A | 1/1996 | Kacian et al. |
| 5,491,063 A | 2/1996 | Fisher et al. |
| 5,508,178 A | 4/1996 | Rose et al. |
| 5,510,270 A | 4/1996 | Fodor et al. |
| 5,545,522 A | 8/1996 | Van Gelder et al. |
| 5,554,516 A | 9/1996 | Kacian et al. |
| 5,554,517 A | 9/1996 | Davey et al. |
| 5,556,752 A | 9/1996 | Lockhart et al. |
| 5,556,771 A | 9/1996 | Shen et al. |
| 5,565,322 A | 10/1996 | Heller |
| 5,571,669 A | 11/1996 | Lu et al. |
| 5,578,832 A | 11/1996 | Trulson et al. |
| 5,589,339 A | 12/1996 | Hampson et al. |
| 5,595,891 A | 1/1997 | Rose et al. |
| 5,616,478 A | 4/1997 | Chetverin et al. |
| 5,627,275 A | 5/1997 | Roll |
| 5,641,658 A | 6/1997 | Adams et al. |
| 5,648,211 A | 7/1997 | Fraiser et al. |
| 5,654,142 A | 8/1997 | Kievits et al. |
| 5,660,988 A | 8/1997 | Duck et al. |
| 5,665,539 A | 9/1997 | Sano et al. |
| 5,665,545 A | 9/1997 | Malek et al. |
| 5,665,845 A | 9/1997 | Allman |
| 5,679,512 A | 10/1997 | Laney et al. |
| 5,679,524 A | 10/1997 | Nikiforov et al. |
| 5,683,879 A | 11/1997 | Laney et al. |
| 5,686,272 A | 11/1997 | Marshall et al. |
| 5,688,648 A | 11/1997 | Mathies et al. |
| 5,693,502 A | 12/1997 | Gold et al. |
| 5,700,642 A | 12/1997 | Monforte et al. |
| 5,708,154 A | 1/1998 | Smith et al. |
| 5,709,994 A | 1/1998 | Pease et al. |
| 5,710,028 A | 1/1998 | Eyal et al. |
| 5,712,124 A | 1/1998 | Walker |
| 5,712,127 A | 1/1998 | Malek et al. |
| 5,714,320 A | 2/1998 | Kool |
| 5,716,785 A | 2/1998 | Van Gelder et al. |
| 5,731,146 A | 3/1998 | Duck et al. |
| 5,731,171 A | 3/1998 | Bohlander |
| 5,744,308 A | 4/1998 | Guillou-Bonnici et al. |
| 5,744,312 A | 4/1998 | Mamone et al. |
| 5,747,255 A | 5/1998 | Brenner |
| 5,763,178 A | 6/1998 | Chirikjian et al. |
| 5,766,846 A | 6/1998 | Schlossmacher et al. |
| 5,766,849 A | 6/1998 | McDonough et al. |
| 5,773,601 A | 6/1998 | Agrawal |
| 5,811,238 A | 9/1998 | Stemmer et al. |
| 5,824,517 A | 10/1998 | Cleuziat et al. |
| 5,824,518 A | 10/1998 | Kacian et al. |
| 5,829,547 A | 11/1998 | Fujii et al. |
| 5,830,655 A | 11/1998 | Monforte et al. |
| 5,830,721 A | 11/1998 | Stemmer et al. |
| 5,837,832 A | 11/1998 | Chee et al. |
| 5,846,710 A | 12/1998 | Bajaj |
| 5,849,478 A | 12/1998 | Cashman |
| 5,849,542 A | 12/1998 | Reeve et al. |
| 5,849,547 A | 12/1998 | Cleuziat et al. |
| 5,854,033 A | 12/1998 | Lizardi et al. |
| 5,858,665 A | 1/1999 | Hepp et al. |
| 5,871,697 A | 2/1999 | Rothberg et al. |
| 5,876,976 A | 3/1999 | Richards et al. |
| 5,882,867 A | 3/1999 | Ullman et al. |
| 5,888,779 A | 3/1999 | Kacian et al. |
| 5,888,819 A | 3/1999 | Goelet et al. |
| 5,916,777 A | 6/1999 | Kacian et al. |
| 5,925,517 A | 7/1999 | Tyagi et al. |
| 5,932,449 A | 8/1999 | Emanuel et al. |
| 5,932,450 A | 8/1999 | Dattagupta et al. |
| 5,932,451 A | 8/1999 | Wang et al. |
| 5,958,681 A | 9/1999 | Wetmur et al. |
| 5,962,271 A | 10/1999 | Chenchik et al. |
| 5,962,272 A | 10/1999 | Chenchik et al. |
| 5,965,409 A | 10/1999 | Pardee et al. |
| 5,985,548 A | 11/1999 | Collier et al. |
| 6,004,744 A | 12/1999 | Goelet et al. |
| 6,004,745 A | 12/1999 | Arnold, Jr. et al. |
| 6,013,431 A | 1/2000 | Soderlund et al. |
| 6,027,889 A | 2/2000 | Barany et al. |
| 6,027,923 A | 2/2000 | Wallace |
| 6,030,774 A | 2/2000 | Laney et al. |
| 6,037,152 A | 3/2000 | Richards et al. |
| 6,040,138 A | 3/2000 | Lockhart et al. |
| 6,060,288 A | 5/2000 | Adams et al. |
| 6,083,689 A | 7/2000 | Martinelli et al. |
| 6,087,103 A | 7/2000 | Burmer |
| 6,090,591 A | 7/2000 | Burg et al. |
| 6,096,715 A | 8/2000 | Rossi et al. |
| 6,107,032 A | 8/2000 | Kilger et al. |
| 6,107,061 A | 8/2000 | Johnson |
| 6,124,120 A | 9/2000 | Lizardi |
| 6,132,997 A | 10/2000 | Shannon |
| 6,136,533 A | 10/2000 | Bekkaoui et al. |
| 6,140,086 A | 10/2000 | Fox et al. |
| 6,143,495 A | 11/2000 | Lizardi et al. |
| 6,159,685 A | 12/2000 | Pinkel et al. |
| 6,183,960 B1 | 2/2001 | Lizardi |
| 6,210,884 B1 | 4/2001 | Lizardi |
| 6,218,105 B1 | 4/2001 | Hall et al. |
| 6,218,151 B1 | 4/2001 | Cleuziat et al. |
| 6,251,600 B1 | 6/2001 | Winger et al. |
| 6,251,639 B1 | 6/2001 | Kurn |
| 6,255,060 B1 | 7/2001 | Eberwine et al. |
| 6,270,961 B1 | 8/2001 | Drmanac |
| 6,271,002 B1 | 8/2001 | Linsley et al. |
| 6,280,935 B1 | 8/2001 | Macevicz |
| 6,280,949 B1 | 8/2001 | Lizardi |
| 6,291,166 B1 | 9/2001 | Gerdes et al. |
| 6,291,170 B1 | 9/2001 | Van Gelder et al. |
| 6,300,073 B1 | 10/2001 | Zhao et al. |
| 6,306,365 B1 | 10/2001 | Ruoslahti et al. |
| 6,309,842 B1 | 10/2001 | Dower et al. |
| 6,309,843 B1 | 10/2001 | Timms |
| 6,316,229 B1 | 11/2001 | Lizardi et al. |
| 6,319,714 B1 | 11/2001 | Crameri et al. |
| 6,326,142 B1 | 12/2001 | Royer |
| 6,335,160 B1 | 1/2002 | Patten et al. |
| 6,344,356 B1 | 2/2002 | Stemmer |
| 6,358,712 B1 | 3/2002 | Jarrell et al. |
| 6,365,375 B1 | 4/2002 | Dietmaier et al. |
| 6,376,191 B1 | 4/2002 | Yu et al. |
| 6,410,278 B1 | 6/2002 | Notomi et al. |
| 6,485,944 B1 | 11/2002 | Church et al. |
| 6,617,137 B2 | 9/2003 | Dean et al. |
| 6,642,034 B2 | 11/2003 | Lizardi |
| 6,673,549 B1 | 1/2004 | Furness et al. |
| 6,686,156 B2 | 2/2004 | Kurn |
| 6,692,918 B2 | 2/2004 | Kurn |
| 6,794,138 B1 | 9/2004 | Cao et al. |
| 6,815,164 B2 | 11/2004 | Kurn |
| 6,858,413 B2 | 2/2005 | Kurn |
| 6,927,024 B2 | 8/2005 | Dodge et al. |
| 6,946,251 B2 | 9/2005 | Kurn |
| 6,949,633 B1 | 9/2005 | Monforte et al. |
| 6,951,722 B2 | 10/2005 | Mukai et al. |
| 7,056,671 B2 | 6/2006 | Enoki et al. |
| 7,094,536 B2 | 8/2006 | Kurn |
| 7,176,025 B2 | 2/2007 | Kurn |
| 7,294,461 B2 | 11/2007 | Kurn |
| 7,351,557 B2 | 4/2008 | Kurn |
| 7,354,717 B2 | 4/2008 | Kurn |
| 7,402,386 B2 | 7/2008 | Kurn et al. |
| 7,534,569 B2 | 5/2009 | Chang et al. |
| 7,771,934 B2 | 8/2010 | Kurn |
| 7,824,890 B2 | 11/2010 | Hoser et al. |
| 7,833,716 B2 | 11/2010 | Becker et al. |
| 7,846,666 B2 | 12/2010 | Kurn |
| 7,846,733 B2 | 12/2010 | Kurn |
| 7,939,258 B2 | 5/2011 | Kurn et al. |
| 8,034,568 B2 | 10/2011 | Kurn et al. |
| 8,071,311 B2 | 12/2011 | Kurn et al. |
| 8,334,116 B2 | 12/2012 | Kurn |
| 8,465,950 B2 | 6/2013 | Kurn et al. |
| 8,492,095 B2 | 7/2013 | Kurn |

(56) References Cited

U.S. PATENT DOCUMENTS

| | | |
|---|---|---|
| 8,512,956 B2 | 8/2013 | Kurn |
| 2001/0000077 A1 | 3/2001 | Engelhardt et al. |
| 2001/0034048 A1 | 10/2001 | Kurn |
| 2001/0041334 A1 | 11/2001 | Rashtchian et al. |
| 2002/0028447 A1 | 3/2002 | Li et al. |
| 2002/0058270 A1 | 5/2002 | Kurn |
| 2002/0064837 A1 | 5/2002 | Trinh et al. |
| 2002/0106666 A1 | 8/2002 | Hayashizaki |
| 2002/0115088 A1 | 8/2002 | Kurn |
| 2002/0127575 A1 | 9/2002 | Hoke et al. |
| 2002/0142309 A1 | 10/2002 | Dattagupta |
| 2002/0164628 A1 | 11/2002 | Kurn |
| 2002/0177141 A1 | 11/2002 | Chee et al. |
| 2003/0017591 A1 | 1/2003 | Kurn |
| 2003/0049657 A1 | 3/2003 | Cherry |
| 2003/0073081 A1 | 4/2003 | Mukai et al. |
| 2003/0087251 A1 | 5/2003 | Kurn |
| 2003/0104460 A1 | 6/2003 | Rabbani et al. |
| 2003/0186234 A1 | 10/2003 | Kurn |
| 2003/0204331 A1 | 10/2003 | Whitney et al. |
| 2003/0215926 A1 | 11/2003 | Kurn et al. |
| 2004/0005614 A1 | 1/2004 | Kurn et al. |
| 2004/0023271 A1 | 2/2004 | Kurn et al. |
| 2004/0033499 A1 | 2/2004 | Ilsley |
| 2004/0096853 A1 | 5/2004 | Mayer |
| 2004/0203019 A1 | 10/2004 | Kurn |
| 2004/0203025 A1 | 10/2004 | Kurn |
| 2005/0003441 A1 | 1/2005 | Kurn |
| 2005/0014192 A1 | 1/2005 | Kurn |
| 2005/0019793 A1 | 1/2005 | Kurn et al. |
| 2005/0037351 A1 | 2/2005 | Kanno et al. |
| 2005/0064456 A1 | 3/2005 | Kurn |
| 2005/0079510 A1 | 4/2005 | Berka et al. |
| 2005/0123950 A1 | 6/2005 | Mukai et al. |
| 2005/0130173 A1 | 6/2005 | Leamon et al. |
| 2005/0208538 A1 | 9/2005 | Kurn et al. |
| 2006/0008824 A1 | 1/2006 | Ronaghi et al. |
| 2006/0014182 A1 | 1/2006 | Kurn |
| 2006/0183132 A1 | 8/2006 | Fu et al. |
| 2006/0246434 A1 | 11/2006 | Erlander et al. |
| 2006/0257879 A1 | 11/2006 | Wilson et al. |
| 2006/0269934 A1 | 11/2006 | Woudenberg et al. |
| 2007/0054301 A1 | 3/2007 | Becker et al. |
| 2008/0176311 A1 | 7/2008 | Kurn |
| 2008/0182300 A1 | 7/2008 | Kurn |
| 2009/0036663 A1 | 2/2009 | Kurn |
| 2009/0068709 A1 | 3/2009 | Kurn et al. |
| 2009/0117573 A1 | 5/2009 | Fu et al. |
| 2009/0130721 A1 | 5/2009 | Kurn et al. |
| 2009/0203085 A1 | 8/2009 | Kurn et al. |
| 2009/0203531 A1 | 8/2009 | Kurn et al. |
| 2009/0233804 A1 | 9/2009 | Kurn et al. |
| 2009/0239232 A1 | 9/2009 | Kurn et al. |
| 2009/0275486 A1 | 11/2009 | Kurn et al. |
| 2010/0022403 A1 | 1/2010 | Kurn et al. |
| 2010/0159559 A1 | 6/2010 | Kurn et al. |
| 2010/0167354 A1 | 7/2010 | Kurn et al. |
| 2010/0311066 A1 | 12/2010 | Kurn |
| 2011/0105364 A1 | 5/2011 | Kurn |
| 2011/0189679 A1 | 8/2011 | Kurn et al. |
| 2011/0224105 A1 | 9/2011 | Kurn et al. |
| 2011/0294132 A1 | 12/2011 | Kurn |
| 2012/0028310 A1 | 2/2012 | Kurn et al. |
| 2012/0045797 A1 | 2/2012 | Kurn et al. |
| 2012/0149068 A1 | 6/2012 | Kurn et al. |
| 2012/0190587 A1 | 7/2012 | Kurn et al. |
| 2013/0231253 A1 | 9/2013 | Amorese et al. |
| 2014/0038236 A1 | 2/2014 | Kurn et al. |

FOREIGN PATENT DOCUMENTS

| | | |
|---|---|---|
| EP | 0201184 B1 | 11/1986 |
| EP | 0237362 B1 | 9/1987 |
| EP | 0258017 B1 | 3/1988 |
| EP | 0320308 B1 | 6/1989 |
| EP | 0365627 B1 | 5/1990 |
| EP | 0395398 A2 | 10/1990 |
| EP | 0395398 A3 | 10/1990 |
| EP | 0497272 B1 | 8/1992 |
| EP | 0500224 A2 | 8/1992 |
| EP | 0505012 B1 | 9/1992 |
| EP | 0543612 B1 | 5/1993 |
| EP | 0329822 B1 | 6/1994 |
| EP | 0667393 A2 | 8/1995 |
| EP | 0667393 A3 | 8/1995 |
| EP | 0497271 B1 | 10/1996 |
| EP | 0878553 B1 | 11/1998 |
| EP | 0971039 A2 | 1/2000 |
| EP | 0971039 A3 | 1/2000 |
| EP | 1055736 A1 | 11/2000 |
| EP | 1167524 A1 | 1/2002 |
| EP | 1273737 A2 | 1/2003 |
| EP | 1275737 A2 | 1/2003 |
| EP | 1281757 A1 | 2/2003 |
| EP | 1312682 A1 | 5/2003 |
| JP | 6327500 A | 11/1994 |
| JP | 7023799 A | 1/1995 |
| WO | WO 88/02746 A1 | 4/1988 |
| WO | WO 88/10315 A1 | 12/1988 |
| WO | WO 89/01050 A1 | 2/1989 |
| WO | WO 89/06700 A1 | 7/1989 |
| WO | WO 90/01069 A1 | 2/1990 |
| WO | WO 92/15712 A1 | 9/1992 |
| WO | WO 92/18521 A1 | 10/1992 |
| WO | WO 93/15229 A2 | 8/1993 |
| WO | WO 95/03426 A2 | 2/1995 |
| WO | WO 93/15229 A3 | 3/1995 |
| WO | WO 95/21271 A1 | 8/1995 |
| WO | WO 97/03207 A1 | 1/1997 |
| WO | WO 97/04123 A1 | 2/1997 |
| WO | WO 97/04126 A1 | 2/1997 |
| WO | WO 97/32040 A2 | 9/1997 |
| WO | WO 97/32040 A3 | 10/1997 |
| WO | WO 98/01050 A1 | 1/1998 |
| WO | WO 98/06736 A1 | 2/1998 |
| WO | WO 98/28443 A1 | 7/1998 |
| WO | WO 98/44151 A1 | 10/1998 |
| WO | WO 98/59066 A1 | 12/1998 |
| WO | WO 99/18241 A1 | 4/1999 |
| WO | WO 99/23256 A1 | 5/1999 |
| WO | WO 99/25873 A1 | 5/1999 |
| WO | WO 99/29901 A1 | 6/1999 |
| WO | WO 99/37808 A1 | 7/1999 |
| WO | WO 99/40219 A1 | 8/1999 |
| WO | WO 99/42618 A1 | 8/1999 |
| WO | WO 99/55912 A1 | 11/1999 |
| WO | WO 00/08208 A2 | 2/2000 |
| WO | WO 00/09745 A1 | 2/2000 |
| WO | WO 00/08208 A3 | 5/2000 |
| WO | WO 00/28082 A1 | 5/2000 |
| WO | WO 00/40715 A2 | 7/2000 |
| WO | WO 00/52191 A1 | 9/2000 |
| WO | WO 00/56877 A1 | 9/2000 |
| WO | WO 00/56925 A2 | 9/2000 |
| WO | WO 00/56925 A3 | 9/2000 |
| WO | WO 00/70095 A2 | 11/2000 |
| WO | WO 01/20035 A2 | 3/2001 |
| WO | WO 01/20035 A3 | 3/2001 |
| WO | WO 01/23613 A1 | 4/2001 |
| WO | WO 00/70095 A3 | 8/2001 |
| WO | WO 01/64952 A2 | 9/2001 |
| WO | WO 01/73134 A2 | 10/2001 |
| WO | WO 02/00938 A2 | 1/2002 |
| WO | WO 02/06533 A2 | 1/2002 |
| WO | WO 02/28876 A2 | 4/2002 |
| WO | WO 02/29117 A2 | 4/2002 |
| WO | WO 02/48402 A2 | 6/2002 |
| WO | WO 02/057487 A2 | 7/2002 |
| WO | WO 02/057487 A3 | 7/2002 |
| WO | WO 02/028876 A3 | 8/2002 |
| WO | WO 02/072772 A2 | 9/2002 |
| WO | WO 02/072773 A2 | 9/2002 |
| WO | WO 01/64952 A3 | 12/2002 |

(56) References Cited

FOREIGN PATENT DOCUMENTS

| WO | WO 02/103013 A2 | 12/2002 |
|---|---|---|
| WO | WO 01/73134 A3 | 1/2003 |
| WO | WO 03/012100 A2 | 2/2003 |
| WO | WO 03/012100 A3 | 2/2003 |
| WO | WO 03/012142 A1 | 2/2003 |
| WO | WO 02/103013 A3 | 3/2003 |
| WO | WO 02/06533 A3 | 4/2003 |
| WO | WO 02/000938 A3 | 8/2003 |
| WO | WO 02/029117 A3 | 8/2003 |
| WO | WO 02/072772 A3 | 9/2003 |
| WO | WO 03/078645 A2 | 9/2003 |
| WO | WO 03/078645 A3 | 9/2003 |
| WO | WO 03/083435 A2 | 10/2003 |
| WO | WO 03/083435 A3 | 10/2003 |
| WO | WO 2004/011665 A2 | 2/2004 |
| WO | WO 02/48402 A3 | 4/2004 |
| WO | WO 2004/069849 A2 | 8/2004 |
| WO | WO 2004/092418 A2 | 10/2004 |
| WO | WO 2004/092418 A3 | 12/2004 |
| WO | WO 2004/069849 A3 | 3/2005 |
| WO | WO 2004/011665 A3 | 7/2005 |
| WO | WO 2005/065321 A2 | 7/2005 |
| WO | WO 2006/138257 A2 | 12/2006 |
| WO | WO 2007/030759 A2 | 3/2007 |
| WO | WO 2004/069849 A3 | 4/2007 |
| WO | WO 2007/041201 A2 | 4/2007 |
| WO | WO 2007/030759 A3 | 6/2007 |
| WO | WO 2007/041201 A3 | 11/2007 |
| WO | WO 2007/136717 A1 | 11/2007 |
| WO | WO 2008/005459 A2 | 1/2008 |
| WO | WO 2008/005459 A3 | 2/2008 |
| WO | WO 2006/138257 A3 | 12/2008 |
| WO | WO 2012/103154 A1 | 8/2012 |
| WO | WO 2013/059746 A1 | 4/2013 |

OTHER PUBLICATIONS

Adessi et al. Solid phase DNA amplification: characterisation of primer attachment and amplification mechanisms. Nucleic Acids Research. 2000;28(20):E87.

Agrawal et al. Site Specific Functionalization of Oligonucleotides for Attaching Two Different Reporter Groups. Nucleic Acids Research. 1990;18(18):5419-5423.

Akhras et al. Connector inversion probe technology: a powerful one-primer multiplex DNA amplification system for numerous scientific applications. PLoS ONE. 2007;2(9):e915.

Arashi-Heese et al. XcmI site-containing vector for direct cloning and in vitro transcription of PCR product. Molecular Biotechnology. 1999;12(3):281-3.

Ausubel et al. (eds.) Current Protocols in Molecular Biology. John Wiley & Sons, Inc.; 1995:iii-xii (Table of Contents Only.).

Baner et al. Parallel gene analysis with allele-specific padlock probes and tag microarrays. Nucleic Acids Research. 2003;31(17):e103.

Barbas III et al. In Vitro Evolution of a Neutralizing Human Antibody to Human Immunodeficiency Virus Type I to Enhance Affinity and Broaden Strain Cross-Reactivity. Proc. Natl. Acad. Sci. USA. 1994;91:3809-3813.

Barker et al. Increased DNA microarray hybridization specificity using sscDNA targets. BMC Genomics. 2005;6(1):57.

Barth et al. Combining Phage Display and Screening of cDNA Expression Libraries: A New Approach for Identifying the Target Antigen of an scFv Preselected by Phage Display. Journal of Molecular Biology. 2000;301:751-757.

Beaucage et al. Deoxynucleoside Phosphoramidites—A New Class of Key Intermediates for Deoxypolynucleotide Synthesis. Tetrahedron Letters. 1981;22(20):1859-1862.

Beggs, et al. Characterization of Mycobacterium tuberculosis complex direct repeat sequence for use in cycling probe reaction. J Clin Microbiol. Dec. 1996;34(12):2985-9.

Bekkaoui et al. Rapid detection of the mecA gene in methicillin resistant staphylococci using a colorimetric cycling probe technology. Diagnostic Microbiology and Infectious Disease. 1999;34(2):83-90.

Ben-Artzi, et al. Double-stranded RNA-dependent RNase activity associated with human immunodeficiency virus type 1 reverse transcriptase. Proc Natl Acad Sci U S A. Feb. 1, 1992;89(3):927-31.

Bing, et al. Bridge Amplification: A Solid Phase PCR System for the Amplification and Detection of Allelic Differences in Single Copy Genes. Genetic Identity Conference Proceedings. 1996. Available at http://www.promega.com/geneticidproc/ussymp7proc/0726.html. Accessed Dec. 22, 2009.

Blanchard et al. High-density oligonucleotide arrays. Biosensors & Bioelectronics. 1996;11(6/7):687-690.

Brenner et al. Gene expression analysis by massively parallel signature sequencing (MPSS) on microbead arrays. Nature Biotechnology. 2000;18(6):630-634.

Brown et al. Chemical Synthesis and Cloning of a Tyrosine tRNA Gene. Methods in Enzymology. 1979;68:109-151.

Brown, T.A. Ed. Molecular Biology, LabFax. Bios Scientific Publishers. Academic Press. 1991; pp. 147-148.

Caruthers et al. Chemical synthesis of deoxyoligonucleotides by the phosphoramidite method. Methods in Enzymology. 1987;154:287-313.

Chetverin et al. On the nature of spontaneous RNA synthesis by Q beta replicase. Journal of Molecular Biology. 1991;222(1):3-9.

Church. Genomes for ALL. Scientific American. 2006;294(1):46-54.

Coco et al. DNA Shuffling Method for Generating Highly Recombined Genes and Evolved Enzymes. Nature Biotechnology. 2001;19:354-359.

Cohen et al. Construction of biologically functional bacterial plasmids in vitro. Proc. Natl. Acad. Sci. USA. 1973;70(11):3240-4.

Coljee et al. Seamless Gene Engineering Using RNA- and DNA-Overhang Cloning. Nature Biotechnology. 2000;18:789-791.

Crameri et al. Molecular Evolution of an Arsenate Detoxification Pathway by DNA Shuffling. Nature Biotechnology. 1997;15:436-438.

Dafforn et al. Linear mRNA amplification from as little as 5 ng total RNA for global gene expression analysis. Biotechniques. 2004;37(5):854-857.

Dahl et al. Multigene amplification and massively parallel sequencing for cancer mutation discovery. Proc. Natl. Acad. Sci. USA. 2007;104(22):9387-9392.

Daigo et al. Degenerate Oligonucleotide Primed-Polymerase Chain Reaction-Based Array Comparative Genomic Hybridization for Extensive Amplicon Profiling of Breast Cancers. American Journal of Pathology. 2001;158(5):1623-1631.

Database WPI, Section Ch, Week 199507, Derwent Publications Ltd., London, GB; Class B04, AN 1995-047919, XP002276586 & JP 06 327500 A (Toyobo KK), Nov. 29, 1994. (Abstract Only). 1 page total.

Dean et al. Comprehensive Human Genome Amplification Using Multiple Displacement Amplification. Proc. Natl. Acad. Sci. USA. 2002;99(8):5261-5266.

Derisi et al. Use of cDNA microarray to analyse gene expression patterns in human cancer. Nature Genetics. 1996;14:457-460.

Dietmaier et al. Multiple Mutation Analyses in Single Tumor Cells with Improved Whole Genome Amplification. American Journal of Pathology. 1999;154(1):83-95.

Dressman et al. Transforming single DNA molecules into fluorescent magnetic particles for detection and enumeration of genetic variations. Proc. Natl. Acad. Sci. USA. 2003;100(15):8817-8822.

European Search Report (Supplementary partial) mailed Dec. 22, 2005 for European Patent Application No. 02731119.0.

European search report dated Mar. 13, 2006 for Application No. 02731119.

European search report dated Sep. 17, 2009 for Application No. 04002084.4.

European search report dated Nov. 11, 2008 for Application No. 3718172.4.

European search report dated Nov. 13, 2006 for Application No. 03717952.

European Search Report mailed on May 13, 2004 for patent application No. 02721342.0-2402.

Fan et al. Highly parallel genomic assays. Nature Reviews Genetics. 2006;7(8):632-644.

(56) References Cited

OTHER PUBLICATIONS

Flanagan et al. A Cytosine Analog That Confers Enhanced Potency to Antisense Oligonucleotides. Proc. Natl. Acad. Sci. USA. 1999;96(7):3513-3518.
Fodor et al. Light-Directed, spatially addressable parallel chemical synthesis. Science. 1991;251:767-773.
Freier et al. Improved Free-Energy Parameters for Predictions of RNA Duplex Stability. Proc. Natl. Acad. Sci. USA. 1986;83:9373-9377.
Freshney. Ed. Animal Cell Culture. IRL Press: Oxford; 1987: vii-xii (Table of Contents Only.).
Fu et al. Sequencing Double-Stranded DNA by Strand Displacement. Nucleic Acids Research. 1997;25(3):677-679.
Gait. Oligonucleotide Synthesis: A Practical Approach. ed. IRL Press: Oxford; 1984:vii-xii (Table of Contents).
Gasparini et al. Scanning the First Part of the Neurofibromatosis Type 1 Gene by RNA-SSCP: Identification of Three Novel Mutations and of Two New Polymorphisms. Human Genetics. 1996;97:492-495.
Ghadessy et al. Directed evolution of polymerase function by compartmentalized self-replication. Proc. Natl. Acad. Sci. USA. 2001;98(8):4552-4557.
GO. Protein Structures and Split Genes. Advances in Biophysics. 1985;19:91-131.
Goodchild. Conjugates of Oligonucleotides and Modified Oligonucleotides: A Review of Their Synthesis and Properties. Bioconjugate Chemistry. 1990;1(3):165-187.
Guatelli et al. Isothermal, In Vitro Amplification of Nucleic Acids by a Multienzyme Reaction Modeled After Retroviral Replication. Proc. Natl. Acad. Sci. USA. 1990;87:1874-1878.
Gubler et al. A simple and very efficient method for generating cDNA libraries. Gene. 1983;25:263-269.
Gulick et al. Forced Evolution of Glutathione S-Transferase to Create a More Efficient Drug Detoxication Enzyme. Proc. Natl. Acad. Sci. USA. 1995;92:8140-8144.
Habermann et al. Clostridial Neurotoxins: Handling and Action at the Cellular and Molecular Level. Current Topics in Microbiology and Immunology. 1986;129:93-179.
Hatch, et al. Rolling circle amplification of DNA immobilized on solid surfaces and its application to multiplex mutation detection. Genet Anal. Apr. 1999;15(2):35-40.
Heim et al. Engineering Green Fluorescent Protein for Improved Brightness, Longer Wavelengths and Fluorescence Resonance Energy Transfer. Current Biology. 1996;6:178-182.
Hendrickson et al. High sensitivity multianalyte immunoassay using covalent DNA-labeled antibodies and polymerase chain reaction. Nucleic Acids Research. 1995;23: 522-529.
Hottiger, et al. Strand displacement activity of the human immunodeficiency virus type 1 reverse transcriptase heterodimer and its individual subunits. J Biol Chem. Jan. 14, 1994;269(2):986-91.
Huber, et al. Processing of the primer for plus strand DNA synthesis by human immunodeficiency virus 1 reverse transcriptase. J Biol Chem. Jun. 25, 1990;265(18):10565-73.
Hutchison et al. Cell-free cloning using phi29 DNA polymerase. Proc. Natl. Acad. Sci. USA. 2005;102(48):17332-17336.
Innis et al. PCR Protocols: A Guide to Methods and Applications. Eds. Academic Press. 1990:v-x (Table of Contents).
Inoue, et al. Synthesis and hybridization studies on two complementary nona(2'-O-methyl)ribonucleotides. Nucleic Acids Res. Aug. 11, 1987;15(15):6131-48.
International search report dated Feb. 3, 2003 for PCT Application No. US2001/047775.
International search report dated Mar. 9, 2007 for PCT Application No. US2006/035154.
International search report dated Mar. 18, 2003 for PCT Application No. US01/20660.
International search report dated Jun. 23, 2003 for PCT Application No. US02/07306.
International search report dated Jul. 3, 2001 for PCT Application No. US00/25104.
International search report dated Sep. 28, 2009 for PCT Application No. US2009/033964.
International search report dated Oct. 20, 2009 for PCT Application No. US2009/037870.
International search report dated Nov. 20, 2009 for PCT Application No. US2009/33936.
International Search Report mailed Aug. 8, 2003 for PCT Application No. PCT/US02/07377.
International Search Report mailed on Jan. 8, 2004, for PCT patent application No. PCT/US03/07425 filed on Mar. 11, 2003.
International Search Report mailed on Oct. 15, 2004 for PCT Application No. PCT/US2004/012779 filed on Apr. 14, 2004.
International Search Report mailed on Oct. 30, 2003, for PCT patent application No. PCT/US03/10148 filed on Mar. 31, 2003.
Joyce. Directed Molecular Evolution. Scientific American. 1992;267(6):90-97.
Kass et al. Inter-alu polymerase chain reaction: advancements and applications. Analytical Biochemistry. 1955;228(2):185-193.
Khrapko et al. A method for DNA sequencing by hybridization with oligonucleotide matrix. DNA Sequence. 1991;1:375-388.
Kikuchi et al. An Effective Family Shuffling Method Using Single-Stranded DNA. Gene. 2000;243:133-137.
Kikuchi et al. Novel Family Shuffling Methods for the in vitro Evolution of Enzymes. Gene. 1999;236:159-167.
Kojima et al. PCR amplification from single DNA molecules on magnetic beads in emulsion: application for high-throughput screening of transcription factor targets. Nucleic Acids Research. 2005;33(17):e150.
Kolkman et al. Directed Evolution of Proteins by Exon Shuffling. Nature Biotechology. 2001;19:423-428.
Kricka. Nonisotopic DNA Probe Techniques. Academic Press. 1992. (Table of Contents only).
Kumar et al. The First Analogues of LNA (Locked Nucleic Acids): Phosphorothioate LNA and 2'-Thio-LNA. Bioorganic & Medicincal Chemistry Letters. 1998;8:2219-2222.
Kurn et al. Novel isothermal, linear nucleic acid amplification systems for highly multiplexed applications. Clinical Chemistry. 2005;51(10):1973-1981.
Kurtzman et al. Advances in Directed Protein Evolution by Recursive Genetic Recombination: Applications to Therapeutic Proteins. Current Opinion in Biotechnology. 2001;12:361-370.
Kwoh et al. Transcription-Based Amplification System and Detection of Amplified Human Immunodeficiency Virus Type 1 with a Bead-Based Sandwich Hybridization Format. Proc. Natl. Acad. Sci. USA. 1989;86:1173-1177.
Li et al. Amplification and analysis of DNA sequences in single human sperm and diploid cells. Nature. 1988;335(6189):414-417.
Lishanski et al. Branch Migration Inhibition in PCR-Amplified DNA: Homogeneous Mutation Detection. Nucleic Acids Research. 2000;28(9):E42, pp. i-vu.
Lizardi et al. Mutation detection and single-molecule counting using isothermal rolling-circle amplification. Nature Genetics. 1998;19(3):225-232.
Lockhart et al. Expression monitoring by hybridization to high-density oligonucleotide arrays. Nature Biotechnology. 1996;14:1675-1680.
MacMillan et al. Synthesis of Functionally Tethered Oligodeoxynucleotides by the Convertible Nucleoside Approach. The Journal of Organic Chemistry. 1990;55:5931-5933.
Makos et al. Oligonucleotide Hybridisations on Glass Supports: A Novel Linker for Oligonucleotide Synthesis and Hybridisation Properties of Oligonucleotides Synthesised in situ. Nucleic Acids Research. 1992;20(7):1679-1684.
Marcy et al. Nanoliter reactors improve multiple displacement amplification of genomes from single cells. PLoS Genetics. 2007;3(9):1702-1708.
Marshall et al. DNA chips: An array of possibilities. Nature Biotechnology. 1998;16:27-31.
Maskos et al. Oligonucleotide hybridisations on glass supports: a novel linker for oligonucleotide synthesis and hybridisation properties of oligonucleotides synthesised in situ. Nucleic Acids Research. 1992;20(7):1679-1684.

(56) References Cited

OTHER PUBLICATIONS

Matson et al. Biopolymer synthesis on polypropylene supports: Oligonucleotide arrays. Analytical Biochemistry. 1995;224(1):110-116.
Medical Dictionary, online, definition of RNase I, pp. 1-3, retrieved 2009, from: http://www.mondofacto.com/facts/dictionary?Escherichia+coli+RNase+I.
Mitra et al. In situ localized amplification and contact replication of many individual DNA molecules. Nucleic Acids Research. 1999;27(24):e34.
Miyachi, et al. Application of chimeric RNA—DNA oligonucleotides to the detection of pathogenic microorganisms using surface plasmon resonance. Analytica Chimica Acta. 2000; 407(1):1-10.
Mullis et al. PCR: Polymerase Chain Reaction. eds. Birkhauser: Boston; 1994:xv-xvii (Table of Contents).
Mullis et al. Specific Enzymatic Amplification of DNA in Vitro: the Polymerase Chain Reaction. Cold Spring Harbor Symposia on Quantitative Biology. 1986;51:263-273.
Mullis et al. Specific synthesis of DNA in vitro via a polymerase-catalyzed chain reaction. Methods in Enzymology. 1987;155:335-350.
Nakano et al. Single-molecule PCR using water-in-oil emulsion. Journal of Biotechnology. 2003;102(2):117-24.
Narang et al. Improved Phosphotriester Method for the Synthesis of Gene Fragments. Methods of Enzymology. 1979;68:90-99.
New England Biolab Polymerases. Polymerases from Neb. 2008;p. 1-2. Available at http://www.neb.com/nebecomm/tech_reference/polymerases/polymerases_from_neb.as p. Accessed Jun. 30, 2008.
Nugen, Inc. Ovation Biotin RNA Amplification and Labeling System User Guide. Catalog #2300-12. Published 2004.
Nugen, Inc. Technical Report #1. The Ovation Biotin System Validation for Use with Affymetrix GeneChip Arrays. Published 2004.
Okayama et al. High Efficiency Cloning of Full-Length cDNA. Molecular and Cell Biology. 1982;2:161-170.
Orita et al. Detection of Polymorphisms of Human DNA by Gel Electrophoresis as Single-Strand Conformation Polymorphisms. Proc. Natl. Acad. Sci. USA. 1989;86(8):2766-2770.
Orita et al. Rapid and sensitive detection of point mutations and DNA polymorphisms using the polymerase chain reaction. Genomics. 1989;5(4):874-879.
Patel et al. Formation of chimeric DNA primer extension products by template switching onto an annealed downstream oligonucleotide. Proc. Natl. Acad. Sci. USA. 1996;93:2969-2974.
Pease et al. Light-generated oligonucleotide arrays for rapid DNA sequence analysis. Proc. Natl. Acad. Sci. USA Biochemistry. 1994;91:5022-5026.
Pieles et al. Preparation of a Novel Psoralen Containing Deoxyadenosine Building Block for the Facile Solid Phase Synthesis of Psoralen-Modified Oligonucleotides for a Sequence Specific Crosslink to a Given Target Sequence. Nucleic Acids Research. 1989;17(22):8967-8978.
Pluckthun et al. In Vitro Selection and Evolution of Proteins. Advances in Protein Chemistry. 2001;55:367-403.
Ramsay. DNA chips: State-of-the art. Nature Biotechnology. 1998;16:40-44.
Roget et al. Synthesis and Use of Labelled Nucleoside Phosphoramidite Building Blocks Bearing a Reporter Group: Biotinyl, Dinitrophenyl, Pyrenyl and Dansyl. Nucleic Acids Research. 1989;17:7643-7651.
Saiki et al. Primer-directed enzymatic amplification of DNA with a thermostable DNA polymerase. Science. 1988;239:487-491.
Sambrook et al. (eds.), Molecular Cloning a Laboratory Manual, 1989, Second Edition, Cold Spring Harbor Laboratory Press, Cold Spring Harbor, New York, pp. xi-xxxviii (Table of Contents Only.).
Sano et al. Immuno-PCR: very sensitive antigen detection by means of specific antibody-DNA conjugates. Science. 1992;258:120-122.
Sarkar et al. Screening for Mutations by RNA Single-Strand Conformation Polymorphism (rSSCP): Comparison with DNA-SSCP. Nucleic Acids Research. 1992;20(4):871-878.
Sasaki et al. Transcriptional sequencing: A method for DNA sequencing using RNA polymerase. Biochemistry. 1998;95:3455-3460.
Scaringe et al. Novel RNA synthesis method using 5'-0-silyl-2'-0-orthoester protecting groups. Journal of American Chemical Society. 1998;120:11820-11821.
Scaringe. Advanced 5'-SilyI-2'-Orthoester Approach to RNA Oligonucleotide Synthesis. Methods Enzymology. 2000;317:3-18.
Schena et al. Parallel Human Genome Analysis: Microarray-Based Expression Monitoring of 1000 Genes. Proc. Natl. Acad. Sci. USA. 1996;93:10614-10619.
Schena et al. Quantitative monitoring of gene expression patterns with a complementary DNA microarray. Science. 1995;270:467-470.
Schmidt-Dannert. Directed Evolution of Single Proteins, Metabolic Pathways, and Viruses. Biochemistry. 2001;40(44):13125-13136.
Schweitzer et al. Immunoassays with rolling circle DNA amplification: a versatile platform for ultrasensitive antigen detection. Proc. Natl. Acad. Sci. USA. 2000;97(18):10113-10119.
Scott et al. Production of Cyclic Peptides and Proteins in vivo. Proc. Natl. Acad. Sci. USA. 1999;96(24):13638-13643.
Shalon et al. A DNA microarray system for analyzing complex DNA samples using two-color fluorescent probe hybridization. Genome Research. 1996;6:639-645.
Shendure et al. Accurate multiplex polony sequencing of an evolved bacterial genome. Science. 2005;309(5741):1728-32.
Stemmer. DNA Shuffling by Random Fragmentation and Reassembly: In Vitro Recombination for Molecular Evolution. Proc. Natl. Acad. Sci. USA. 1994;91:10747-10751.
Stemmer. Rapid Evolution of a Protein In Vitro by DNA Shuffling. Nature. 1994;370:389-391.
Stoecklein et al. SCOMP Is Superior to Degenerated Oligonucleotide Primed Polymerase Chain Reaction for Global Amplification of Minute Amounts of DNA From Microdissected Archival Tissue Samples. American Journal of Pathology. 2002;161(1):43-51.
Stratagene Catalog. 1988; p. 39. Gene Characterization Kits. Table of Contents.
Stump et al. The Use of Modified Primers to Eliminate Cycle Sequencing Artifacts. Nucleic Acids Research. 1999;27(23):4642-4648.
Suzuki, et al. Detection of ras Gene Mutations in Human Lung Cancers by Single Strand Conformation Polymorphism Analysis of Polymerase Chain Reaction Products. Oncogene. 1990;5(7):1037-1043.
Tesler et al. Synthesis and Characterization of DNA Oligomers and Duplexes Containing Covalently attached Molecular Labels: Comparison of Biotin, Fluorescein, and Pyrene Labels by Thermodynamic and Optical Spectroscopic Measurements. Journal of the American Chemical Society. 1989;111:6966-6976.
Tijessen. Hybridization with Nucleic Acid Probes. Elsevier Science Publishers. 1993. (Table of Contents).
Tinoco et al. Improved Estimation of Secondary Structure in Ribonucleic Acids. Nature New Biology. 1973;246:40-41.
Traut. Are Proteins Made of Modules? Molecular and Cellular Biochemistry. 1986;70:3-10.
Vogelstein et al. Digital PCR. Proc. Natl. Acad. Sci. USA. 1999;96(16):9236-41.
Volkov et al. Recombination and Chimerageness by in vitro Heteroduplex Formation and in vivo Repair. Nucleic Acids Research. 1999;27(18):e18i-e18vi.
Wadenback et al. Comparison of standard exponential and linear techniques to amplify small cDNA samples for microarrays. BMC Genomics. 2005;6(1):61.
Wahlestedt et al. Potent and nontoxic antisense oligonucleotides containing locked nucleic acids. Proc. Natl. Acad. Sci. USA. 2000;97(10):5633-5638.
Walker et al. Isothermal In Vitro Amplification of DNA by a Restriction Enzyme/DNA Polymerase System. Proc. Natl. Acad. Sci. USA. Applied Biological Sciences. 1992;89:392-396.
Walker et al. Strand displacement amplification—an isothermal, in vitro DNA amplification technique. Nucleic Acids Research 1992;20(7):1691-1696.

(56) References Cited

OTHER PUBLICATIONS

Wang et al. Whole genome amplification and high-throughput allelotyping identified five distinct deletion regions on chromosomes 5 and 6 in microdissected early-stage ovarian tumors. Cancer Research. 2001;61:4169-4174.
Wang et al. High-fidelity mRNA amplification for gene profiling. Nature Biotechnology. 2000;18: 457-459.
Wang, et al. Relative stabilities of triple helices composed of combinations of DNA, RNA and 2'-0-methyl-RNA backbones: chimeric circular oligonucleotides as probes. Nucleic Acids Res. Apr. 11, 1995;23(7):1157-64.
Westin, et al. Anchored multiplex amplification on a microelectronic chip array. Nat Biotechnol. Feb. 2000;18(2):199-204.
Wiltshire et al. Detection of Multiple Allergen-Specific IgEs on Microarrays by Immunoassay with Rolling Circle Amplification. Clinical Chemistry. 2000;46(12):1990-1993.
Wu et al. Detection of Clostridium botulinum neurotoxin type a using immuno-PCR. Letters in Applied Microbiology. 2001;32:321-325.
Wu et al. The Ligation Amplification Reaction (LAR)-Amplification of Specific DNA Sequences Using Sequential Rounds of Template-Dependent Ligation. Genomics. 1989;4:560-569.
You et al. Directed Evolution of Subtilisin E in *Bacillus subtilis* to Enhance Total Activity in Aqueous Dimethylformamide. Protein Engineering. 1994;9(1):77-83.
Zhang et al. Directed Evolution of a Fucosidase From a Galactosidase by DNA Shuffling and Screening. Proc. Natl. Acad. Sci. USA. 1997;94:4504-4509.
Zhang et al. Protein quantification from complex protein mixtures using a proteomics methodology with single-cell resolution. Proc. Natl. Acad. Sci. USA. 2001;98(10):5497-5502.
Zheng et al. Whole Genome Amplification Increases the Efficiency and Validity of Buccal Cell Genotyping in Pediatric Populations. Cancer Epidemiology. 2001;10:697700.
Andras, et al. Strategies for signal amplification in nucleic acid detection. Mol Biotechnol. Sep. 2001;19(1):29-44.
Deiman, et al. Characteristics and applications of nucleic acid sequence-based amplification (NASBA). Mol Biotechnol. Feb. 2002;20(2):163-79.
European search report and search opinion dated Jul. 1, 2011 for Application No. 9711405.2.
Frohman, M.A.. Race: Rapid amplification of cDNA ends. In: PCR Protocols: A Guide to Methods and Applications, Academic Press, NY. 1990;28-38.
Hawkins, et al. Whole genome amplification—applications and advances. Curr Opin Biotechnol. Feb. 2002;13(1):65-7.
International preliminary report on patentability dated Aug. 26, 2010 for PCT Application No. US2009/033936.
International preliminary report on patentability dated Aug. 26, 2010 for PCT Application No. US2009/033964.
Japanese Office Action for Japanese Patent Application No. 2006-513320 dated Jul. 22, 2010 (English Translation of Japanese Office Action).
Notice of allowance dated Sep. 2, 2011 for U.S. Appl. No. 12/615,958.
Office action dated Jan. 19, 2012 for U.S. Appl. No. 12/792,702.
Office action dated Jan. 19, 2012 for U.S. Appl. No. 13/211,996.
Office action dated Apr. 2, 2012 for U.S. Appl. No. 13/103,865.
Office action dated Apr. 6, 2012 for U.S. Appl. No. 13/282,732.
Office action dated May 1, 2012 for U.S. Appl. No. 13/349,927.
Office action dated May 7, 2012 for U.S. Appl. No. 13/206,309.
Office action dated Jul. 23, 2012 for U.S. Appl. No. 13/211,996.
Office action dated Aug. 2, 2011 for U.S. Appl. No. 12/792,702.
Office action dated Aug. 13, 2012 for U.S. Appl. No. 13/349,927.
Office action dated Sep. 14, 2012 for U.S. Appl. No. 13/282,732.
Office action dated Oct. 12, 2010 for U.S. Appl. No. 12/792,702.
Office action dated Oct. 31, 2012 for U.S. Appl. No. 13/103,865.
Office action dated Nov. 2, 2012 for U.S. Appl. No. 13/206,309.
Ohara, et al. One-sided polymerase chain reaction: the amplification of cDNA. Proc Natl Acad Sci U S A. Aug. 1989;86(15):5673-7.
Notice of allowance dated May 30, 2014 for U.S. Appl. No. 13/103,865.
Office action dated Dec. 17, 2013 for U.S. Appl. No. 13/103,865.
Office action dated Feb. 5, 2015 for U.S. Appl. No. 13/918,636.
Notice of allowance dated Jul. 8, 2015 for U.S. Appl. No. 13/918,636.

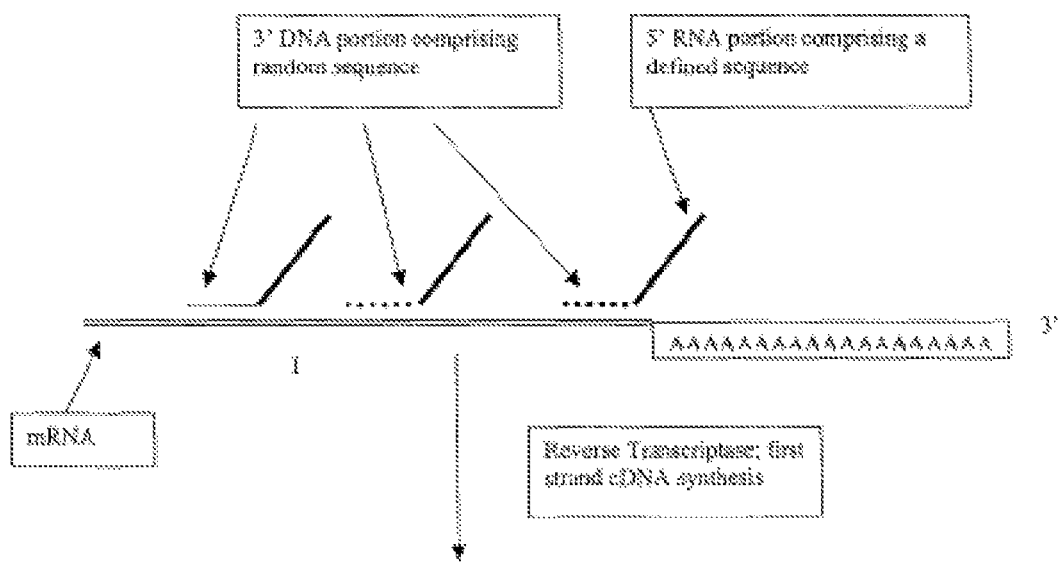
FIG. 6A
FIG. 6B
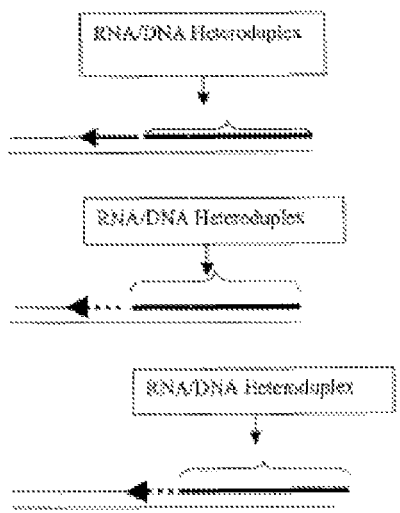
FIG. 6C
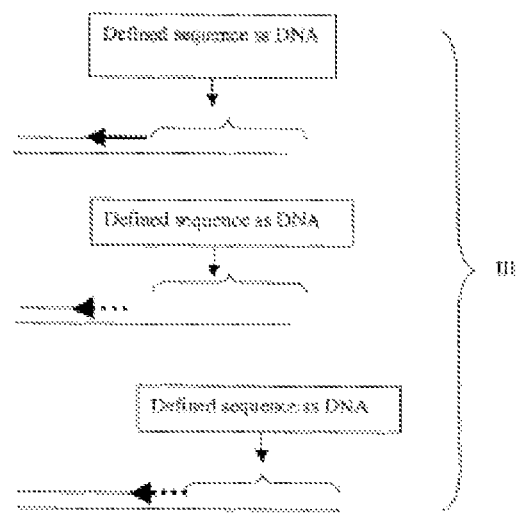

SEQUENCE LISTING

```
<160> NUMBER OF SEQ ID NOS: 25

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 1
gacggaugcg gucuttttt t                                                   21

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (22)..(22)
<223> OTHER INFORMATION: a, c, t, g, unknown or other

<400> SEQUENCE: 2
gacggaugcg gucuttttt tn                                                  22

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (22)..(23)
<223> OTHER INFORMATION: a, c, t, g, unknown or other

<400> SEQUENCE: 3
gacggaugcg gucuttttt tnn                                                 23

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
```

-continued

```
        primer

<400> SEQUENCE: 4
tttcctggta tgacaacgaa                                                20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccagcaagag cacaagagga                                                20

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gatggtacat gacaaggt                                                  18

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gacggatgcg gtcttttttt t                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cccgcaacca cttccgctgt c                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
caaacccgtc acccagatcg t                                              21

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 10
caacacaagg gcgctgacc                                                         19

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (29)..(30)
<223> OTHER INFORMATION: a, c, t, g, unknown or other

<400> SEQUENCE: 11
gacggaugcg gucutttttt ttttttttnn                                             30

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aactaccttc aactccatca                                                        20

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggactcgtca tactcctgc                                                         19

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aggcagcctc tctgctataa gaaa                                                   24

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gcagggcatt gaggttgg                                                          18

<210> SEQ ID NO 16

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
atggcagctg acggtgactt                                              20

<210> SEQ ID NO 17
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
catgggctgg ctgattt                                                 17

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cgcctgatgc tgggacag                                                18

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gttgtacata aaaaatccag gtttgtg                                      27

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gatcctgctc ttaaacgcaa gg                                           22

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tgcctgtctt gtatctctct tcaaac                                       26

<210> SEQ ID NO 22
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: a, c, t, g, unknown or other

<400> SEQUENCE: 22
naaaaaaaaa aaaaaaaaa                                                    19

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: a, c, t, g, unknown or other

<400> SEQUENCE: 23
naaaaaaaaa aaaaaaaaa a                                                  21

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
aaaaaaaaaa aaaaaaaaa                                                    19

<210> SEQ ID NO 25
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: This sequence may be 5 to 50 bases in length

<400> SEQUENCE: 25
tttttttttt tttttttttt tttttttttt tttttttttt tttttttttt                  50
```

COMPOSITIONS FOR AMPLIFICATION OF RNA SEQUENCES USING COMPOSITE PRIMERS

CROSS-REFERENCE TO RELATED APPLICATIONS

This application is a continuation of U.S. Ser. No. 13/282,732, filed Oct. 27, 2011, now U.S. Pat. No. 8,492,095, which is a continuation of U.S. Ser. No. 12/615,958, filed Nov. 10, 2009, now U.S. Pat. No. 8,071,311, which is a continuation of U.S. Ser. No. 12/020,434, filed Jan. 25, 2008, now U.S. Pat. No. 7,771,946, which is a continuation of U.S. Ser. No. 10/934,890, filed Sep. 3, 2004, now U.S. Pat. No. 7,354,717, which is a continuation of U.S. Ser. No. 10/100,321, filed Mar. 11, 2002, now U.S. Pat. No. 6,946,251, which claims the priority benefit of provisional patent application U.S. Ser. No. 60/274,550, filed Mar. 9, 2001, all of which are incorporated herein by reference in their entirety.

SEQUENCE LISTING

The instant application contains a Sequence Listing which has been submitted via EFS-Web and is hereby incorporated by reference in its entirety. Said ASCII copy, created on Sep. 23, 2013 is named 25115704306_SeqList.txt, and is 6.73 kb in size.

TECHNICAL FIELD

The invention relates to the field of polynucleotide amplification. More particularly, the invention provides methods, compositions and kits for amplifying (i.e., making multiple copies) RNA sequences of interest which employ an RNA/DNA composite primer, and, optionally transcription.

BACKGROUND ART

The ability to amplify ribonucleic acid (RNA) is an important aspect of efforts to elucidate biological processes. To date, RNA (generally, mRNA) amplification is most commonly performed using the reverse transcriptase-polymerase chain reaction (RT-PCR) method and variations thereof. These methods are based on replication of RNA by reverse transcriptase to form single stranded DNA complementary to the RNA (cDNA), which is followed by polymerase chain reaction (PCR) amplification to produce multiple copies of double stranded DNA. Although these methods are most commonly used, they have some significant drawbacks: a) the reactions require thermocycling; b) the products are double stranded, thus rendering them less accessible to binding to probes; c) the reactions are prone to contamination with products of prior amplification, thus requiring strict containment of reaction mixtures; and d) the exponential nature of amplification of these methods renders them prone to generate pools of products which do not truly reflect the representation of the various RNA sequences in the input total RNA sample, due to unequal efficiency of amplification of different sequences, and the nature of exponential amplification which is based on replication of amplification products rather than on continued replication of the input target RNAs.

Total cellular mRNA represents gene expression activity at a defined time. Gene expression is affected by cell cycle progression, developmental regulation, response to internal and external stimuli and the like. The profile of expressed genes for any cell type in an organism reflects normal or disease states, response to various stimuli, developmental stages, cell differentiation, and the like.

Various methods for the analysis of gene expression have been developed in recent years. See, for example, U.S. Pat. Nos. 5,744,308; 6,143,495; 5,824,517; 5,829,547; 5,888,779; 5,545,522; 5,716,785; 5,409,818; EP 0971039A2; EP0878553A2. These include quantification of specific mRNAs, and the simultaneous quantification of a large number of mRNAs, as well as the detection and quantification of patterns of expression of known and unknown genes. The analysis of gene expression profiles is currently one of the most powerful tools in the study of cellular differentiation and cellular development, and in the investigation of normal and disease states of various organisms, in particular in human. This analysis is crucial for gene discovery, molecular medicine and drug discovery processes.

Amplification of the total cellular mRNAs prepared from any cell or tissue is generally critical for gene expression profiling. Although analysis of non-amplified mRNA is feasible, a significant amount of starting mRNA would be required. However, the total amount of sample mRNA that is available is frequently limited by the amount of biological sample from which it is derived. Biological samples are often limited in amount and precious. Moreover, the amount of the various mRNA species is not equal; some species are more abundant than others, and these are more likely and easier, to analyze. The ability to amplify mRNA sequences enables the analysis of less abundant, rare mRNA species. The ability to analyze small samples, by means of nucleic acid amplification, is also advantageous for design parameters of large scale screening of effector molecule libraries, for which reduction in sample volume is a major concern both for the ability to perform very large scale screening or ultra high throughput screening, and in view of the limiting amounts of library components.

Therefore, there is a need for improved RNA amplification methods that overcome drawbacks in existing methods. The invention provided herein fulfills this need and provides additional benefits.

All references cited herein, including patent applications and publications, are incorporated by reference in their entirety.

DISCLOSURE OF THE INVENTION

The invention provides methods, compositions, and kits for RNA amplification, as well as applications of the amplification methods.

Accordingly, in one aspect, the invention provides methods of generating multiple copies of a polynucleotide sequence complementary to an RNA sequence of interest, said method comprising the steps of: (a) extending a first primer hybridized to a target RNA with an RNA-dependent DNA polymerase, wherein the first primer is a composite primer comprising an RNA portion and a 3' DNA portion, whereby a complex comprising a first primer extension product and the target RNA is produced; (b) cleaving RNA in the complex of step (b) with an enzyme that cleaves RNA from an RNA/DNA hybrid; (c) extending a second primer hybridized to the first primer extension product with a DNA-dependent DNA polymerase, whereby a second primer extension product is produced to form a complex of first and second primer extension products; (d) cleaving RNA from the composite primer in the complex of first and second primer extension products with an enzyme that cleaves RNA from an RNA/DNA hybrid such that a composite primer hybridizes to the second primer extension product, wherein the composite primer comprises an RNA portion and a 3' DNA portion; (e) extending the composite primer hybridized to the second primer extension product with a DNA-dependent DNA polymerase; whereby said first primer extension product is displaced, and whereby multiple copies of a polynucleotide sequence complementary to the RNA sequence of interest are generated.

In another aspect, the invention provides methods of generating multiple copies of a polynucleotide sequence complementary to an RNA sequence of interest, said method comprising the steps of: (a) extending a second primer hybridized to a first primer extension product with a DNA-dependent DNA polymerase, wherein the first primer extension product comprises an RNA portion at the 5' end, said first primer extension product comprising a sequence complementary to an RNA sequence, whereby a second primer extension product is produced to form a complex of first and second primer extension products; (b) cleaving RNA in the complex of first and second primer extension products with an enzyme that cleaves RNA from an RNA/DNA hybrid such that a composite primer hybridizes to the second primer extension product, wherein the composite primer comprises an RNA portion and a 3' DNA portion; (c) extending the composite primer hybridized to the second primer extension product with a DNA-dependent DNA polymerase; whereby said first primer extension product is displaced, and whereby multiple copies of a polynucleotide sequence complementary to the RNA sequence of interest are generated. In some embodiments of the invention, the first primer extension product is produced by extension of a first primer hybridized to a target RNA with a RNA-dependent DNA polymerase, wherein the first primer is a composite primer comprising an RNA portion and a 3' DNA portion.

In another aspect, the invention provides methods of generating multiple copies of a polynucleotide sequence complementary to an RNA sequence of interest, said method comprising the steps of: (a) cleaving RNA from a complex of first and second primer extension products with an enzyme that cleaves RNA from an RNA/DNA hybrid such that a composite primer hybridizes to the second primer extension product, wherein the composite primer comprises an RNA portion and a 3' DNA portion, wherein the first primer extension product is produced by extension of a first primer hybridized to a target RNA with a RNA-dependent DNA polymerase, wherein the first primer is a composite primer comprising an RNA portion and a 3' DNA portion; (b) hybridizing a composite primer to the second primer extension product and extending the composite primer with a DNA-dependent DNA polymerase; whereby said first primer extension product is displaced, and whereby multiple copies of a polynucleotide sequence complementary to the RNA sequence of interest are generated.

In another aspect, the invention provides methods of generating multiple copies of a polynucleotide sequence complementary to an RNA sequence of interest, said method comprising the step of: extending a composite primer in a complex comprising: (i) a complex of a first and second primer extension products, wherein the first primer extension product is produced by extension of a first primer hybridized to a target RNA with a RNA-dependent DNA polymerase, wherein the first primer is a composite primer comprising an RNA portion and a 3' DNA portion, wherein the second primer extension product is generated by extension of a second primer hybridized to the first primer extension product, and wherein RNA from the complex of first and second primer extension products is cleaved with an enzyme that cleaves RNA from an RNA/DNA hybrid; and (ii) a composite primer, said composite primer comprising an RNA portion and a 3' DNA portion, wherein the composite primer is hybridized to the second primer extension product, and wherein the composite primer may be the same or different from the first primer; whereby said first primer extension product is displaced, and whereby multiple copies of a polynucleotide sequence complementary to the RNA sequence of interest are generated.

In another aspect, the invention provides methods of generating multiple copies of a polynucleotide sequence complementary to an RNA sequence of interest, said method comprising the steps of: (a) extending a composite primer hybridized to a second primer extension product, wherein said primer extension product (i) comprises a complement or a sequence of a first primer extension product generated by extension of a first primer hybridized to template RNA, wherein the first primer is a composite primer comprising an RNA portion and a 3' DNA portion; and (ii) is hybridized to a second primer extension product generated by extension of a second primer hybridized to the first primer extension product, and cleavage of RNA from the first primer with an enzyme that cleaves RNA from an RNA/DNA hybrid; whereby said first primer extension product is displaced, and whereby multiple copies of a polynucleotide sequence complementary to the RNA sequence of interest are generated.

In another aspect, the invention provides methods of generating multiple copies of an RNA sequence of interest, said method comprising the steps of:

hybridizing the displaced first primer extension product from any of the methods of generating multiple copies of a polynucleotide sequence complementary to an RNA sequence of interest described herein, with a polynucleotide comprising a propromoter and a region which is hybridizable to the displaced first primer extension product under conditions which allow transcription to occur by RNA polymerase, such that RNA transcripts are produced comprising sequences complementary to the displaced first primer extension product, whereby multiple copies of the RNA sequence of interest are generated.

In another aspect, the invention provides methods of generating multiple copies of an RNA sequence of interest, said method comprising the steps of: hybridizing a first primer extension product from any of the methods of generating multiple copies of a polynucleotide sequence complementary to an RNA sequence of interest described herein, with a polynucleotide comprising a propromoter and a region which is hybridizable to the displaced first primer extension product under conditions which allow transcription to occur by RNA polymerase, such that RNA transcripts are produced comprising sequences complementary to the displaced first primer extension product, wherein the primer extension product is a displaced primer extension product generated by: (a) extending a first primer hybridized to a target RNA with an RNA-dependent DNA polymerase, wherein the first primer is a composite primer comprising an RNA portion and a 3' DNA portion, whereby a complex comprising a first primer extension product and the target RNA is produced; (b) cleaving RNA in the complex of step (b) with an enzyme that cleaves RNA from an RNA/DNA hybrid; (c) extending a second primer hybridized to the first primer extension product with a DNA-dependent DNA polymerase, whereby a second primer extension product is produced to form a complex of first and second primer extension products; (d) cleaving RNA from the composite primer in the complex of first and second primer extension products with an enzyme that cleaves RNA from an RNA/DNA hybrid such that a composite primer hybridizes to the second primer extension product, wherein the composite primer comprises an RNA portion and a 3' DNA portion; (e) extending said composite primer hybridized to the second primer extension product with a DNA-dependent DNA polymerase, whereby said first primer extension product is displaced; whereby multiple copies of the RNA sequence of interest are generated.

In another aspect, the invention provides methods of generating multiple copies of (amplifying) a polynucleotide sequence complementary to an RNA sequence of interest, said method comprising the steps of: (a) hybridizing a first primer to a target RNA, wherein the first primer is a composite primer comprising an RNA portion and a 3' DNA portion; (b) extending the first primer with an RNA-dependent DNA polymerase, whereby a complex comprising a first primer extension product and the target RNA is produced; (c) cleaving RNA in the complex of step (b) with an agent (such as an enzyme) that cleaves RNA from an RNA/DNA hybrid; (d) hybridizing a second primer to the first primer extension product; (e) extending the second primer with a DNA-dependent DNA polymerase, whereby a second primer extension product is produced to form a complex of first and second primer extension products; (f) cleaving RNA from the composite primer in the complex of first and second primer extension products with an agent (such as an enzyme) that cleaves RNA from an RNA/DNA hybrid such that a composite primer (which may or may not be the same as the first primer) hybridizes to the second primer extension product, wherein said composite primer comprises an RNA portion and a 3' DNA portion; (g) extending said composite primer of step (f) with a DNA-dependent DNA polymerase, whereby said first primer extension product is displaced, and whereby multiple copies of a polynucleotide sequence complementary to the RNA sequence of interest are generated.

In some aspects, the invention provides methods of generating multiple copies of a polynucleotide sequence complementary to an RNA sequence of interest, said method comprising the steps of: combining and reacting: the complex of first and second primer extension products of step (e) described above; a composite primer (which may or may not be the same as the first primer) that is hybridizable to the second primer extension product, wherein said composite primer comprises an RNA portion and a 3' DNA portion; a DNA-dependent DNA polymerase; and an agent (such as an enzyme) that cleaves RNA from an RNA/DNA hybrid; wherein the mixture is incubated under conditions (which include necessary substrates and buffer conditions) that permit primer hybridization, RNA cleavage, and displacement of the first primer extension product from the complex of step (e) described above when its RNA is cleaved and a composite primer binds to the second primer extension product in the complex.

As is clear to one skilled in the art, reference to production of copies of an RNA sequence of interest or copies of a polynucleotide sequence complementary to an RNA sequence of interest refers to products that may contain, comprise or consist of such sequences. As is evident to one skilled in the art, aspects that refer to combining and incubating the resultant mixture also encompasses method embodiments which comprise incubating the various mixtures (in various combinations and/or subcombinations) so that the desired products are formed.

In another aspect, the invention provides methods of generating multiple copies of a polynucleotide sequence complementary to an RNA sequence of interest comprising incubating a reaction mixture, said reaction mixture comprising: (a) a target RNA; (b) a first primer that is hybridizable to the target RNA, wherein the first primer is a composite primer comprising an RNA portion and a 3' DNA portion; (c) a second primer that is hybridizable to an extension product of the first primer; (d) an RNA-dependent DNA polymerase; (e) a DNA-dependent DNA polymerase; (f) an enzyme that cleaves RNA from an RNA/DNA hybrid; wherein the incubation is under conditions that permit primer hybridization, extension from the first primer and the second primer to form a complex comprising first and second primer extension products, RNA cleavage, and displacement of the first primer extension product from the complex when its RNA is cleaved and a composite primer binds to the second primer extension product in the complex and is extended, whereby multiple copies of a polynucleotide sequence complementary to the RNA sequence of interest are generated.

In another aspect, the invention provides methods of generating multiple copies of (amplifying) an RNA sequence of interest, said method comprising the steps of: (a) hybridizing a first primer to a target RNA, wherein the first primer is a composite primer comprising an RNA portion and a 3' DNA portion; (b) extending the first primer with an RNA-dependent DNA polymerase, whereby a complex comprising a first primer extension product and the target RNA is produced; (c) cleaving RNA in the complex of step (b) with an agent (such as an enzyme) that cleaves RNA from an RNA/DNA hybrid; (d) hybridizing a second primer to the first primer extension product; (e) extending the second primer with a DNA-dependent DNA polymerase, whereby a second primer extension product is produced to form a complex of first and second primer extension products; (f) cleaving RNA from the composite primer in the complex of first and second primer extension products with an agent (such as an enzyme) that cleaves RNA from an RNA/DNA hybrid such that a composite primer (which may or may not be the same as the first primer) hybridizes to the second primer extension product, wherein said composite primer comprises an RNA portion and a 3' DNA portion; (g) extending said composite primer of step (f) with a DNA-dependent DNA polymerase whereby said first primer extension product is displaced; (h) hybridizing the displaced first primer extension product with a polynucleotide comprising a propromoter and a region which is hybridizable to the displaced first primer extension product under conditions which allow transcription to occur by RNA polymerase, such that RNA transcripts are produced comprising sequences complementary to the displaced primer extension products, whereby multiple copies of the RNA sequence of interest are generated. In some embodiments, the invention provides methods of generating multiple copies of an RNA sequence of interest, said method comprising the steps of: (a) combining: a first complex, wherein the first complex is the complex of first and second primer extension products of step (e) described above in this paragraph; a composite primer (which may or may not be the same as the first primer) that is hybridizable to the second primer extension product, wherein said composite primer comprises an RNA portion and a 3' DNA portion; a DNA-dependent DNA polymerase; an RNA polymerase; a propromoter polynucleotide comprising a propromoter and a region which hybridizes to a second primer extension product; and an agent (such as an enzyme) that cleaves RNA from an RNA/DNA hybrid; and (b) incubating the mixture of step (a) under conditions (which include necessary substrates and buffer conditions) that permit primer hybridization, RNA cleavage, displacement of the first primer extension product from the first complex when its RNA is cleaved and a composite primer binds to the second primer extension product in the first complex, hybridization of the propromoter polynucleotide to the displaced first primer extension product to form a second complex comprising the displaced primer extension product and the propromoter polynucleotide, and RNA transcription from said second complex.

In another aspect, the invention provides methods of generating multiple copies of an RNA sequence of interest comprising incubating a reaction mixture, said reaction mixture comprising: (a) a target RNA; (b) a first primer that is hybridizable to the target RNA, wherein the first primer is a composite primer comprising an RNA portion and a 3' DNA portion; (c) a second primer that is hybridizable to an extension product of the first primer; (d) an RNA-dependent DNA polymerase; (e) a DNA-dependent DNA polymerase; (f) an RNA polymerase; (g) a propromoter polynucleotide comprising a propromoter and a region which hybridizes to an extension product of the second primer; and (h) an enzyme that cleaves RNA from an RNA/DNA hybrid; wherein the incubation is under conditions that permit primer hybridization, extension from the first primer and the second primer to form a first complex comprising first and second primer extension products, RNA cleavage, displacement of the first primer extension product from the first complex when its RNA is cleaved and a composite primer binds to the second primer extension product in the first complex, hybridization of the propromoter polynucleotide to the displaced first primer extension product to form a second complex comprising the displaced primer extension product and the propromoter polynucleotide, and RNA transcription from said second complex, whereby multiple copies of the RNA sequence of interest are generated.

In still another aspect, the invention provides methods of generating multiple copies of (amplifying) an RNA sequence of interest comprising incubating a reaction mixture, said reaction mixture comprising: (a) a target RNA; (b) a first primer that is hybridizable to the target RNA, wherein the first primer is a composite primer comprising an RNA portion and a 3' DNA portion; (c) a second primer that is hybridizable to an extension product of the first primer; (d) an RNA-dependent DNA polymerase; (e) a DNA-dependent DNA polymerase; and (f) an enzyme that cleaves RNA from an RNA/DNA hybrid; wherein the incubation is under conditions (which include necessary substrates and buffer conditions) that permit primer hybridization, extension from the first primer and the second primer to form a complex comprising first and second primer extension products, RNA cleavage, and displacement of the first primer extension product from the complex when its RNA is cleaved and another first primer binds to the second primer extension product in the complex, whereby multiple copies of a polynucleotide sequence complementary to the RNA sequence of interest are generated.

In another aspect, the invention provides methods of generating multiple copies of (amplifying) an RNA sequence of interest comprising: (a) incubating a reaction mixture, said reaction mixture comprising: (i) a target RNA; and (ii) a first primer that is hybridizable to a target RNA, wherein the first primer is a composite primer comprising an RNA portion and a 3' DNA portion; and (iii) a RNA-dependent DNA polymerase; wherein the incubation is under conditions that permit primer hybridization and formation of a complex comprising a first primer extension product and the target RNA; (b) incubating a reaction mixture, said reaction mixture comprising: (i) the complex comprising a first primer extension product and the target RNA; and (ii) an enzyme capable of cleaving RNA from an RNA/DNA hybrid; wherein the incubation is under conditions that permit cleavage of RNA in the complex comprising a first primer extension product and the target RNA; (c) incubating a reaction mixture, said reaction mixture comprising: (i) the first primer extension product; (ii) a second primer that is hybridizable to the first primer extension product; and (iii) DNA-dependent DNA polymerase; wherein the incubation is under conditions that permit primer hybridization and formation of a complex comprising the first primer extension product and a second primer extension product; (d) incubating a reaction mixture, said reaction mixture comprising: (i) the complex comprising the first primer extension product and a second primer extension product; (ii) an enzyme capable of cleaving RNA from an RNA/DNA hybrid; wherein the incubation is under conditions that permit cleavage of RNA in the complex comprising the first primer extension product and a second primer extension product; (e) incubating a reaction mixture, said reaction mixture comprising: (i) a composite primer, wherein the composite primer comprises a RNA portion and a 3' DNA portion; (ii) the cleaved complex comprising the first primer extension product and a second primer extension product; and (iii) DNA-dependent DNA polymerase; wherein the incubation is under conditions that permit composite primer hybridization, and displacement of the first primer extension product from the complex comprising the first primer extension product and a second primer extension product; whereby multiple copies of a polynucleotide sequence complementary to the RNA sequence of interest are generated.

The reaction mixtures may be combined (thus reducing the number of incubations) in any way, with one or more reaction mixtures above combined. Accordingly, in some embodiments, the reaction mixtures of steps (a) and (b) are the same reaction mixture (four incubations or incubation steps). In other embodiments, the reaction mixtures of steps (d) and (e) are the same reaction mixture (four incubations or incubation steps). In still another embodiment, the reaction mixtures of steps (a) and (b) are the same reaction mixture and the reaction mixtures of steps (d) and (e) are the same reaction mixture (three incubations or incubation steps). In still other embodiments, the reaction mixtures of steps (a)-(c) are the same reaction mixture (three incubations or incubation steps). In still another embodiment, the reaction mixtures of steps (a)-(c) are the same reaction mixture and the reaction mixtures of steps (d) and (e) are the same reaction mixture (two incubations or incubation steps). In other embodiments, the reaction mixtures of steps (a)-(d) are the same reaction mixture (two incubations or incubation steps). In other embodiments, the reaction mixtures of (b) and (c) are the same reaction mixture (four incubations or incubation steps). In other embodiments, the reaction mixtures of (c) and (d) are the same reaction mixture (four incubations or incubation steps). In yet another embodiment, the reaction mixtures of (a)-(e) are the same reaction mixture (one incubation). It is understood that any combination of these incubation steps, and any single incubation step, to the extent that the incubation is performed as part of any of the methods described herein, fall within the scope of the invention.

In another aspect of the invention, the methods of generating multiple copies of (amplifying) an RNA sequence of interest further comprise: (a) incubating a reaction mixture, said reaction mixture comprising: (i) a copy of a polynucleotide sequence complementary to the RNA sequence of interest; (ii) a propromoter polynucleotide comprising a propromoter and a region which hybridizes to the copy of a polynucleotide sequence complementary to the RNA sequence of interest; and RNA polymerase; and wherein the incubation is under conditions that permit hybridization of the propromoter polynucleotide to the copy of a polynucleotide sequence complementary to the RNA sequence of interest to form a second complex comprising the copy of a polynucleotide sequence complementary to the RNA sequence of interest and the propromoter polynucleotide, and RNA transcription from said second complex.

In yet another aspect, the invention provides methods of generating multiple copies of (amplifying) an RNA sequence of interest, said method comprising the steps of: (a) combining: a target RNA; a first primer that is hybridizable to the target RNA, wherein the first primer is a composite primer comprising an RNA portion and a 3' DNA portion; a second primer that is hybridizable to an extension product of the first primer; an RNA-dependent DNA polymerase; a DNA-dependent DNA polymerase; an RNA polymerase; a propromoter polynucleotide comprising a propromoter and a region which hybridizes to an extension product of the second primer; and an agent (such as an enzyme) that cleaves RNA from an RNA/DNA hybrid; and (b) incubating the mixture of step (a) under conditions (which includes necessary substrates and buffer conditions) that permit primer hybridization, extension from the first primer and the second primer to form a first complex comprising first and second primer extension products, RNA cleavage, displacement of the first primer extension product from the first complex when its RNA is cleaved and another first primer binds to the second primer extension product in the first complex, hybridization of the propromoter polynucleotide to the displaced first primer extension product to form a second complex comprising the displaced primer extension product and the propromoter polynucleotide, and RNA transcription from said second complex, whereby multiple copies of the RNA sequence of interest are generated.

In yet another aspect, the invention provides methods of generating multiple copies of (amplifying) a polynucleotide sequence complementary to an RNA sequence of interest, said method comprising the steps of: (a) hybridizing a primer to a target RNA, wherein the primer is a composite primer comprising an RNA portion and a 3' DNA portion; (b) extending the primer with an RNA-dependent DNA polymerase, whereby a complex comprising a primer extension product and the target RNA is produced; (c) cleaving RNA in the complex of step (b) with an agent (such as an enzyme) that cleaves RNA from an RNA/DNA hybrid, such that at least one fragment of the target RNA remains hybridized to the primer extension product; (d) extending the at least one fragment of the target RNA with a DNA-dependent DNA polymerase, whereby a fragment extension product comprising the sequence of interest is produced to form a complex of primer and fragment extension products; (e) cleaving RNA from the composite primer in the complex of primer and fragment extension products with an agent (such as an enzyme) that cleaves RNA from an RNA/DNA hybrid such that a composite primer (which may or may not be the same as the first primer) hybridizes to the fragment extension product and repeats primer extension by strand displacement, wherein said composite primer comprises an RNA portion and a 3' DNA portion; whereby multiple copies of a polynucleotide sequence complementary to the RNA sequence of interest are generated. In some embodiments, the invention provides methods of generating multiple copies of a polynucleotide sequence complementary to an RNA sequence of interest, said method comprising the steps of: (a) combining: the complex of primer and fragment extension product of step (d) described above in this paragraph; a composite primer (which may or may not be the same as the first primer) that is hybridizable to the fragment extension product, wherein said composite primer comprises an RNA portion and a 3' DNA portion; a DNA-dependent DNA polymerase; and an agent (such as an enzyme) that cleaves RNA from an RNA/DNA hybrid; and (b) incubating the mixture of step (a) under conditions (which include necessary substrates and buffer conditions) that permit primer hybridization, RNA cleavage, and displacement of the primer extension product from the complex of step (d) described above in this paragraph when its RNA is cleaved and a composite primer binds to the fragment extension product in the complex.

In yet another aspect, the invention provides methods of generating multiple copies of (amplifying) an RNA sequence of interest, said method comprising the steps of: (a) hybridizing a first primer to a target RNA, wherein the first primer is a composite primer comprising an RNA portion and a 3' DNA portion; (b) extending the first primer with an RNA-dependent DNA polymerase, whereby a complex comprising a first primer extension product and the target RNA is produced; (c) cleaving the target RNA in the complex of step (b) with an agent (such as an enzyme) that cleaves RNA from an RNA/DNA hybrid, such that fragments of the target RNA remains hybridized to the first primer extension product; (d) extending the at least one fragment of the target RNA with a DNA-dependent DNA polymerase, whereby a fragment extension product comprising the sequence of interest is produced to form a complex of primer and fragment extension products; (e) cleaving RNA from the composite primer in the complex of primer and fragment extension products with an agent (such as an enzyme) that cleaves RNA from an RNA/DNA hybrid such that a composite primer (which may or may not be the same as the first primer) hybridizes to the fragment extension product and repeats primer extension by strand displacement, wherein said composite primer comprises an RNA portion and a 3' DNA portion; (f) hybridizing a displaced primer extension product with a polynucleotide comprising a propromoter and a region which is hybridizable to the displaced primer extension product under conditions which allow transcription to occur by RNA polymerase, such that RNA transcripts are produced comprising sequences complementary to the displaced primer extension product, whereby multiple copies of the RNA sequence of interest are generated. In some embodiments, the invention provides methods of generating multiple copies of an RNA sequence of interest, said method comprising the steps of: (a) combining: a first complex, wherein the first complex is the complex of primer and fragment extension product of step (d) described above in this paragraph; a composite primer (which may or may not be the same as the first primer) that is hybridizable to the fragment extension product, wherein said composite primer comprises an RNA portion and a 3' DNA portion; a DNA-dependent DNA polymerase; an RNA polymerase; a propromoter polynucleotide comprising a propromoter and a region which hybridizes to a second primer extension product; and an agent (such as an enzyme) that cleaves RNA from an RNA/DNA hybrid; and (b) incubating the mixture of step (a) under conditions (which include necessary substrates and buffer conditions) that permit primer hybridization, RNA cleavage, displacement of the primer extension product from the first complex when its RNA is cleaved and a composite primer binds to the fragment extension product in the first complex, hybridization of the propromoter polynucleotide to the displaced primer extension product to form a second complex comprising the displaced primer extension product and the propromoter polynucleotide, and RNA transcription from said second complex.

In yet another aspect, the invention provides methods of generating multiple copies of (amplifying) a polynucleotide sequence complementary to an RNA sequence of interest, said method comprising the steps of: (a) combining: a target RNA; a primer that is hybridizable to the target RNA, wherein the primer is a composite primer comprising an RNA portion and a 3' DNA portion; an RNA-dependent DNA polymerase; a DNA-dependent DNA polymerase; and an agent (such as an enzyme) that cleaves RNA from an RNA/DNA hybrid; and (b) incubating the mixture of step (a) under conditions (which includes necessary substrates and buffer conditions) that permit primer hybridization, RNA cleavage, wherein RNA cleavage of a first complex comprising a target RNA and a primer extension product is such that a fragment of the target RNA remains hybridized to the primer extension product, primer extension from the primer and the fragment of the target RNA to form a second complex comprising a primer extension product and a fragment extension product that comprises the sequence of interest, and displacement of the primer extension product from the second complex when its RNA is cleaved and another primer binds to the fragment extension product in the second complex, whereby multiple copies of a polynucleotide sequence complementary to the RNA sequence of interest are generated.

In one other aspect, the invention provides methods of generating multiple copies of (amplifying) an RNA sequence of interest, said method comprising the steps of: (a) combining: a target RNA; a primer that is hybridizable to the target RNA, wherein the primer is a composite primer comprising an RNA portion and a 3' DNA portion; an RNA-dependent DNA polymerase; a DNA-dependent DNA polymerase; an RNA polymerase; a propromoter polynucleotide; and an agent (such as an enzyme) that cleaves RNA from an RNA/DNA hybrid; and (b) incubating the mixture of step (a) under conditions (which includes necessary substrates and buffer conditions) that permit primer hybridization, RNA cleavage, wherein RNA cleavage of a first complex comprising a target RNA and a primer extension product occurs such that a fragment of the target RNA remains hybridized to the primer extension product, primer extension from the primer and the fragment of the target RNA to form a second complex comprising a primer extension product and a fragment extension product that comprises the sequence of interest, displacement of the primer extension product from the second complex when its RNA is cleaved and another primer binds to the second complex, hybridization of the propromoter polynucleotide to a displaced primer extension product to form a third complex comprising the displaced primer extension product and the propromoter polynucleotide, and transcription from said third complex, whereby multiple copies of the RNA sequence of interest are generated.

In another aspect, the invention provides methods of generating multiple copies of an RNA sequence of interest present on a target RNA, said method comprising: formation of a complex of first and second primer extension products comprising a 3' single stranded portion according to any of the methods described herein; (c) hybridizing a propromoter oligonucleotide to the 3' single stranded portion described in step (b); and (d) transcription using DNA-dependent RNA polymerase, whereby multiple copies of sense RNA products are generated.

In another aspect, the invention provides methods of generating multiple copies of a sequence complementary to an RNA sequence of interest present on a target RNA and multiple copies of an RNA sequence of interest present on a target RNA, said methods comprising the steps of: (a) extending a first primer hybridized to a target RNA with an RNA-dependent DNA polymerase, wherein the first primer is a composite primer comprising an RNA portion and a 3' DNA portion, whereby a complex comprising a first primer extension product and the target RNA is produced; (b) cleaving RNA in the complex of step (b) with an enzyme that cleaves RNA from an RNA/DNA hybrid; (c) extending a second primer hybridized to the first primer extension product with a DNA-dependent DNA polymerase, wherein the second primer is a composite primer comprising an RNA portion and a 3' DNA portion, whereby a second primer extension product is produced to form a complex of first and second primer extension products; (d) cleaving RNA from the first and second composite primers in the complex of first and second primer extension products with an enzyme that cleaves RNA from an RNA/DNA hybrid such that another composite primer hybridizes to the second primer extension product and another composite primer hybridizes to the first primer extension product; (e) extending said composite primers of step (d) with a DNA-dependent DNA polymerase; whereby said first primer extension product is displaced, and whereby multiple copies of a polynucleotide sequence complementary to the RNA sequence of interest are generated; and whereby said second primer extension product is displaced, and whereby multiple copies of the RNA sequence of interest are generated.

In another aspect, the methods of generating multiple copies of a polynucleotide sequence complementary to an RNA sequence of interest comprise generating multiple copies of a polynucleotide sequence complementary to of two or more different sequences of interest.

In another aspect, the methods of generating multiple copies of an RNA sequence of interest comprise generating multiple copies of two or more different sequences of interest.

Various embodiments of the composite primer and second primer used in the methods of the invention are described herein. For example, in some embodiments, the RNA portion of a composite primer is 5' with respect to the 3' DNA portion. In still other embodiments, the 5' RNA portion is adjacent to the 3' DNA portion. In some embodiments, a composite primer comprises a 5' portion (for example, a 5' RNA portion) that is not hybridizable to a target RNA under conditions which the composite primer hybridizes to target RNA. In yet other embodiments, a composite primer comprises a 3' portion (for example, a 3' DNA portion) that comprises a random sequence. In some embodiments wherein a target RNA is mRNA, a composite primer may comprise a poly-dT sequence. In other embodiments, a composite primer is a random primer. In still other embodiments, a plurality of composite primers are used for hybridizing to the target RNA. In some embodiments, the composite primer that hybridizes to target RNA and the composite primer that hybridizes to second primer extension product are the same. In some embodiments, the composite primer that hybridizes to target RNA and the composite primer that hybridizes to second primer extension product are different.

In still other embodiments, the second primer is a primer comprising DNA (in some embodiments, consisting of DNA). In other embodiments, the second primer comprises one or more fragments of target RNA hybridized to the first primer extension product, said one or more fragments generated by cleaving RNA in the complex of target RNA and first primer extension product with an enzyme that cleaves RNA from an RNAIDNA hybrid. In other embodiments, the second primer comprises a portion (for example, a 3' portion) that comprises a random sequence. In yet another embodiment, the second primer is a random primer. In some embodiments, the second primer comprises a 5' portion that is not hybridizable to a first primer extension product. For the methods described herein, one or more composite primers or second primers can be used.

The enzymes which may be used in the methods and compositions are described herein. For example, the agent (such as an enzyme) that cleaves RNA may be an RNaseH, and the RNA-dependent DNA polymerase may be reverse transcriptase. The RNA-dependent DNA polymerase may comprise an RNase H enzyme activity, or separate enzymes may be used. Similarly, a DNA polymerase may comprise both RNA-dependent and DNA-dependent DNA polymerase enzyme activities, or separate enzymes may be used. A DNA-dependent DNA polymerase and an enzyme that cleaves RNA may also be the same enzyme. A DNA-dependent DNA polymerase, an RNA-dependent DNA polymerase, and the enzyme that cleaves RNA can also be the same enzyme.

In some embodiments, methods of the invention are used to generate labeled polynucleotide products (generally DNA or RNA products). In some embodiments of methods for generating labeled DNA products, at least one type of dNTP used is a labeled dNTP. In some embodiments of methods for generating labeled RNA products, at least one type of rNTP used is a labeled rNTP. In other embodiments of methods for generating labeled DNA products, a labeled composite primer is used.

In some aspects, a propromoter polynucleotide (for example, a PTO) comprises a region at the 3' end which hybridizes to the displaced primer extension product, whereby DNA polymerase extension of displaced extension product produces a double stranded promoter from which transcription occurs.

The methods are applicable to amplifying any RNA target, including, for example, mRNA and ribosomal RNA. One or more steps may be combined and/or performed sequentially (often in any order, as long as the requisite product(s) are able to be formed), and, as is evident, the invention includes various combinations of the steps described herein. It is also evident, and is described herein, that the invention encompasses methods in which the initial, or first, step is any of the steps described herein. For example, the methods of the invention do not require that the first step be production of the first primer extension product from the RNA template. Methods of the invention encompass embodiments in which later, "downstream" steps are an initial step.

Further, in various embodiments of the invention, it is understood that the first primer extension product comprises (a) a sequence complementary to an RNA sequence and (b) a 5' portion, preferably a 5' end, that is RNA. As described, this product generally arises from primer extension of a composite primer with an RNA portion along an RNA template. As such, reference to a first primer extension product refers to a product comprising (a) and (b) above.

The invention also provides methods which employ (usually, analyze) the products of the amplification methods of the invention, such as sequencing, detection of sequence alteration(s) (e.g., genotyping or nucleic acid mutation detection); determining presence or absence of a sequence of interest; gene expression profiling; subtractive hybridization; preparation of a subtractive hybridization probe; differential amplification; preparation of libraries (including cDNA and differential expression libraries); preparation of an immobilized nucleic acid (which can be a nucleic acid immobilized on a microarray), and characterizing (including detecting and/or quantifying) amplified nucleic acid products generated by the methods of the invention.

In some aspects, the invention provides methods of sequencing an RNA sequence of interest, said methods comprising amplifying a target RNA containing the sequence of interest by the amplification methods of the invention in the presence of a mixture of dNTPs and dNTP analogs (which may be labeled or unlabeled), such that primer extension is terminated upon incorporation of a dNTP analog which may be labeled or unlabeled, and analyzing the amplification products to determine sequence. In embodiments wherein amplified products are RNA transcripts, the methods may comprise (a) amplifying a target RNA containing the sequence of interest by the amplification methods of the invention in the presence of a mixture of rNTPs and rNTP analogs (which may be labeled or unlabeled), such that RNA transcription is terminated upon incorporation of an rNTP analog which may be labeled or unlabeled; and (b) analyzing the amplification products to determine sequence.

In some aspects, the invention provides methods of detecting a mutation (or, in some aspects, characterizing a sequence) in a target RNA, comprising (a) amplifying the target RNA by a method described herein; and (b) analyzing the amplification products of the method for single stranded conformation, wherein a difference in conformation as compared to a reference single stranded RNA indicates a mutation in the target RNA. In other embodiments, the invention provides methods of detecting a mutation (or, in some aspects, characterizing a sequence) in a target RNA comprising analyzing amplification products of any of the methods described herein for single stranded conformation, wherein a difference in conformation as compared to a reference single stranded RNA indicates a mutation in the target RNA (or, in some aspects, characterizes the target sequence).

In another aspect, the invention provides methods of determining presence or absence of a sequence of interest, said methods comprising (i) amplifying a target RNA containing the sequence of interest, said amplification comprising extending a composite primer hybridized to cleaved complex of first and second primer extension product prepared by any of the methods described here, wherein the sequence of the RNA portion of the composite primer is known, and (ii) comparing the amplification products if any from step (i) with the amount of amplification products from a reference template; wherein (1) production of detectably fewer amplification products from the template as compared to the amount of amplification products from the reference template which comprises a region hybridizable to the RNA portion of the composite primer indicates that the second primer extension product does not comprise a sequence hybridizable to the RNA portion of the composite primer and is a sequence variant with respect to the sequence hybridizable to the RNA portion of the composite primer; or (2) production of detectably more amplification products from the template as compared to the amount of amplification products from the reference template which does not comprise a region which is hybridizable to the RNA portion of the composite primer indicates that the second primer extension product comprises a sequence hybridizable to the RNA portion of the composite primer and is not a sequence variant with respect to the sequence hybridizable to the RNA portion of the composite primer.

In another aspect, the invention provides methods of producing a nucleic acid immobilized to a substrate (which includes methods of producing a microarray), comprising (a) amplifying a target RNA by any of the methods described herein; and (b) immobilizing the amplification products on a substrate. The amplification products can be labeled or unlabeled. In other aspects, the invention provides methods of producing a microarray, comprising (a) amplifying a target RNA by an amplification method described herein; and (b) immobilizing the amplification products on a substrate (which can be solid or semi-solid). In some embodiments, microarrays are produced by immobilizing amplification products onto a substrate to make a microarray of amplification products. The microarray can comprise at least one amplification product immobilized on a solid or semi-solid substrate fabricated from a material selected from the group consisting of paper, glass, ceramic, plastic, polystyrene, polypropylene, nylon, polyacrylamide, nitrocellulose, silicon and other metals, and optical fiber. An amplification product can be immobilized on the solid or semi-solid substrate in a two-dimensional configuration or a three-dimensional configuration comprising pins, rods, fibers, tapes, threads, beads, particles, microtiter wells, capillaries, and cylinders.

Any of the methods of the invention can be used to generate polynucleotide (generally, DNA or RNA) products that are suitable for characterization of an RNA sequence of interest in a sample. In one embodiment, the invention provides methods for characterizing (for example, detecting (presence or absence) and/or quantifying) an RNA sequence of interest comprising: (a) amplifying a target RNA by any of the methods described herein; and (b) analyzing the amplification products. Step (b) of analyzing the amplification products can be performed by any method known in the art or described herein, for example by detecting and/or quantifying amplification products that are hybridized to a probe. These amplification products may or may not be labeled. Any of the methods of the invention can be used to generate DNA or RNA products that are labeled by incorporating labeled nucleotides and/or labeled composite primers into appropriate step(s) of the methods. These labeled products are particularly suitable for quantification and/or identification by methods known in the art, which include the use of arrays such as cDNA microarrays and oligonucleotide arrays. In one aspect, the invention provides a method of characterizing an RNA sequence of interest, comprising (a) amplifying a target RNA by a method described herein to generate labeled DNA products; and (b) analyzing the labeled DNA products. In some embodiments, the step of analyzing DNA products comprises determining amount of said products, whereby the amount of the RNA sequence of interest present in a sample is quantified.

In another aspect, the invention provides a method of characterizing an RNA sequence of interest, comprising (a) amplifying a target RNA by a method described herein to generate labeled RNA products; and (b) analyzing the labeled RNA products. In some embodiments, the step of analyzing RNA products comprises determining amount of said products, whereby the amount of the RNA sequence of interest present in a sample is quantified. The DNA or RNA products can be analyzed by, for example, contacting them with at least one probe. In some embodiments, the at least one probe is provided as a microarray. The microarray can comprise at least one probe immobilized on a solid or semi-solid substrate fabricated from a material selected from the group consisting of paper, glass, ceramics, plastic, polypropylene, polystyrene, nylon, polyacrylamide, nitrocellulose, silicon, other metals, and optical fiber. A probe can be immobilized on the solid or semi-solid substrate in a two-dimensional configuration or a three-dimensional configuration comprising pins, rods, fibers, tapes, threads, beads, particles, microtiter wells, capillaries, and cylinders.

In another aspect, the invention provides methods of determining gene expression profile in a sample, the methods comprising: (a) amplifying at least one RNA sequence of interest in the sample using any of the methods described herein; and (b) determining amount of amplification products of each RNA sequence of interest, wherein each said amount is indicative of amount of each RNA sequence of interest in the sample, whereby the gene expression profile of the sample is determined.

In another aspect, the invention provides methods of preparing a library (including cDNA and subtractive hybridization libraries), said methods comprising: amplifying at least one RNA sequences of interest using any of the methods described herein to generate a single or double stranded nucleic acid product.

In another aspect, the invention provides methods of preparing a subtractive hybridization probe, said methods comprising generating multiple single stranded polynucleotide, preferably DNA, copies of the complement of at least one RNA sequences of interest from a first RNA population using any of the methods described herein.

In another aspect, the invention provides methods of performing subtractive hybridization, said methods comprising: (a) generating multiple copies of the complement of at least one RNA sequences of interest from a first RNA population using any of the methods described herein; and (b) hybridizing the multiple copies to a second mRNA population, whereby a subpopulation of the second mRNA population forms a complex with a DNA copy. In some embodiments, the methods further comprise: (c) cleaving RNA in the complex of step (b) with an enzyme that cleaves RNA from an RNA/DNA hybrid; and (d) amplifying an unhybridized subpopulation of the second mRNA population (using any method, including the methods described herein), whereby multiple copies of single stranded DNA complementary to the unhybridized subpopulation of the second mRNA population are generated.

In another aspect, the invention provides methods for differential amplification, the methods comprising: (a) generating multiple nucleic acid, generally DNA, copies of the complement of at least one RNA sequence of interest from a first RNA population using any of the methods described herein; (b) hybridizing the multiple copies to a second mRNA population, whereby a subpopulation of the second mRNA population forms a complex with a DNA copy; (c) cleaving RNA in the complex of step (b) with an enzyme that cleaves RNA from an RNA/DNA hybrid; and (d) amplifying an unhybridized subpopulation of the second mRNA population using any method, including those described herein, whereby multiple copies of single stranded DNA complementary to the unhybridized subpopulation of the second mRNA population are generated.

In another aspect, the invention provides methods for making a library, said method comprising preparing a subtractive hybridization probe as described herein, or differential amplification as described herein.

Any of these applications can use any of the amplification methods (including various components and various embodiments of any of the components) as described herein. For example, the composite primer used may have a 5' RNA portion, which may be adjacent to the 3' DNA portion.

The invention also provides compositions, kits, complexes, reaction mixtures and systems comprising various components (and various combinations of the components) used in the amplification methods described herein. In one aspect, for example, the invention provides compositions comprising a composite primer, wherein the composite primer comprises an RNA portion and a 3' DNA portion, and a second primer, wherein the second primer is a random primer. In some embodiments, these compositions further comprise an RNA-dependent DNA polymerase (which can be a reverse transcriptase). In another embodiment, the invention provides a composition comprising a composite primer and a second primer that comprises a sequence that is not hybridizable (under conditions in which a region of primer is hybridizable) to a composite primer extension product (generally, but not necessarily, the use of this primer results in generating primer extension products to which a propromoter polynucleotide can hybridize). In some embodiments, the 5' RNA portion of a composite primer is adjacent to its 3' DNA portion. In still other embodiments, the 5' RNA portion of a composite primer is about 5 to about 20 nucleotides and its 3' DNA portion is about 5 to about 15 nucleotides. In some embodiments, the propromoter polynucleotide is a propromoter template oligonucleotide (PTO). In still other embodiments, the invention provides a composition comprising: (a) a composite primer; (b) a second primer (which can be a random primer); and (c) a propromoter polynucleotide (which in some embodiments is a PTO).

In another aspect, the invention provides compositions comprising any of the complexes (which are generally considered as intermediates with respect to the final amplification products) described herein (see also the figures for exemplary schematic depictions of these various complexes). For example, the invention provides compositions comprising a complex of: (a) a first primer extension strand, wherein the first primer is a composite primer comprising an RNA portion and a 3' DNA portion; and (b) a target RNA strand. In yet another aspect, the invention provides compositions comprising a complex of: (a) a first primer extension product, wherein the first primer is a composite primer comprising an RNA portion and a 3' DNA portion; and (b) a second primer (or fragment) extension product. In still another aspect, the invention provides a complex of (a) a cleaved primer extension product, wherein the primer is a composite primer comprising an RNA portion and a 3' DNA portion; (b) a second primer (or fragment) extension product; and (c) a composite primer.

In another aspect, the invention includes any one or more products (including intermediates) and compositions comprising the products (including intermediates) produced by any aspect of the methods of the invention. The products include libraries and any other population produced, which are generally based on the nature of the primer(s) used in the methods described herein.

In another aspect, the invention provides reaction mixtures (or compositions comprising reaction mixtures) which contain various combinations of components described herein. For example, the invention provides reaction mixtures comprising (a) a target RNA; (b) a composite primer comprising a 3' DNA portion and an RNA portion; (c) a second primer; and (d) a DNA polymerase. As described herein, any of the composite primers may be in the reaction mixture (or a plurality of composite primers), including a composite primer that comprises a 5' RNA portion which is adjacent to the 3' DNA portion. The reaction mixture could also further comprise an enzyme which cleaves RNA from an RNA/DNA hybrid, such as RNase H. A reaction mixture of the invention can also comprise a propromoter polynucleotide (which in some embodiments is a PTO), and/or an RNA polymerase. A reaction mixture of the invention can also comprise (a) a displaced primer extension product (which contains a 5' end sequence complementary to the 3' DNA portion of a composite primer, but not sequences complementary to the RNA portion of a composite primer); (b) a propromoter polynucleotide (such as a PTO); and (c) an RNA polymerase.

In another aspect, the invention provides kits for conducting the methods described herein. These kits, in suitable packaging and generally (but not necessarily) containing suitable instructions, contain one or more components used in the amplification methods. For example, the invention provides kits that comprise a composite primer comprising a 3' DNA portion and an RNA portion (which may be 5' and may further be adjacent to the 3' DNA portion), and a second primer (which may or may not be separately packaged). In some embodiments, these kits further comprise instructions for using the primers to amplify RNA. The composite primer in the kits can be any described herein. The kits can contain further components, such as any of (a) a propromoter polynucleotide (such as a PTO); and (b) any of the enzymes described herein, such as an enzyme which cleaves RNA from an RNA/DNA hybrid (for example, RNaseH), DNA polymerase (RNA-dependent or DNA-dependent) and RNA polymerase. Any of these kits can further comprise instructions for using the components to amplify RNA.

In another aspect, the invention provides systems for effecting the amplification methods described herein. For example, the invention provides systems for amplifying a target RNA, comprising (a) a composite primer comprising a 3' DNA portion and an RNA portion; (b) a second primer; (c) an RNA-dependent DNA polymerase; (d) a DNA-dependent DNA polymerase; and (e) an enzyme which cleaves RNA from an RNA/DNA hybrid (such as RNaseH). The composite primer may be any (one or more) described herein, including a composite primer which comprises a 5' RNA portion which is adjacent to the 3' DNA portion. The systems can further comprise a propromoter polynucleotide (such as a PTO) and/or an RNA polymerase. As described herein, systems of the invention generally comprise one or more apparatuses appropriate for carrying out methods of the invention.

BRIEF DESCRIPTION OF THE DRAWINGS

FIGS. 6A-D shows a diagrammatic representation of a linear isothermal RNA amplification process using a single composite primer containing a random sequence and strand displacement to generate multiple copies of single stranded DNA product comprising sequences complementary to the target RNA.

MODES FOR CARRYING OUT THE INVENTION

Figure 1A:
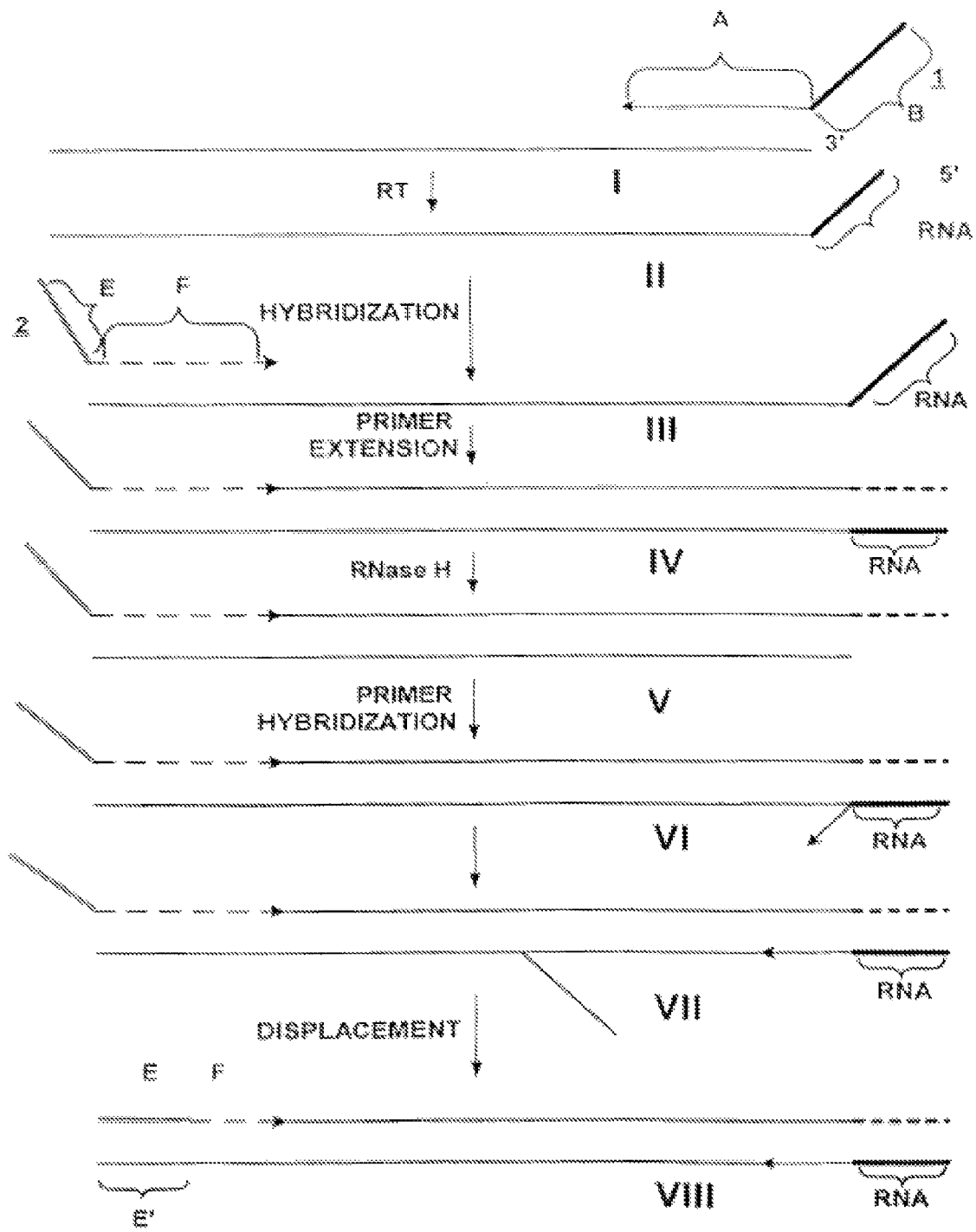
FIGS. 1A-1B show a diagrammatic representation of a linear isothermal RNA amplification process using a composite primer, a second primer, and strand displacement to generate multiple copies of single stranded DNA product comprising sequences complementary to the target RNA.

Overview of the Invention and its Advantages

The invention discloses novel methods, compositions and kits for amplification of RNA sequences. The methods provide for isothermal amplification of a single RNA species or a pool of RNA species. Some methods provide for generation of multiple copies of DNA comprising sequences complementary to an RNA sequence of interest. Other methods provide for generation of multiple copies of an RNA sequence of interest. These methods are suitable for, for example, generation of cDNA libraries and subtractive hybridization probes. They generate single stranded DNA or RNA products, which are readily suitable for a variety of uses including expression profiling, e.g., by multiplex analysis by microarray technologies, as well as electrophoresis-based technologies such as differential display. The methods are amenable to automation and do not require thermal cycling.

The methods of the invention are directed to the amplification of one or more species of RNA, such as a pool of RNA sequences, and are especially suitable for the amplification of all RNA (such as mRNA) sequences in a preparation of total RNA from a biological sample. Thus, one of the major advantages of the methods of the invention is the ability to amplify an entire pool of sequences, which is essential for the ability to analyze the gene expression profile in cells, such as the cells in a biological sample of interest. The methods of the invention may also be used to amplify a specific RNA sequence of interest, or a multiplicity of RNAs, for example, members of a family of related RNAs. The methods of the invention also are suitable for amplifying a large multiplicity, and most preferably all RNA (such as mRNA) sequences in a sample.

Insofar as many mRNAs have a unique poly-A 3'-end, amplification initiated from the 3'-end sequence of mRNAs is commonly performed for preparation of cDNA libraries and subsequent sequence analysis for determination of gene expression profiling or other applications. The methods of the invention are similarly suited for preparation of libraries of amplified 3'-portions of mRNAs. A composite primer used in the methods of invention can be designed to be hybridizable to a multiplicity, or all, of the mRNA species in the sample by using random sequences, according to methods known in the art. Alternatively, if a selected RNA or family of related RNAs are to be amplified, the composite primer will comprise sequence(s) hybridizable to the selected RNA or family of related RNAs.

The methods generally comprise using specially-designed primers, generally one or more RNA/DNA composite primers, to generate a complex of first and second strand cDNAs that comprise a portion with a particular characteristic (e.g., cleavable by an enzyme). As used herein, it is understood that "cDNA" refers to a polynucleotide primer extension product. Generally, the complex comprises an RNA/DNA heteroduplex at an end of the double stranded cDNA complex. The RNA/DNA heteroduplex at an end of the double stranded cDNA complex may comprise a defined end sequence, generally introduced by the RNA portion of the composite primer. The composite primer according to the methods of the invention comprises a 3'-DNA portion that generally is designed to be hybridizable to a target RNA(s). The remaining portion(s) (such as the 5' RNA portion) of the composite primer generally, but not necessarily, comprises a sequence that is not hybridizable to a target RNA (which would constitute a tail when the primer is bound to a target RNA). Thus, and as the description herein makes clear, reference to a primer that hybridizes to a sequence (or hybridization template) encompasses embodiments in which at least a portion of the primer is hybridized, as well as those embodiments in which an entire primer is hybridized.

The double stranded cDNA complex is a substrate for linear amplification as follows: an enzyme which cleaves RNA from an RNA/DNA hybrid (such as RNase H) cleaves RNA sequence from the hybrid, leaving a 3' DNA sequence on the second strand cDNA available for binding by a composite primer which may or may not be the same as the first composite primer. Extension of a bound composite primer by DNA polymerase produces a primer extension product, which displaces the previously bound cleaved first primer extension product, whereby single stranded DNA product accumulates. The single stranded DNA product is a copy of the complement of the target RNA (or "antisense" DNA). This linear amplification is referred to as "SPIN" (for Single Primer Linear Amplification), and is described in Kurn et al., U.S. Pat. No. 6,251,639 B1.

In one aspect, the invention works as follows: a composite RNA/DNA primer forms the basis for replication of the template RNA The composite primer (also referred to herein as "the first primer") hybridizes to template RNA which comprises the RNA sequence(s) of interest, and the composite primer is extended by an RNA-dependent DNA polymerase to form a first primer extension product (interchangeably called "composite primer extension product", or "first-strand cDNA"). After cleavage of the template RNA, a second primer extension product (interchangeably called "second-strand cDNA") is formed (as described below) in a complex with the first primer extension product. The complex of first and second primer extension products is composed of an RNA/DNA hybrid at one end due to the presence of the composite primer in the first primer extension product. An agent such as an enzyme which cleaves RNA from an RNA/DNA hybrid (such as RNase H) cleaves RNA sequence from the hybrid, leaving a sequence on the second primer extension product available for binding by another composite primer, which may or may not be the same as the first composite primer. Another first (composite) primer extension product is produced by DNA polymerase, which displaces the previously bound cleaved first primer extension product, resulting in displaced cleaved first primer extension product.

In some embodiments of the invention, the second primer extension product is formed as follows: following cleavage of the RNA template, a second primer is then hybridized to the first primer extension product and extended to form a second primer extension product in a complex with the first primer extension product. The complex of first and second primer extension products is composed of an RNA/DNA hybrid at one end due to the presence of the composite primer in the first primer extension product. The second primer is any sequence that is hybridizable to the first DNA strand such that it is capable of being extended by a DNA polymerase along a first primer extension product to create a second primer extension product. Thus, in some embodiments, the second primer is an oligonucleotide, which may or may not comprise a random sequence (i.e., a sequence designed to be hybridizable (under a given set of conditions) to one or more sequences in the sample). In other embodiments, it comprises a sequence of the first DNA strand (generally at the 3' end) that is hybridized to a sequence in the first DNA strand (for example, a hairpin or self-annealed structure).

In another aspect of the amplification methods, one or more fragments of the target RNA serves as the primer of the second primer extension product. The target RNA in the initial complex comprising the target RNA and first primer extension product is cleaved with an agent (such as RNase H) such that at least one fragment of the template RNA remains hybridized to the first primer extension product. In this aspect of the invention, one (or more) template RNA fragment(s) serves as a second "primer" in the manner described above, to generate a fragment extension product which has the same function as the second primer extension product in the amplification methods described above. A suitable RNA fragment in the methods of the invention is long enough such that it does not dissociate from the first strand cDNA, preferably from about 3 to about 30, more preferably from about 5 to about 25, even more preferably from about 10 to about 20, and most preferably from about 12 to about 17, nucleotides in length.

In embodiments involving transcription (referred to herein as "enhanced" methods), the second primer may further comprise a sequence such that displaced first primer extension products (other than the very first composite primer extension product) contain a sequence to which a polynucleotide comprising a propromoter (also referred to herein as "propromoter polynucleotide") is capable of hybridizing. Hybridization of the propromoter polynucleotide to a displaced primer extension product and extension of the 3' end of the displaced first primer extension product (if there is an overhang) results in a double stranded promoter region that drives transcription (via DNA-dependent RNA polymerase) to produce sense RNA products. This "enhanced" approach is described in Kurn et al., U.S. Pat. No. 6,251,639 B1.

Accordingly, the invention provides methods of producing at least one copy of a polynucleotide sequence complementary to an RNA sequence of interest comprising combining and reacting the following: (a) a target RNA comprising an RNA sequence of interest; (b) a first (composite) primer comprising an RNA portion and a 3' DNA portion; (c) a second primer that is hybridizable to an extension product of the composite primer; (d) an RNA-dependent DNA polymerase; (e) a DNA-dependent DNA polymerase; (f) an agent (such as an enzyme) that cleaves RNA from an RNA/DNA hybrid; and (g) deoxyribonucleoside triphosphates or suitable analogs (which may or may not be labeled). In embodiments that include transcription (i.e., the enhanced methods), the following are also included in the amplification reaction (either at the same time as the components listed above or added separately): (h) a propromoter polynucleotide comprising a propromoter and a region which hybridizes to an extension product of the first primer (a displaced primer extension product); (i) an RNA polymerase; and (j) ribonucleoside triphosphates or suitable analogs (which may or may not be labeled). The combination is subjected to suitable conditions for primer hybridization, extension of primers, RNA cleavage, and displacement of the first primer extension product when its RNA is cleaved and another first primer binds in the site vacated by the cleaved RNA. In embodiments that include transcription, conditions employed are also suitable for hybridization of the propromoter polynucleotide to the displaced cleaved first primer extension product, extension of the 3' end of the cleaved first primer extension product (if necessary) to generate a double-stranded promoter region, and RNA transcription driven by the promoter. As described and exemplified herein, the above-described reaction mixture may be subdivided into two or more different reaction mixtures for separate, generally sequential, incubations that correspond to different aspects of the amplification process (see, for example, Example 1).

In another aspect of the amplification methods, fragments of the target RNA serves as a primer of second DNA strand synthesis. The target RNA in the initial complex comprising the target RNA and composite primer extension product is cleaved with an enzyme (such as RNaseH) such that at least one fragment of the template RNA remains hybridized to the composite primer extension product. In this aspect of the invention, one (or more) template RNA fragment(s) serves as a second "primer" in the manner described above, to generate a fragment extension product which has the same function as the second primer extension product in the amplification methods described above.

In some embodiments, the invention provides methods of producing at least one copy of a polynucleotide sequence complementary to an RNA sequence of interest comprising combining and reacting the following: (a) complex of first and second primer extension products; (b) a first (composite) primer comprising an RNA portion and a 3' DNA portion; (c) a DNA-dependent DNA polymerase; (d) an agent (such as an enzyme) that cleaves RNA from an RNA/DNA hybrid; and (e) deoxyribonucleoside triphosphates or suitable analogs (which may or may not be labeled). In embodiments that include transcription, the following are also included in the amplification reaction (either at the same time as the components listed above or added separately): (f) a propromoter polynucleotide comprising a propromoter and a region which hybridizes to an extension product of the first primer (a displaced primer extension product); (g) an RNA polymerase; and (h) ribonucleoside triphosphates or suitable analogs (which may or may not be labeled). The combination is subjected to suitable conditions for primer hybridization, extension of primers, RNA cleavage, and displacement of the first primer extension product when its RNA is cleaved and another first primer binds in the site on the second primer extension product vacated by the cleaved RNA. In embodiments that include transcription, conditions employed are also suitable for hybridization of the propromoter polynucleotide to the displaced first primer extension product, extension of the 3' end of the first primer extension product (if necessary) to generate a double-stranded promoter region, and RNA transcription driven by the promoter.

In another aspect, the invention provides methods of producing single stranded antisense and sense DNA copies of an RNA sequence of interest using a first composite primer, a second composite primer (termed the "reverse composite" primer), and a target RNA fragment. The method involves the following: (a) formation of a double stranded cDNA comprising a RNA-DNA heteroduplex at each end of the double stranded cDNA; and (b) linear amplification of first strand (sense) cDNA and second strand (antisense) cDNA by primer extension from two composite primers and strand displacement. Single stranded first and second strand cDNA product is produced. This product is useful in, e.g., producing cDNA libraries. As is evident, in this aspect of the invention, the second primer extension product is primed by a composite primer.

The methods of the invention include methods using the amplified products (so-called "applications"). In some embodiments, the invention provides methods of sequencing RNA sequences. For sequencing methods based on methods described herein wherein the amplified product is DNA, the appropriate dNTPs, or analogs thereof, which may be labeled or unlabeled, are used. For sequencing methods based on methods described herein wherein the amplified product is RNA, the appropriate rNTPs, or analogs thereof, which may be labeled or unlabeled, may be used.

In other embodiments, the invention provides methods of detecting nucleic acid sequence mutations. In one embodiment, the amplified products are used to detect and/or identify single strand conformation polymorphisms in a target polynucleotide.

The invention provides methods to characterize (for example, detect presence or absence of and/or quantify) an RNA sequence of interest by generating DNA or RNA products using amplification methods of the invention, and analyzing the products by detection/quantification methods such as those based on array technologies or solution phase technologies. These amplified products may be labeled or unlabeled.

In yet another embodiment, the invention provides methods for immobilizing nucleic acids, including methods for generating microarrays of nucleic acids (DNA or RNA) using amplified products of the amplification methods of the invention.

In another embodiment, the invention provides methods of generating cDNA libraries, methods of generating subtractive hybridization probes, and methods of generating subtractive hybridization libraries.

Various methods for the detection and quantification of gene expression levels have been developed in recent years. For example, microarrays, in which either defined cDNAs or oligonucleotides are immobilized at discrete locations on, for example, solid or semi-solid substrates, or on defined particles, enable the detection and/or quantification of the expression of a multitude of genes in a given specimen.

Using these previously known methods to detect presence of absence of and/or quantify multiple mRNA species in a sample, which in turn is used as a measure of gene expression profiling, generally requires direct labeling of cDNA, which requires a large amount of input total RNA, in part because mRNA represents only a small subset of the total RNA pool. Thus, when using total RNA preparations from a given cell or tissue sample, the analysis of gene expression in the sample using methods such as arrays requires a substantial amount of input RNA, which generally ranges from 50 to 200 µg. Similarly, 2 to 5 µg of mRNA purified from a total RNA preparation would generally be required for a single analysis of gene expression profiling using array technologies. This is a clear limitation of methods such as those based on array technology, insofar the number of cells, or size of tissue specimen required is very large, and these cells or tissue specimens are often scarcely available for testing or are too precious. This limitation is especially severe in the study of clinical specimens, where the cells to be studied are rare and/or difficult to cultivate in vitro, and in high throughput screening of libraries of effector molecules. Also, previous transcription-based methods of amplification of mRNA (described in, for example, Lockhart et al, *Nature Biotechnology* (1996), 14, 1675-1680); van Gelder et al., U.S. Pat. No. 5,716,785), are limited to the amplification efficiency of DNA-dependent RNA polymerases and some of these methods require multiple steps. Moreover, the process by which the polymerase promoter sequence is incorporated is prone to result in non-specific amplification.

The methods of the invention offer the ability to efficiently amplify mRNA under conditions that provide for high specificity of target amplification and which is generally reflective of the distribution in the input RNA. Thus, the utility of the detection/quantification methods which can be used with the amplification products of the invention, such as those based on the powerful array technology, real time PCR, quantitative TaqMan, quantitative PCR using molecular beacons and the like, should be greatly enhanced.

The linear aspect of the amplification methods of the invention significantly increases the specificity of target amplification. Since generation of multiple copies of a sequence of interest is not dependent nor based on cyclical, exponential, amplification of amplification products, the specificity of products obtained is greatly enhanced. The distribution of the various species of amplified products is generally reflective of the distribution in the input RNA.

The methods of the invention do not require thermocycling and all of the steps can be performed isothermally, although the various steps may be carried out a different temperatures. This feature provides numerous advantages, including facilitating automation and adaptation for high through-put procedures. The isothermal reaction is faster than that afforded by thermal cycling and is suitable for performing the methods of the invention in miniaturized devices.

The intermediate double stranded cDNA complex comprising an RNA/DNA heteroduplex provides a substrate for linear amplification. Cleavage of the RNA portion of the RNA/DNA heteroduplex permits further amplification without the need to denature the double stranded cDNA intermediate complex. Moreover, since the cleaved double stranded cDNA complex is mostly double stranded, it is less likely that the secondary structure of a single stranded template will interfere with subsequence amplification.

Finally, most of the methods of the invention produce products that are single stranded, thus rendering them more accessible to binding to probes, either in a homogeneous manner, i.e. in solution, or binding to probes immobilized on solid supports. The double stranded products of the methods of the invention are useful for, e.g., production of cDNA libraries.

The ability to efficiently amplify mRNA (or any other desired RNA species or population) under conditions that provides for high specificity of target amplification and which will generally not alter the representation of the various mRNA species in the preparation, will greatly enhance the utility of the detection/quantification methods such as those based on the powerful array technology.

General Techniques

The practice of the invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994).

Primers, oligonucleotides and polynucleotides employed in the invention can be generated using standard techniques known in the art.

DEFINITIONS

A "target sequence," "target nucleic acid," or "target RNA," as used herein, is a polynucleotide comprising a sequence of interest, for which amplification is desired. The target sequence may be known or not known, in terms of its actual sequence. In some instances, the terms "target," "template," and variations thereof, are used interchangeably.

"Amplification," or "amplifying", as used herein, generally refers to the process of producing multiple copies of a desired sequence. "Multiple copies" mean at least 2 copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template, or a non-target sequence introduced through a primer), and/or sequence errors that occur during amplification. "Amplifying" a sequence may generally refer to making copies of a sequence or its complement, with the understanding that, as stated above, copying does not necessarily mean perfect sequence complementarity or identity with respect to the template sequence.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-0-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A "labeled dNTP," or "labeled rNTP," as used herein, refers, respectively, to a dNTP or rNTP, or analogs thereof, that is directly or indirectly attached with a label. For example, a "labeled" dNTP or rNTP, may be directly labeled with, for example, a dye and/or a detectable moiety, such as a member of a specific binding pair (such as biotin-avidin). A "labeled" dNTP or rNTP, may also be indirectly labeled by its attachment to, for example, a moiety to which a label is/can be attached. A dNTP or rNTP, may comprise a moiety (for example, an amine group) to which a label may be attached following incorporation of the dNTP or rNTP into an extension product. Useful labels in the present invention include fluorescent dyes (e.g., fluorescein isothiocyanate, Texas red, rhodamine, green fluorescent protein and the like), radioisotopes (e.g., $^3$H, $^{35}$S, $^{32}$P, $^{33}$P, $^{125}$I, or $^{14}$C), enzymes (e.g., LacZ, horseradish peroxidase, alkaline phosphatase), digoxigenin, and colorimetric labels such as colloidal gold or colored glass or plastic (e.g., polystyrene, polypropylene, latex, etc.) beads. Various anti-ligands and ligands can be used (as labels themselves or as a means for attaching a label). In the case of a ligand that has a natural anti-ligand, such as biotin, thyroxine and cortisol, the ligand can be used in conjunction with labeled anti-ligands.

The "type" of dNTP or rNTP, as used herein, refers to the particular base of a nucleotide, namely adenine, cytosine, thymine, uridine, or guanine.

"Oligonucleotide," as used herein, generally refers to short, generally single stranded, generally synthetic polynucleotides that are generally, but not necessarily, less than about 200 nucleotides in length. Oligonucleotides in the invention include the composite primer and propromoter polynucleotide (such as the PTO). The terms "oligonucleotide" and "polynucleotide" are not mutually exclusive. The description above for polynucleotides is equally and fully applicable to oligonucleotides.

A "primer," as used herein, refers to a nucleotide sequence, generally with a free 3'-OH group, that hybridizes with a template sequence (such as a target RNA, or a primer extension product) and is capable of promoting polymerization of a polynucleotide complementary to the template. A "primer" can be, for example, an oligonucleotide. It can also be, for example, a sequence of the template (such as a primer extension product or a fragment of the template created following RNase cleavage of a template-DNA complex) that is hybridized to a sequence in the template itself (for example, as a hairpin loop), and that is capable of promoting nucleotide polymerization. Thus, a primer can be an exogenous (e.g., added) primer or an endogenous (e.g., template fragment) primer.

A "random primer," as used herein, is a primer that comprises a sequence that is designed not necessarily based on a particular or specific sequence in a sample, but rather is based on a statistical expectation (or an empirical observation) that the sequence of the random primer is hybridizable (under a given set of conditions) to one or more sequences in the sample. The sequence of a random primer (or its complement) may or may not be naturally-occurring, or may or may not be present in a pool of sequences in a sample of interest. The amplification of a plurality of RNA species in a single reaction mixture would generally, but not necessarily, employ a multiplicity, preferably a large multiplicity, of random primers. As is well understood in the art, a "random primer" can also refer to a primer that is a member of a population of primers (a plurality of random primers) which collectively are designed to hybridize to a desired and/or a significant number of target sequences. A random primer may hybridize at a plurality of sites on a nucleic acid sequence. The use of random primers provides a method for generating primer extension products complementary to a target polynucleotide which does not require prior knowledge of the exact sequence of the target.

"Protopromoter sequence," and "propromoter sequence," as used herein, refer to a single-stranded DNA sequence region which, in double-stranded form is capable of mediating RNA transcription. In some contexts, "protopromoter sequence," "protopromoter," "propromoter sequence," "propromoter," "promoter sequence," and "promoter" are used interchangeably.

A "propromoter polynucleotide," as used herein, refers to a polynucleotide comprising a propromoter sequence. Example of a propromoter polynucleotide is a propromoter template oligonucleotide (PTO).

"Propromoter template oligonucleotide (PTO)" and "promoter template oligonucleotide (PTO)" as used herein, refer to an oligonucleotide that comprises a propromoter sequence and a portion, generally a 3' portion, that is hybridizable (under a given set of conditions) to the 3' region of a primer extension product. The propromoter sequence and the hybridizable portion may be the same, distinct or overlapping nucleotides of an oligonucleotide.

To "inhibit" is to decrease or reduce an activity, function, and/or amount as compared to a reference.

A "complex" is an assembly of components. A complex may or may not be stable and may be directly or indirectly detected. For example, as is described herein, given certain components of a reaction, and the type of product(s) of the reaction, existence of a complex can be inferred. For purposes of this invention, a complex is generally an intermediate with respect to the final amplification product(s). An example of a complex is a nucleic acid duplex comprising a first primer extension product and a second primer extension product.

A "portion" or "region," used interchangeably herein, of a polynucleotide or oligonucleotide is a contiguous sequence of 2 or more bases. In other embodiments, a region or portion is at least about any of 3, 5, 10, 15, 20, 25 contiguous nucleotides.

A region, portion, or sequence which is "adjacent" to another sequence directly abuts that region, portion, or sequence. For example, an RNA portion which is adjacent to a 5' DNA portion of a composite primer directly abuts that region. For an illustration of this example, see FIGS. 1A and 2A.

A "reaction mixture" is an assemblage of components, which, under suitable conditions, react to form a complex (which may be an intermediate) and/or a product(s).

"A", "an" and "the", and the like, unless otherwise indicated include plural forms. "A" fragment means one or more fragments.

"Comprising" means including.

Conditions that "allow" an event to occur or conditions that are "suitable" for an event to occur, such as hybridization, strand extension, and the like, or "suitable" conditions are conditions that do not prevent such events from occurring. Thus, these conditions permit, enhance, facilitate, and/or are conducive to the event. Such conditions, known in the art and described herein, depend upon, for example, the nature of the nucleotide sequence, temperature, and buffer conditions. These conditions also depend on what event is desired, such as hybridization, cleavage, strand extension or transcription.

Sequence "mutation," as used herein, refers to any sequence alteration in a sequence of interest in comparison to a reference sequence. A reference sequence can be a wild type sequence or a sequence to which one wishes to compare a sequence of interest. A sequence mutation includes single nucleotide changes, or alterations of more than one nucleotide in a sequence, due to mechanisms such as substitution, transversion, deletion or insertion. Single nucleotide polymorphism (SNP) is also a sequence mutation as used herein.

"Single stranded conformation polymorphism," and "SSCP," as used herein, generally refer to the specific conformation of a single stranded nucleic acid as is affected by its specific nucleic acid sequence. Alteration of the sequence of the single stranded polynucleotide, such as single nucleotide substitution, deletions or insertions, result in change, or polymorphism, of the conformation of the single stranded polynucleotide. The conformation of the polynucleotide is generally detectable, identifiable and/or distinguishable using methods known in the art, such as electrophoretic mobility as measured by gel electrophoresis, capillary electrophoresis, and/or susceptibility to endonuclease digestion.

"Microarray" and "array," as used interchangeably herein, comprise a surface with an array, preferably ordered array, of putative binding (e.g., by hybridization) sites for a biochemical sample (target) which often has undetermined characteristics. In a preferred embodiment, a microarray refers to an assembly of distinct polynucleotide or oligonucleotide probes immobilized at defined positions on a substrate. Arrays are formed on substrates fabricated with materials such as paper, glass, plastic (e.g., polypropylene, nylon, polystyrene), polyacrylamide, nitrocellulose, silicon, optical fiber or any other suitable solid or semi-solid support, and configured in a planar (e.g., glass plates, silicon chips) or three-dimensional (e.g., pins, fibers, beads, particles, microtiter wells, capillaries) configuration. Probes forming the arrays may be attached to the substrate by any number of ways including (i) in situ synthesis (e.g., high-density oligonucleotide arrays) using photolithographic techniques (see, Fodor et al., *Science* (1991), 251:767-773; Pease et al., *Proc. Natl. Acad. Sci. U.S.A.* (1994), 91:5022-5026; Lockhart et al., *Nature Biotechnology* (1996), 14:1675; U.S. Pat. Nos. 5,578, 832; 5,556,752; and 5,510,270); (ii) spotting/printing at medium to low-density (e.g., cDNA probes) on glass, nylon or nitrocellulose (Schena et al, Science (1995), 270:467-470, DeRisi et al, *Nature Genetics* (1996), 14:457-460; Shalon et al., *Genome Res.* (1996), 6:639-645; and Schena et al., *Proc. Natl. Acad. Sci. U.S.A.* (1995), 93:10539-11286); (iii) by masking (Maskos and Southern, *Nuc. Acids. Res.* (1992), 20:1679-1684) and (iv) by dot-blotting on a nylon or nitrocellulose hybridization membrane (see, e.g., Sambrook et al., Eds., 1989, Molecular Cloning: A Laboratory Manual, 2nd ed., Vol. 1-3, Cold Spring Harbor Laboratory (Cold Spring Harbor, N.Y.)). Probes may also be noncovalently immobilized on the substrate by hybridization to anchors, by means of magnetic beads, or in a fluid phase such as in microtiter wells or capillaries. The probe molecules are generally nucleic acids such as DNA, RNA, PNA, and cDNA but may also include proteins, polypeptides, oligosaccharides, cells, tissues and any permutations thereof which can specifically bind the target molecules.

The term "3'" generally refers to a region or position in a polynucleotide or oligonucleotide 3' (downstream) from another region or position in the same polynucleotide or oligonucleotide.

The term "5'" generally refers to a region or position in a polynucleotide or oligonucleotide 5' (upstream) from another region or position in the same polynucleotide or oligonucleotide.

The term "3'-DNA portion," "3'-DNA region," "3'-RNA portion," and "3'-RNA region," refer to the portion or region of a polynucleotide or oligonucleotide located towards the 3' end of the polynucleotide or oligonucleotide, and may or may not include the 3' most nucleotide(s) or moieties attached to the 3' most nucleotide of the same polynucleotide or oligonucleotide. The 3' most nucleotide(s) can be preferably from about 1 to about 50, more preferably from about 10 to about 40, even more preferably from about 20 to about 30 nucleotides.

The term "5'-DNA portion," "5'-DNA region," "5'-RNA portion," and "5'-RNA region," refer to the portion or region of a polynucleotide or oligonucleotide located towards the 5' end of the polynucleotide or oligonucleotide, and may or may not include the 5' most nucleotide(s) or moieties attached to the 5' most nucleotide of the same polynucleotide or oligonucleotide. The 5' most nucleotide(s) can be preferably from about 1 to about 50, more preferably from about 10 to about 40, even more preferably from about 20 to about 30 nucleotides.

As is well understood by those skilled in the art, a "tail" sequence of a primer is a sequence not hybridizable to the target sequence under conditions in which other region(s) or portion(s) of the primer hybridizes to the target.

"Absent" or "absence" of product, and "lack of detection of product" as used herein includes insignificant, or de minimus levels, generally due to lack of significant accumulation of product due to cycling.

Amplification Methods of the Invention

The following are examples of the amplification methods of the invention. It is understood that various other embodiments may be practiced, given the general description provided above. For example, reference to using a composite primer means that any of the composite primers described herein may be used.

In one aspect of the invention, a method for generating multiple copies (amplifying) of a polynucleotide (DNA) sequence complementary to an RNA sequence of interest using a composite primer and a second primer is provided. In this method, isothermal linear nucleic acid sequence amplification is achieved using two primers (a composite primer and a second primer) and strand displacement. In some embodiments, a transcription step is included (i.e., an "enhanced" method), and amplified product in the form of sense RNA is produced.

In another aspect of the invention, a method for generating multiple copies (amplifying) of a DNA sequence complementary to an RNA sequence of interest using a single primer (which is a composite primer) is provided. In this method, isothermal linear nucleic acid amplification is achieved using a single composite primer, a fragment of target RNA (which serves as an endogenous primer), and strand displacement. In some embodiments, a transcription step is included (i.e., the "enhanced" method), and amplified product in the form of sense RNA is produced.

As described herein, the amplification methods of the invention may further include a transcription step. If a primer extension product that is to be transcribed comprises a propromoter sequence, a double stranded promoter region is generally generated by hybridizing a polynucleotide comprising a propromoter (also referred to herein as "propromoter polynucleotide") to the primer extension product. If a primer extension product does not comprise a desired propromoter sequence, the transcription step is generally dependent on the incorporation of an RNA polymerase propromoter sequence, by use of a propromoter polynucleotide such as a promoter sequence oligonucleotide (PTO). A propromoter polynucleotide such as the PTO can serve as a template for extension of a single stranded primer extension product and formation of a partial duplex comprising a double stranded promoter at one end. The ability to hybridize the single stranded product to the propromoter polynucleotide (such as a PTO) is generally achieved by creating a primer extension product with a defined 3' end sequence, which is complementary to the 3' end sequence of the propromoter polynucleotide. One aspect of the methods of the invention includes the design of primers which are able to hybridize to RNA sequences, such as a plurality of RNA sequences, for initiation of primer extension and production of amplification substrates and products.

Linear Nucleic Acid Sequence Amplification Using a Composite Primer and a Second Primer The invention provides methods of amplifying an RNA sequence of interest by using a composite primer and a second primer, and strand displacement. Amplification by these methods is linear and can be achieved isothermally. In embodiments that do not include a transcription step, amplified products are single stranded DNA comprising sequences complementary to the RNA sequence of interest in the target RNA. In embodiments that include transcription, amplified products are sense RNA copies of the RNA sequence of interest in the target RNA.

Figure 1B:
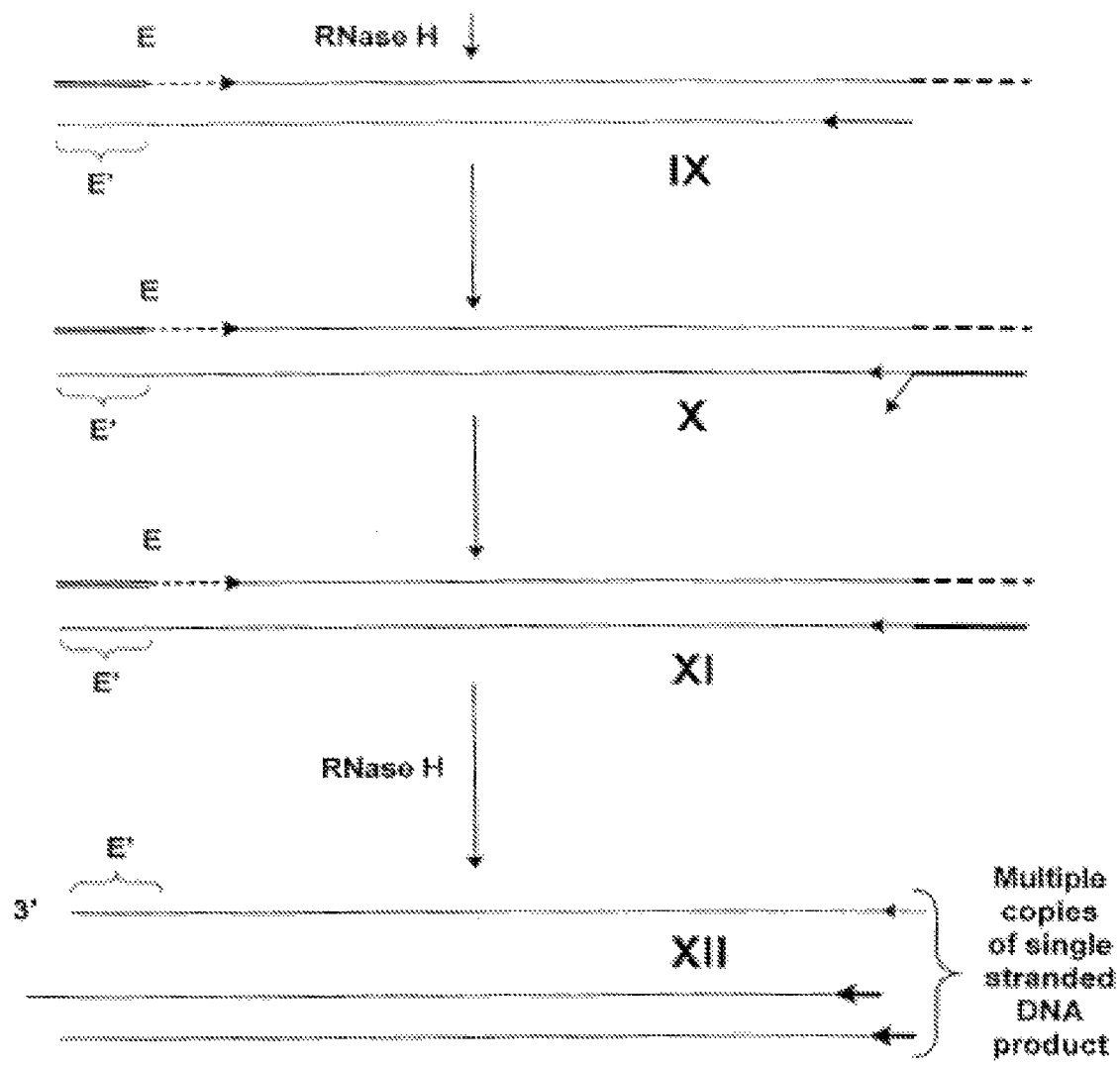
Figure 2A:
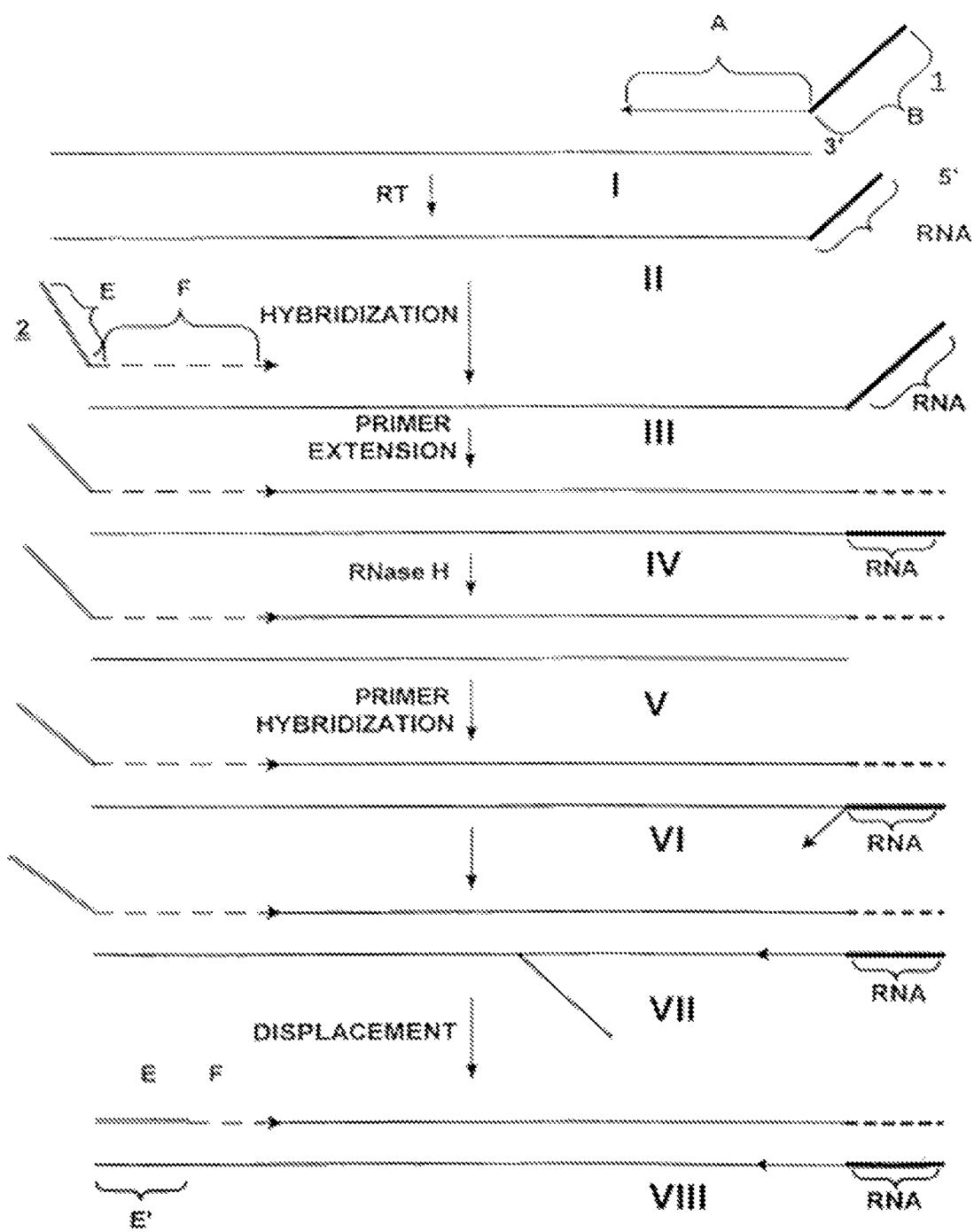
FIGS. 2A-C show a diagrammatic representation of an enhanced linear isothermal RNA amplification process using a composite primer, a second primer, strand displacement and transcription to generate multiple copies of the target RNA.
Figure 2B:
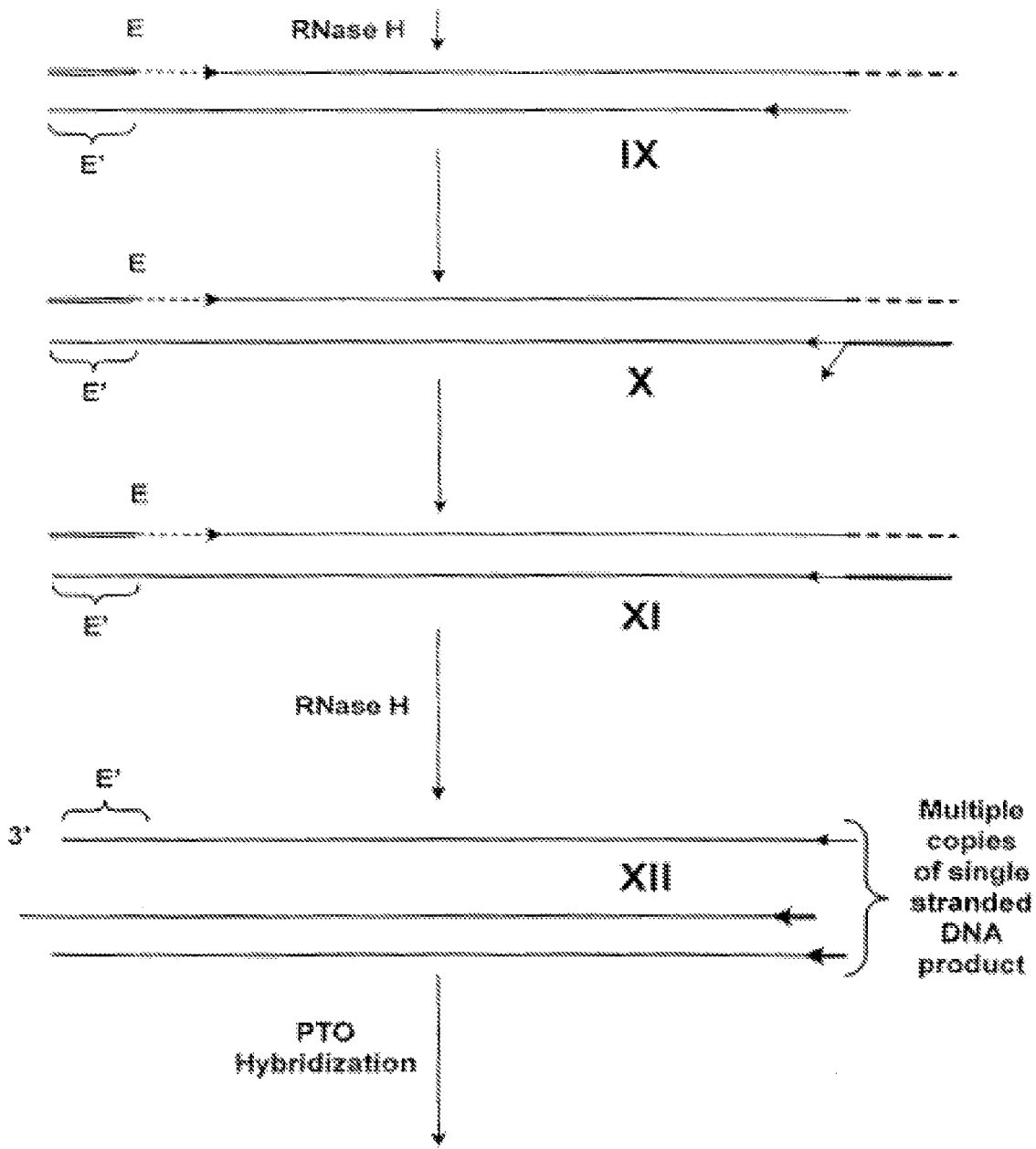
Figure 2C:
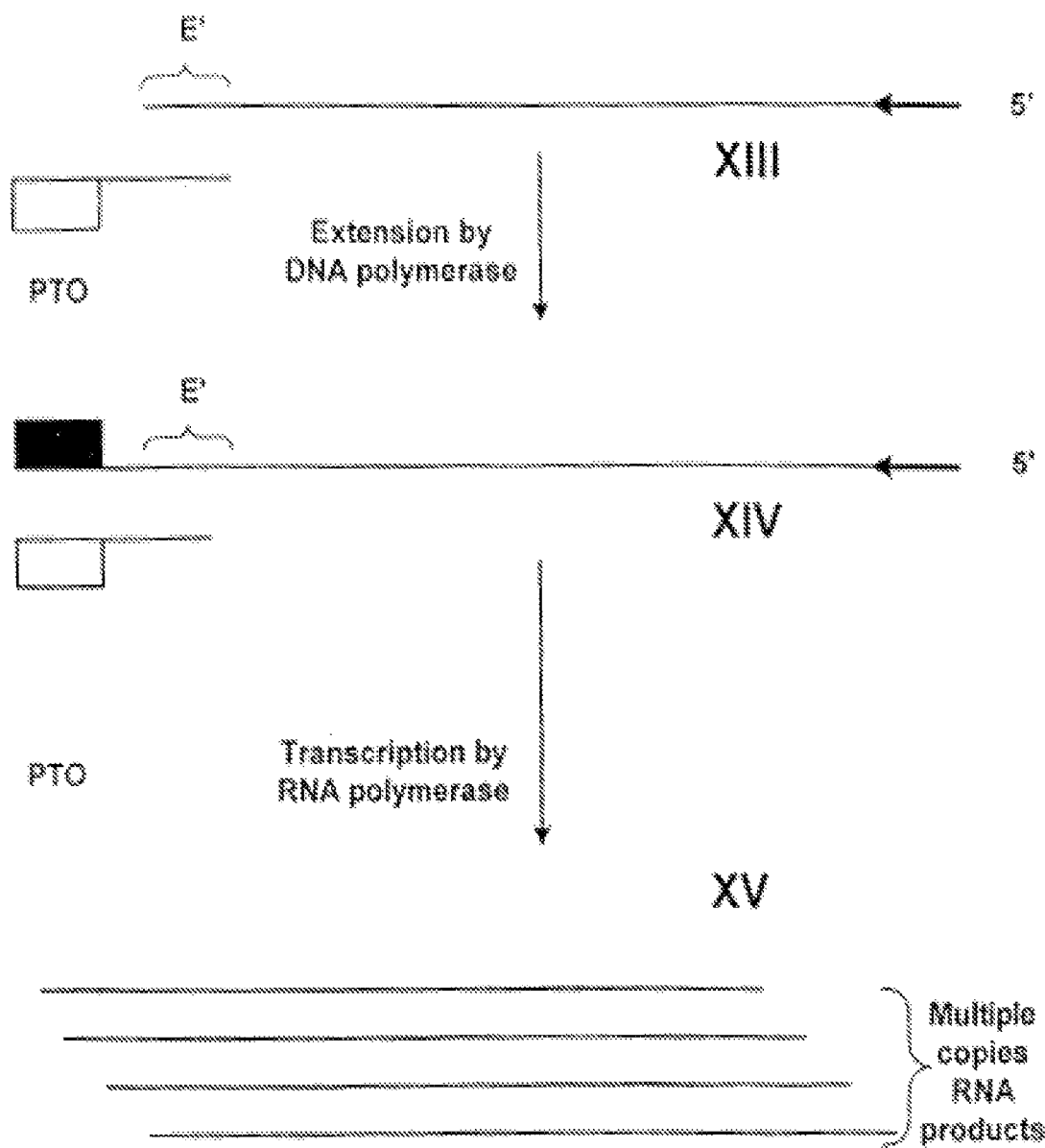

A schematic description of one embodiment of the composite primer, second primer and strand displacement-based methods of the invention is given in FIGS. 1A-B and 2A-C. FIGS. 1A-B illustrate a non-enhanced linear method. FIGS. 2A-C illustrate an enhanced (i.e., including a transcription step) method. The methods involve the following steps: (a) formation of a second strand cDNA which is the same sense as the input RNA; (b) linear amplification of the complement of a second strand cDNA strand by primer extension (from a composite primer) along the second strand cDNA and strand displacement; and, in the enhanced method, (c) transcription of the product of the linear amplification step to produce multiple copies of sense RNA products. As illustrated, all steps are isothermal, although the temperatures for each of the steps may or may not be the same.

The embodiment illustrated in FIGS. 1A-B employs two oligonucleotides: a composite primer, (labeled 1), used for the amplification; and a second primer (labeled 2), used for the formation of the sense complement DNA (cDNA) (interchangeably called "second primer extension product" or "second strand cDNA). The embodiment illustrated in FIGS. 2A-C employs three oligonucleotides: a composite primer, (labeled 1), used for the amplification; a second primer (labeled 2), used for the formation of the second strand (sense) cDNA; and a polynucleotide comprising a propromoter sequence of a DNA-dependent RNA polymerase, i.e., a promoter template oligonucleotide (PTO) (labeled 3).

The 3' portion of the composite primer can be designed in any of a number of ways (in terms of sequence), depending on which type, class, population, and/or species of RNA is desired to be amplified. In some embodiments, the 3' portion of composite primer 1, as illustrated in FIGS. 1 and 2, comprises a sequence complementary to the poly-A tail of mRNA, and may further comprise additional random sequences (generally not complementary to a poly-A sequence) at the 3' end of the 3' portion. In other embodiments, the 3' portion of composite primer 1 is a random primer comprising sequences which are hybridizable to a multiplicity of RNA species (which may range from 2 or more to many hundred or thousands or more). Random primers are known in the art, for example, they have been used extensively in the preparation of cDNA libraries using PCR-based procedures. As is well understood in the art, a "random primer" can refer to a primer that is a member of a population of primers (a plurality of random primers) which collectively are designed to hybridize to a desired and/or a significant number of target sequences. A random primer may hybridize at a plurality of sites on a nucleic acid sequence.

In other embodiments, the 3' portion of composite primer 1 can comprise a sequence complementary or hybridizable to a specific RNA or family of RNAs (or portions thereof).

In some embodiments as illustrated in FIGS. 1 and 2, the 5' portion of composite primer 1 can be a sequence not hybridizable to the target sequence (under conditions in which the 3' portion hybridizes to RNA target), e.g., a sequence forming a "tail" when the primer is hybridized to a target. This "tail" sequence generally is incorporated into the first primer extension product (first strand cDNA), and the complement of this tail will be incorporated at the 3' end of the second primer extension product (second strand cDNA). Accordingly, in some embodiments, composite primer 1 is a mixtures of composite primers which comprise the same 5' RNA portion and a multiplicity of 3' DNA portions selected to amplify a multiplicity (which can be small to very large) of RNA sequences of interest. In other embodiments, the 5' portion of the composite primer 1 can be hybridizable to the target RNA. Although FIGS. 1 and 2 depict a 3' portion hybridized to the target sequence that is a DNA portion and a 5' portion non hybridized to the target that is an RNA portion, it is understood that DNA portions can comprise part of a "tail" and conversely that RNA portions can be hybridizable to target RNA. For example, the 5' RNA portion of a composite primer may be partially hybridizable and partially nonhybridizable, or the DNA portion of a composite primer may be partially hybridizable and partially nonhybridizable, or both.

As illustrated in these figures, the composite primer 1 comprises a DNA portion, A, at its 3' end, and an RNA portion, B, at its 5' end. As discussed herein, it is also possible to employ a composite primer in which the 3' DNA portion is followed, in the direction of its 5', by an RNA portion, which is followed by a portion which is DNA. The length of each of these sections is generally determined for maximum efficiency of the amplification. Only the two-portion (i.e., 3'-DNA-RNA-5') composite primer is shown in FIGS. 1A-B and FIGS. 2A-C.

Primer 2 as illustrated in FIGS. 1A-B and 2A-C can be, but is not necessarily, composed of DNA and can comprise two sections (interchangeably called "portions" or "regions"). The 3' portion, F, of primer 2 can be selected for random priming of many, most and/or all possible mRNA sequences in a biological sample. Random primers are known in the art, for example, they have been used extensively in the preparation of cDNA libraries using PCR-based procedures. The 5' portion, E, of primer 2 can be a sequence which is not complementary and not substantially hybridizable to a specific target sequence, i.e., it would not hybridize (under conditions in which the 3' portion hybridizes to RNA target) and would constitute a tail. The "tail" sequence would generally be incorporated into the second primer extension product, and the 3' end sequence of the DNA product of the linear amplification steps would generally comprise the complement of this sequence. In other embodiments, if enhanced amplification is not desired (as described below), the 5' end portion, E, of primer 2 can be hybridizable to the target sequence in the first primer extension product.

As illustrated in FIGS. 2A-C, a promoter template oligonucleotide, 3 (PTO), can be designed as follows: the 3' portion is the same as portion E of primer 2. This design enables the PTO to hybridize to the 3' end of the linear amplification product. The 5'-most portion of the PTO is a promoter sequence for a DNA-dependent RNA polymerase, which, as described above, is used in certain (namely, the "enhanced" method) embodiments of the amplification methods of the invention. Generally, the sequence between these two sections is designed for optimal transcription by the polymerase of choice. Criteria for selection and design of this sequence are known in the art.

For convenience, only one first primer extension product (first strand cDNA) and second strand primer extension product (second strand cDNA) are described and illustrated in FIGS. 1 and 2. It is understood that the methods of the invention are useful not only for producing large amounts of one specific nucleic acid sequence, but also for amplifying simultaneously more than one different specific nucleic acid sequence located on the same or different target nucleic acid molecules. For example, the methods of the invention are useful for amplifying all mRNA in a sample, or for amplifying a multiplicity of specific RNA species or family of RNA species in a sample.

As illustrated in FIGS. 1A-B, in one embodiment, the process of the amplification methods of the invention resulting in generation of DNA products comprising sequences complementary to an RNA sequence(s) of interest based on RNA is as follows:

A) Formation of a Double Stranded cDNA Substrate for Linear Amplification

1. Primer 1 binds to an RNA species in a sample by hybridization of the random sequence portion A (which can be based at least in part on the poly-A sequence of the mRNA), to form complex I (FIG. 1A).
2. A reverse transcriptase, (indicated as "RT"), extends the hybridized primer 1 along the target RNA strand to which it is hybridized, to form an RNA/DNA duplex. RNase H degrades the target RNA strand of the hybrid duplex to generate a single stranded first strand cDNA (labeled "II"). The 5' end of II is primer 1.
3. Primer 2 binds to first strand cDNA, II, by hybridization of sequence F, to form complex III.
4. Primer 2 is extended along the cDNA strand II by a DNA polymerase to form a double stranded product (labeled "IV"). Primer extension along the 5' RNA portion of II by an RNA-dependent DNA polymerase such as a reverse transcriptase results in formation of an RNA/DNA hybrid portion at one end of complex IV.
5. RNase H degrades the RNA portion of the RNA/DNA hybrid at one end of complex IV, to create a partial double stranded complex (labeled "V") with a 3' DNA single stranded end, which has a sequence which is the complement of portion B of the composite primer 1. The RNase H activity may be supplied by the RNA-dependent DNA polymerase (such as reverse transcriptase) or may be provided in a separate enzyme. Reverse transcriptases useful for this method may or may not have RNase H activity.

B) Isothermal Linear Amplification

1. Primer 1 binds to complex V by hybridization of the RNA portion, B, to the single stranded DNA end, which is complementary to it, to form complex VI. The 3' DNA sequence of primer 1 is not hybridized.
2. The 3' end of bound primer 1 in complex VI, and the 5' end of the DNA strand immediately upstream are the same, and would compete for hybridization to the opposite strand. Without wishing to be bound by theory, the high affinity of the DNA polymerase to hybridized 3' end of a primer would be expected to push the equilibrium of the two competing structures towards hybridization of the 3' end of the new primer and displacement of the 5' end of the previous primer extension product (labeled "VII"). Primer extension along the second strand (sense) cDNA strand results in displacement of the previous second primer extension product (VII), and replicates the E sequence of primer 2, to form complex VIII.

3. Complex VIII has, at one end, an RNAJDNA hybrid composed of sequence B and its complement. The RNA segment of the hybrid is degraded by RNase H, to form complex IX, which results in the formation of a single stranded 3' end to which a new primer 1 can be bound by its 5' B portion.

4. The process of hybridization of the 3' end sequence A of the bound primer 1, by displacement of the 5'-most end of the previous primer extension product in the duplex, primer extension and displacement of the previous product continues as shown in FIGS. 1A-B, and results in the accumulation of multiple copies of anti-sense single stranded DNA products (labeled "XII"). These products have at their 3' ends a sequence complementary to portion E of primer 2, and at their 5' ends a sequence substantially identical (generally, identical) to sequence A of the composite primer. Kurn, U.S. Pat. No. 6,251,639 B1.

One embodiment of the enhanced method is illustrated in FIGS. 2A-C. In this embodiment, subsequent to the generation of DNA product comprising complementary sequences of an RNA sequence of interest, the following steps are performed.

C) Transcription of the DNA Products

1. A PTO (see FIG. 2C), binds to DNA product XII by hybridization of its 3' end sequence to the 3' end sequence of DNA product XII to form complex XIII. The 3' end of the PTO is preferably, but not necessarily, blocked so that it cannot be extended by a DNA polymerase.

2. DNA polymerase extends the 3' end of product XII in complex XIII, along the PTO template to form complex XIV comprising a double stranded promoter sequence at one end.

3. DNA-dependent RNA polymerase binds to the double stranded promoter in complex XIV to transcribe the antisense single stranded DNA product to yield multiple copies of sense RNA products (labeled "XV"). Multiple species of product XV would represent multiple copies of multiple sequences from a pool of input RNA. Kurn, U.S. Pat. No. 6,251,639 B1.

The methods of the invention may be used for generation of multiple copies of a plurality of RNA sequences in the sample. For example, the composite primer can comprise a poly-dT sequence, which would be expected to hybridize to the poly-A tails of all mRNA is a sample, or the composite primer can generally comprise at least a 3' portion that is hybridizable to random or partially random sequences (e.g. comprising a poly-dT sequence and a random sequence, which would be expected to hybridize to the beginning of the poly-A tails of mRNAs). In another aspect, the methods of the invention may be used for generation of multiple copies of a specific RNA species or class of RNA species (e.g., a family or superfamily of RNA species). In this latter case, the composite primer generally comprises a 3'-portion which is complementary to a sequence of a specific RNA target (or family of RNA targets).

The 5'-RNA portion of the composite primer may or may not be related to the specific RNA target sequence, and may or may not hybridize to the RNA target, for example, it may form a tail as further described herein.

Although only one composite primer is described in the embodiments above, it is understood that a different composite primer may be used in step (b), above. The different composite primer comprises sequences hybridizable to the single stranded DNA portion of the complex IX, described above. The second composite primer may further comprise sequences hybridizable to a portion of the second primer extension product sequences immediately 5' to the single stranded DNA portion of complex IX. The second composite primer generally comprises overlapping sequences with the first composite primer. The second composite primer is hybridized to the second primer extension product and extended by primer extension. Cleavage of the DNA-RNA heteroduplex by RNAse permits binding of another second composite primer, extension and strand displacement, whereby multiple copies of the single stranded product are produced.

For convenience, only one first primer extension product (first strand cDNA) and second strand primer extension product (second strand cDNA) are described and illustrated in FIGS. 1 and 2. It is understood that the methods of the invention are useful not only for producing large amounts of one specific nucleic acid sequence, but also for amplifying simultaneously more than one different specific nucleic acid sequence located on the same or different target nucleic acid molecules. For example, the methods of the invention are useful for amplifying all mRNA in a sample, or for amplifying a multiplicity of specific RNA species (in which case a multiplicity of first composite primer each comprising a 3' portion hybridizable to specific sequences of specific RNA species could be used) or family of RNA species in a sample. Linear Nucleic Acid Sequence Amplification Using a Single Composite Primer and a Target RNA Fragment The invention also provides methods of amplifying an RNA sequence of interest by using a single primer (which is a composite primer), a target RNA fragment, and strand displacement. Amplification by these methods is linear and can be achieved isothermally. In embodiments that do not include a transcription step, amplified products are DNA comprising sequences complementary to the RNA sequence of interest in the target RNA. In embodiments that include transcription, amplified products are sense RNA copies of the RNA sequence of interest in the target RNA.

Figure 3A:
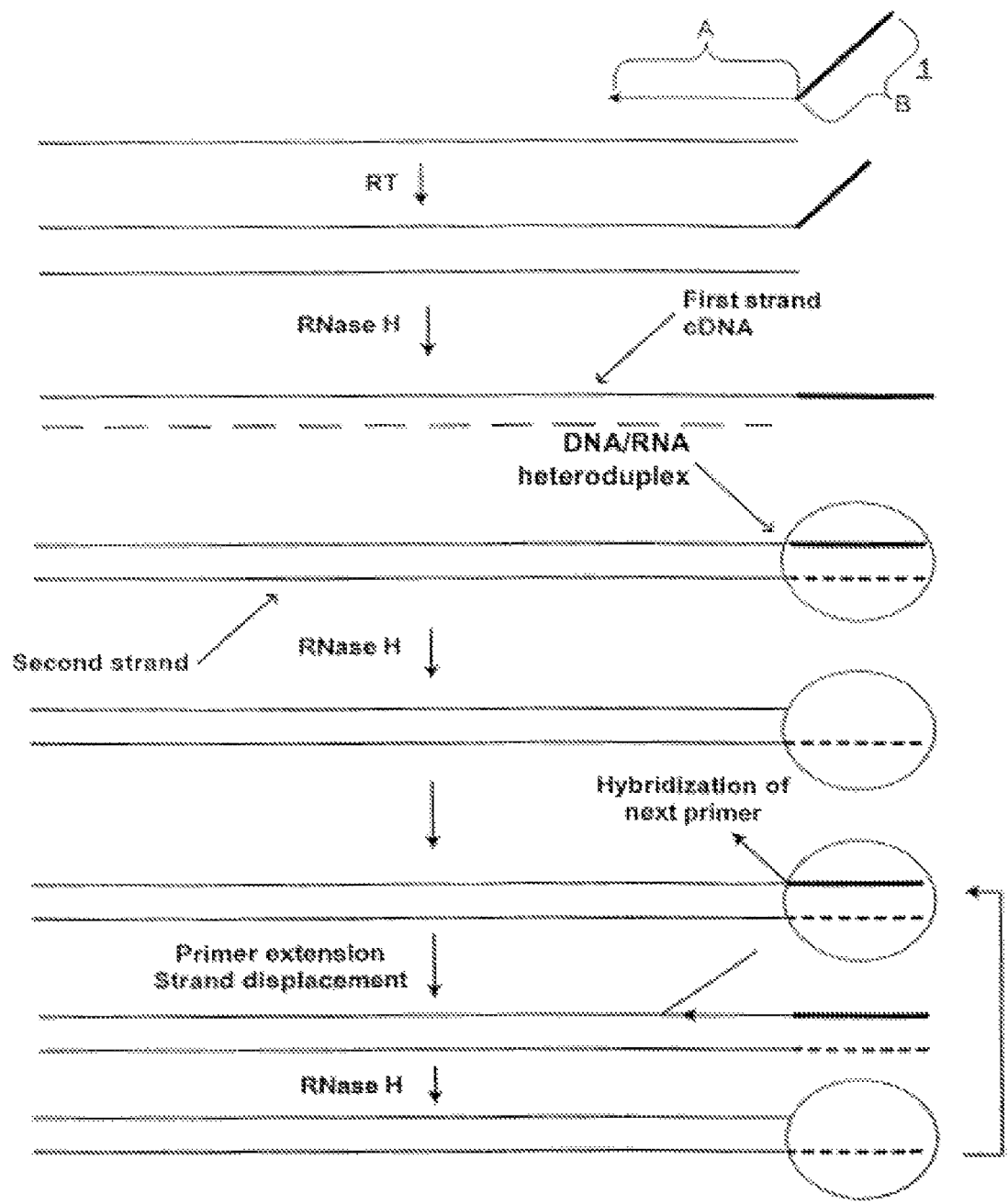
FIGS. 3A-B show a diagrammatic representation of a linear isothermal RNA amplification process using a single composite primer and strand displacement to generate multiple copies of single stranded DNA product comprising sequences complementary to the target RNA.
Figure 3B:
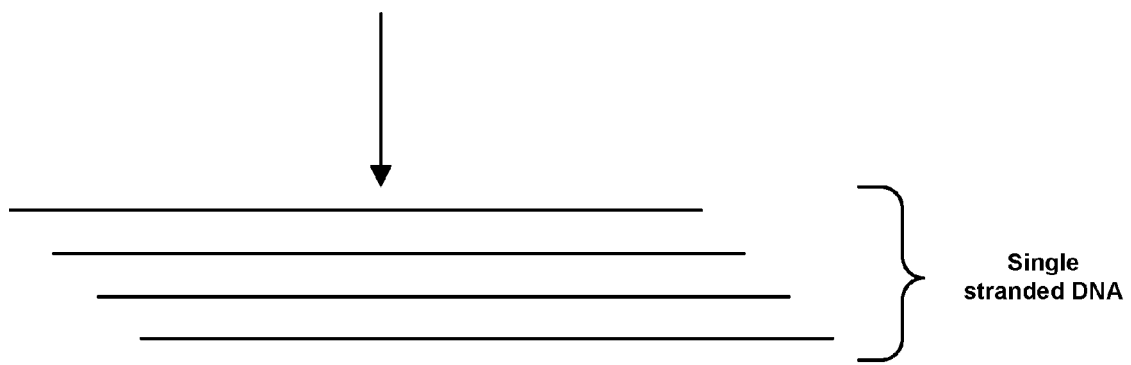

A schematic description of a non-enhanced (linear) embodiment of the single composite primer and strand displacement-based methods of the invention is provided in FIGS. 3A-B. The method involves the following steps: (a) primer extension to form an RNA/DNA heteroduplex of a target RNA and a first strand cDNA; (b) incomplete degradation of the RNA target of the heteroduplex to form a complex of the first strand cDNA and at least one RNA fragment that can in turn serve as a primer; (c) formation of a second strand cDNA that is of the same sense as the input target RNA; (d) linear amplification of the complement of a second strand DNA by primer extension (from a composite primer) along the second strand cDNA and strand displacement to produce multiple copies of antisense single stranded DNA products. As illustrated, all steps are isothermal, although the temperatures for each of the steps may or may not be the same. A schematic description of an embodiment of enhanced single composite primer and strand displacement-based methods of the invention is provided in FIGS. 4A-B. The method involves the following steps: (a) primer extension to form an RNA/DNA heteroduplex of a target RNA and a first strand cDNA; (b) incomplete degradation of the RNA target of the heteroduplex to form a complex of the first strand cDNA and at least one RNA fragment that can in turn serve as a primer; (c) formation of a second strand cDNA that is of the same sense as the input target RNA; (d) linear amplification of the complement of a second strand DNA by primer extension (from a composite primer) along the second strand cDNA and strand displacement to produce multiple copies of antisense single stranded DNA products; and (e) transcription of the product of the linear amplification step to produce multiple copies of sense RNA products.

Figure 4A:
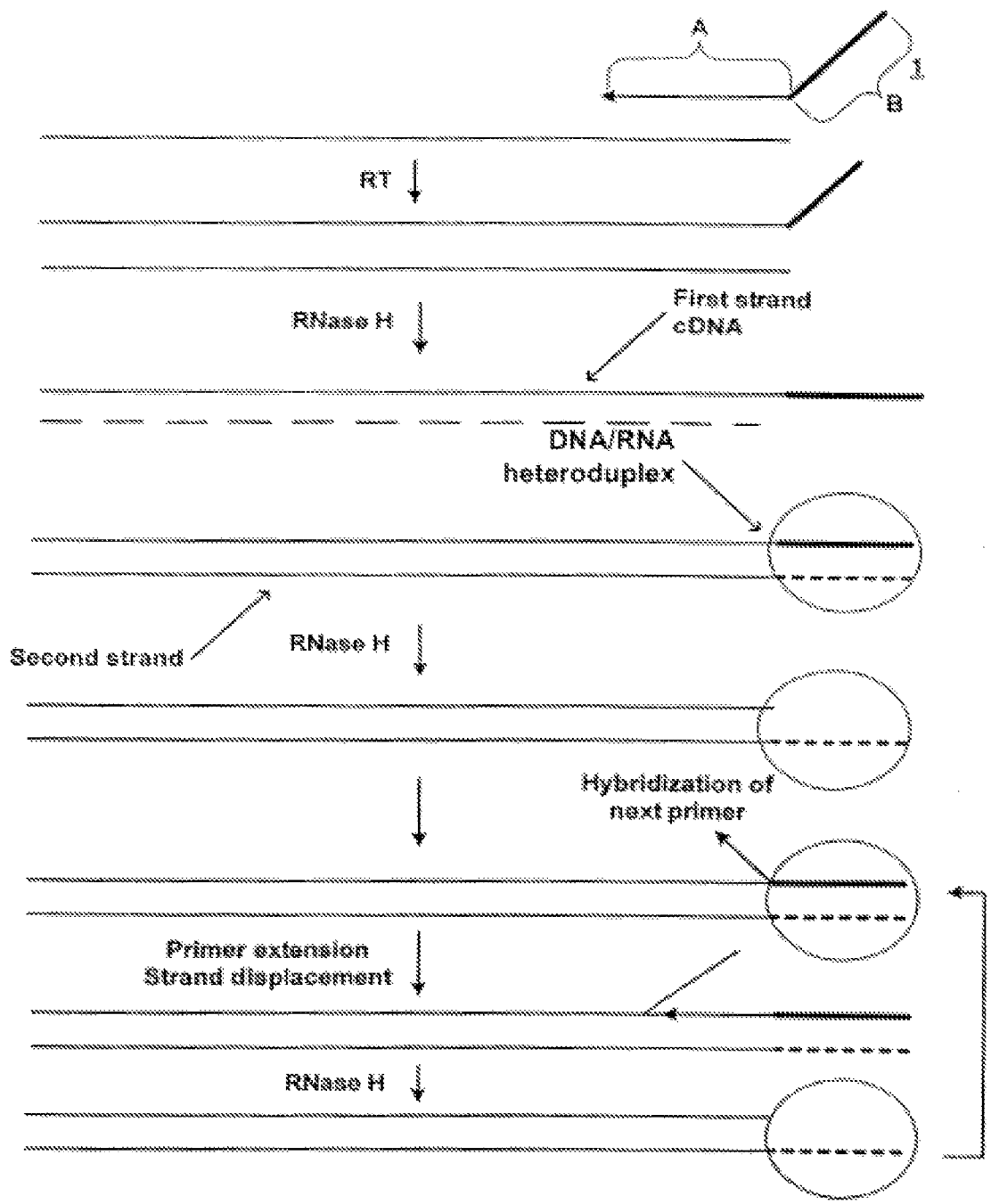
FIGS. 4A-B show a diagrammatic representation of an enhanced linear isothermal RNA amplification process using a single composite primer, strand displacement and transcription to generate multiple copies of the target RNA.

A composite primer, as described herein, is used for the amplification in these methods. As illustrated in FIGS. 3A and 4A, the single (composite) primer (labeled "1") can be composed of a 3'-DNA portion (labeled "A") which is complementary to a sequence on the target RNA, and a 5'-RNA portion (labeled "B") which comprises a non-target related sequence (i.e., it is not complementary/hybridizable (under a given set of conditions) to a sequence on the target RNA). The 3'-DNA portion of the composite primer may comprise poly-dT nucleotides, which would render it complementary/hybridizable (under a given set of conditions) to the poly-A 3' end of mRNA derived from a eukaryotic cell.

A composite primer that is hybridized to a target RNA is extended by an RNA-dependent DNA polymerase, such as a reverse transcriptase, to form an RNA/DNA heteroduplex of the target RNA and a first strand cDNA. Degradation of the target RNA of the heteroduplex is then achieved using a ribonuclease such as RNase H, to form a complex of the first strand cDNA and one or more RNA fragments (oligonucleotides). The RNase H activity may be supplied by the RNA-dependent DNA polymerase (such as reverse transcriptase) or may be provided in a separate enzyme. Reverse transcriptases useful for this method may or may not have RNase H activity. The fragments are a result of incomplete degradation of the target RNA in the heteroduplex. These fragments function as primers for a DNA-dependent DNA polymerase to form the second strand cDNA. Okayama & Berg, *Molecular and Cell Biology* (1982), 2:161; and Gubler & Hoffman, *Gene* (1983), 25:263. Reverse transcriptase then extends the 3'-end of the second strand cDNA in the duplex along the 5'-RNA sequence of the composite primer extension product (the first strand cDNA), to form an RNA/DNA heteroduplex at the end of the double stranded cDNA product.

The heteroduplex at the end of the double stranded cDNA is a substrate for RNase H. The RNase H degrades the 5'-RNA portion of the first strand cDNA, to create a site for hybridization of the composite primer, which hybridizes by its 5'-RNA portion to the 3'-end of the second strand cDNA in the duplex cDNA. The 3' DNA portion of the new primer displaces the 5' end of the first strand cDNA, by hybridization to its complementary sequence on the second strand cDNA. A DNA polymerase with strong strand displacement activity then extends the new primer along the second strand cDNA, and displaces the previously formed cDNA product. An RNase H degrades the 5'-portion of the new primer extension product in the heteroduplex, to create a free site for hybridization of a new composite primer, thus resulting in continuous linear amplification of the target sequence and generation of multiple copies of single stranded DNA product which is anti sense to the target RNA sequence.

Figure 4B:
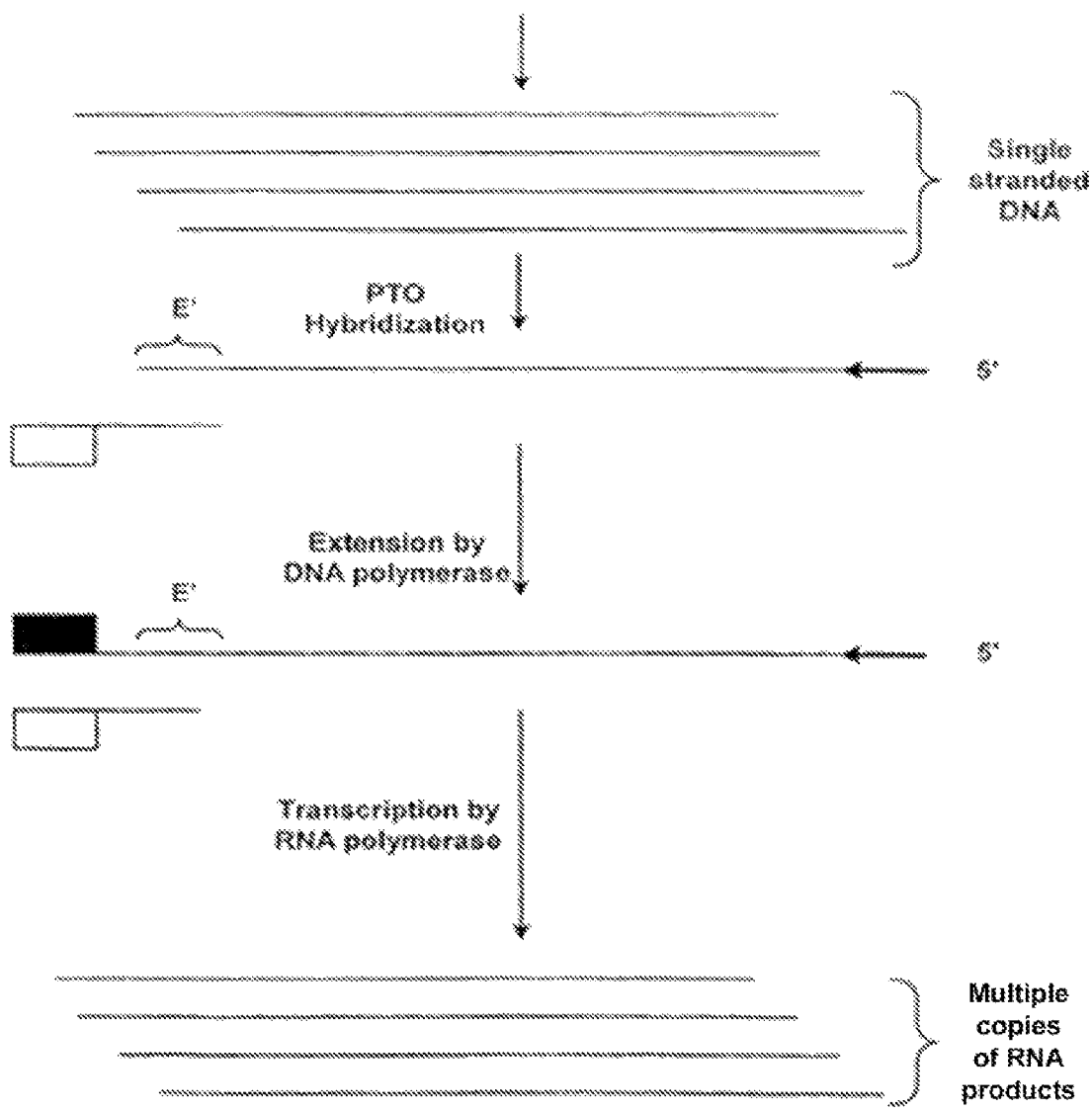

As depicted in FIGS. 4A-B, and as is evident from the description herein, the single composite primer amplification methods can also include a transcription step employing a propromoter polynucleotide in the same manner as that described with respect to the enhanced methods of amplification using a composite primer and a second primer.

The methods of the invention may be used for generation of multiple copies of a plurality of RNA sequences in the sample or of a specific RNA species or group of species. In the latter cases, the composite primer generally comprises a 3'-portion which is complementary and/or hybridizable to a sequence of a specific RNA target or group of targets (e.g., homologous RNA targets or targets that are members of a family or superfamily of sequences). For example, the primer may comprise a collection of primer sequences, such as where more than one target sequence exists.

Another application of the methods of the invention is in detection of variant regions flanking a common sequence. By designing a first composite primer that recognizes a commonly shared sequence, single stranded DNA or RNA product is produced that contains not only the common region recognized by the primer, but also 5'-flanking sequence useful in detecting sequence variants. Thus, for example, single stranded DNA or RNA product can be produced from limited amounts of clinical material to allow pathogen-specific sequences (such as those distinguishing viral types) to be identified, genetic polymorphisms to be detected, or alternate splicing variants to be characterized, all in accordance with standard techniques. In other embodiments, single stranded DNA or RNA product is produced that contains not only the common region recognized by the primer, e.g., a conserved or functional sequence motif, but also 5'-flanking sequences permitting identification of groups of RNA species comprising similar sequence motifs.

The 5'-RNA portion of the composite primer may or may not be related to the specific RNA target sequence, and may or may not hybridize to the RNA target. Methods of the invention using "tailed" composite primers are described further herein.

Figure 5A:
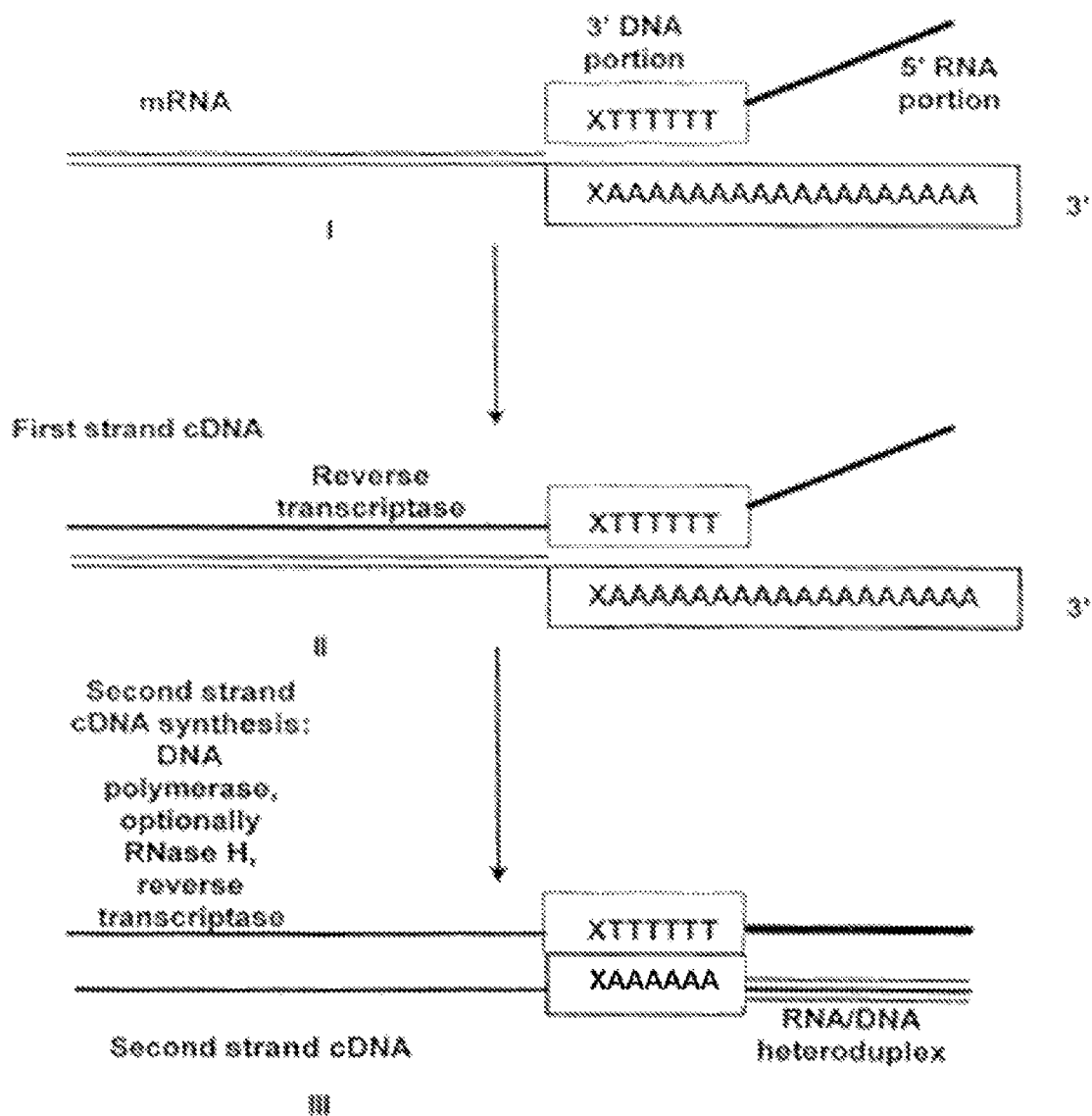
FIGS. 5A-B shows a diagrammatic representation of a linear isothermal RNA amplification process using a single composite primer containing a poly-dT sequence and strand displacement to generate multiple copies of single stranded DNA product comprising sequences complementary to the target RNA.
Figure 5B:
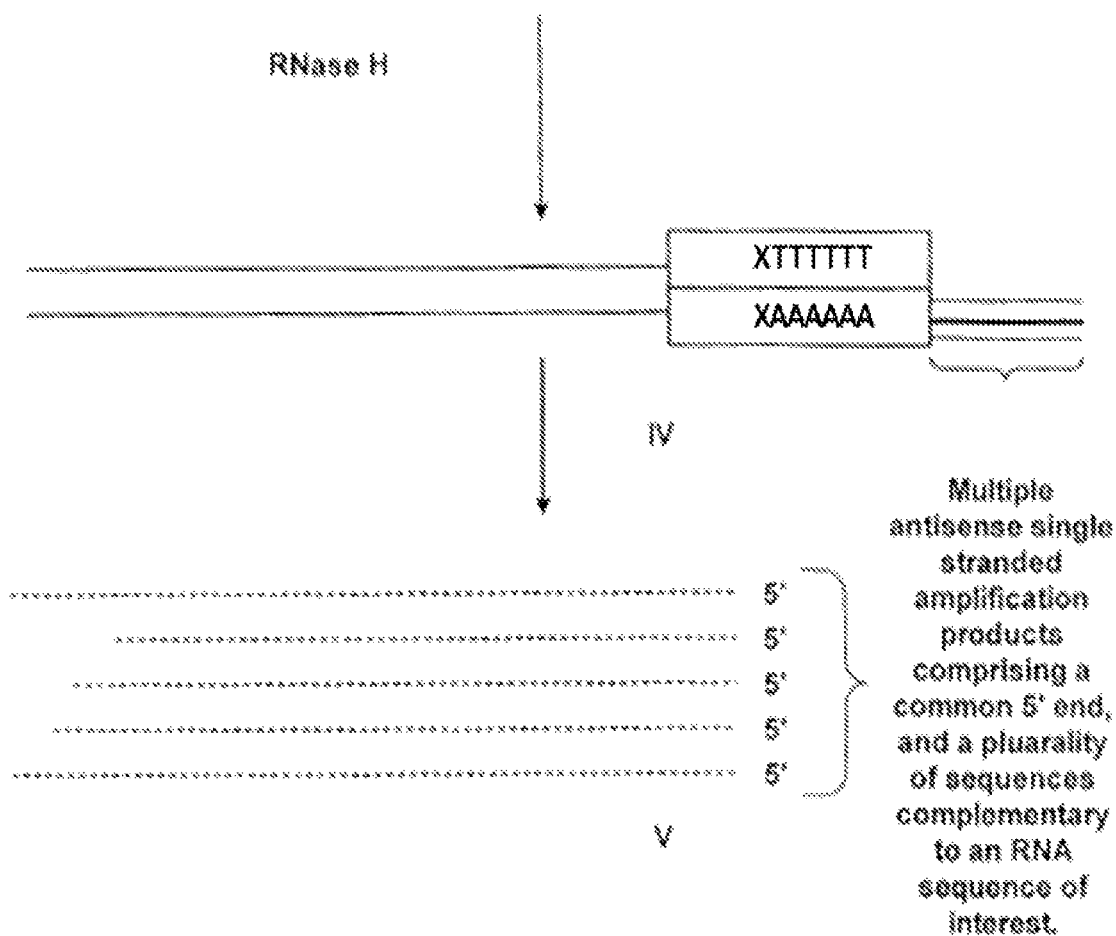

Linear mRNA Amplification Using a Single Composite Primer and a Target RNA Fragment As is described herein, total mRNA may be amplified using a composite primer comprising a poly(T) of sufficient length to hybridize with substantially an entire population of messages (i.e., poly(T)n, wherein n is typically from about 5 to 50 or more (SEQ ID NO: 25)). FIG. 5 exemplifies a schematic description of a non-enhanced embodiment of the strand displacement-based methods of the invention comprising use of a single composite primer comprising a 3'-DNA portion comprising a poly-dT sequence, and further comprising a random sequence 3' the poly-dT sequence. Composite primer 1 further comprises a 5'-RNA portion that is not substantially hybridizable to the RNA target sequences (i.e. a tail under conditions in which the poly-dT sequence hybridizes). Optionally, a second composite primer may be used as described below.

The method involves the following steps: (a) primer extension to form an RNA/DNA heteroduplex of a target RNA and a first strand cDNA; (b) formation of a second primer extension product (second strand cDNA) that is of the same sense as the input target RNA. The second primer extension product generally comprises a 3'-portion that is complementary to the 5'-RNA portion of the composite primer (i.e., the tail); (c) linear amplification of the complement of the second strand cDNA by primer extension (from a composite primer) and strand displacement to produce multiple copies of antisense single stranded DNA products (that are complementary to the RNA sequence of interest).

Figure 6D:
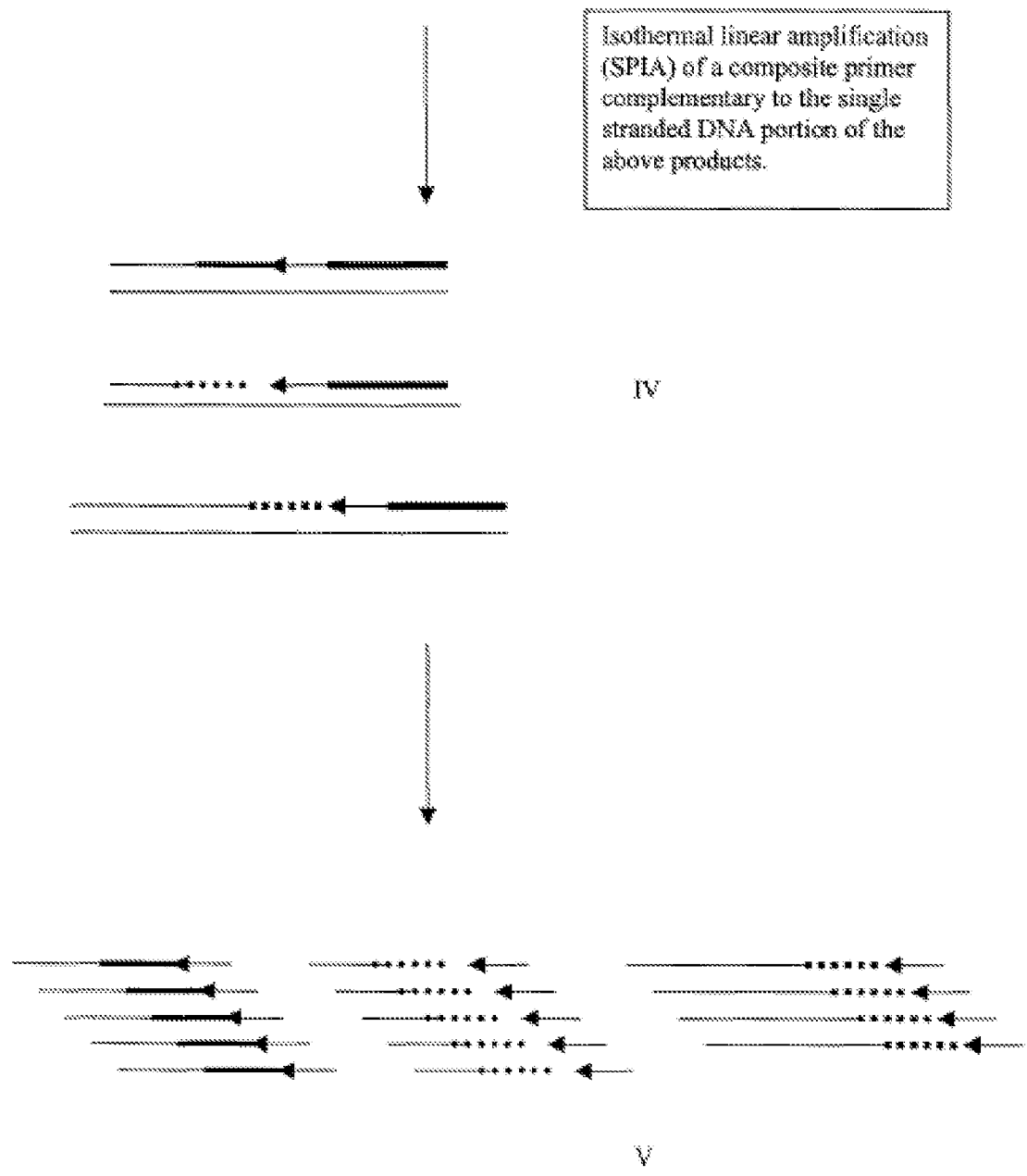

FIG. 6 exemplifies a schematic description of an non-enhanced embodiment of the strand displacement-based methods of the invention comprising use of a single composite primer comprising a 3'-DNA portion comprising a random sequence and further comprising a 5'-RNA portion that is not substantially hybridizable to the RNA target sequences (i.e. a tail under conditions in which the random sequence hybridizes). Optionally, a second composite primer may be used as described below.

The method involves the following steps: (a) primer extension to form RNA/DNA heteroduplexes of a target RNA and a first strand cDNA; (b) formation of second primer extension products (second strand cDNA) that is of the same sense as the input target RNA. The second primer extension product generally comprises a 3'-portion that is complementary to the 5'-RNA portion of the composite primer (i.e., the tail); (c) linear amplification of the sense DNA strand by primer extension from a composite primer and strand displacement to produce multiple copies of antisense single stranded DNA products that are complementary to the RNA sequence of interest.

As illustrated in these embodiments, all steps are isothermal, although the temperatures for each of the steps may or may not be the same. It is understood that various other embodiments may be practiced, given the general description provided above. It is further understood that the formation of a second primer extension product may be accomplished by any method known in the art or described herein (e.g., extension of a hybridized second primer or RNA fragment).

As is evident from the description herein, the amplification methods can also include a transcription step employing a propromoter polynucleotide in the same manner as that described with respect to the enhanced methods of amplification using a composite primer and a second primer. The single stranded RNA products of the enhanced methods of amplification would generally comprise a 3'-region that is complementary to the 5'-RNA portion of the first composite primer.

Figure 7:
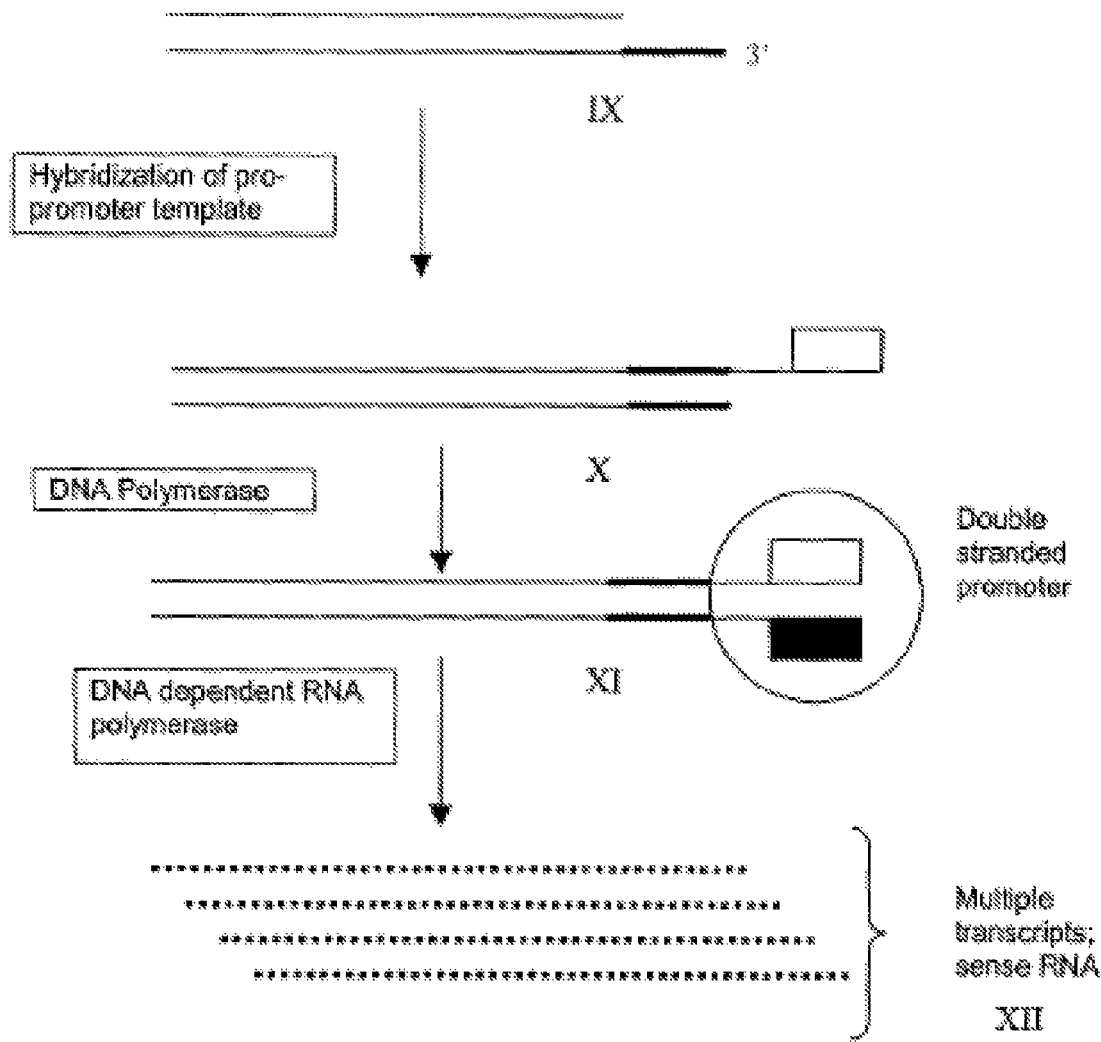
FIG. 7 shows a diagrammatic representation of an enhanced isothermal RNA amplification process using a single composite primer and transcription to generate multiple copies of RNA product comprising sequences complementary to the target RNA.

FIG. 7 exemplifies a schematic description of an enhanced embodiment of the strand displacement-based methods of the invention comprising use of (a) a single composite primer comprising a 3'-DNA portion comprising a random sequence and further comprising a 5'-RNA portion that is not substantially hybridizable to the RNA target sequences (i.e. a tail under conditions in which the random sequence hybridizes); and (b) a propromoter oligonucleotide). Optionally, a second composite primer may be used as described herein.

Figure 8A:
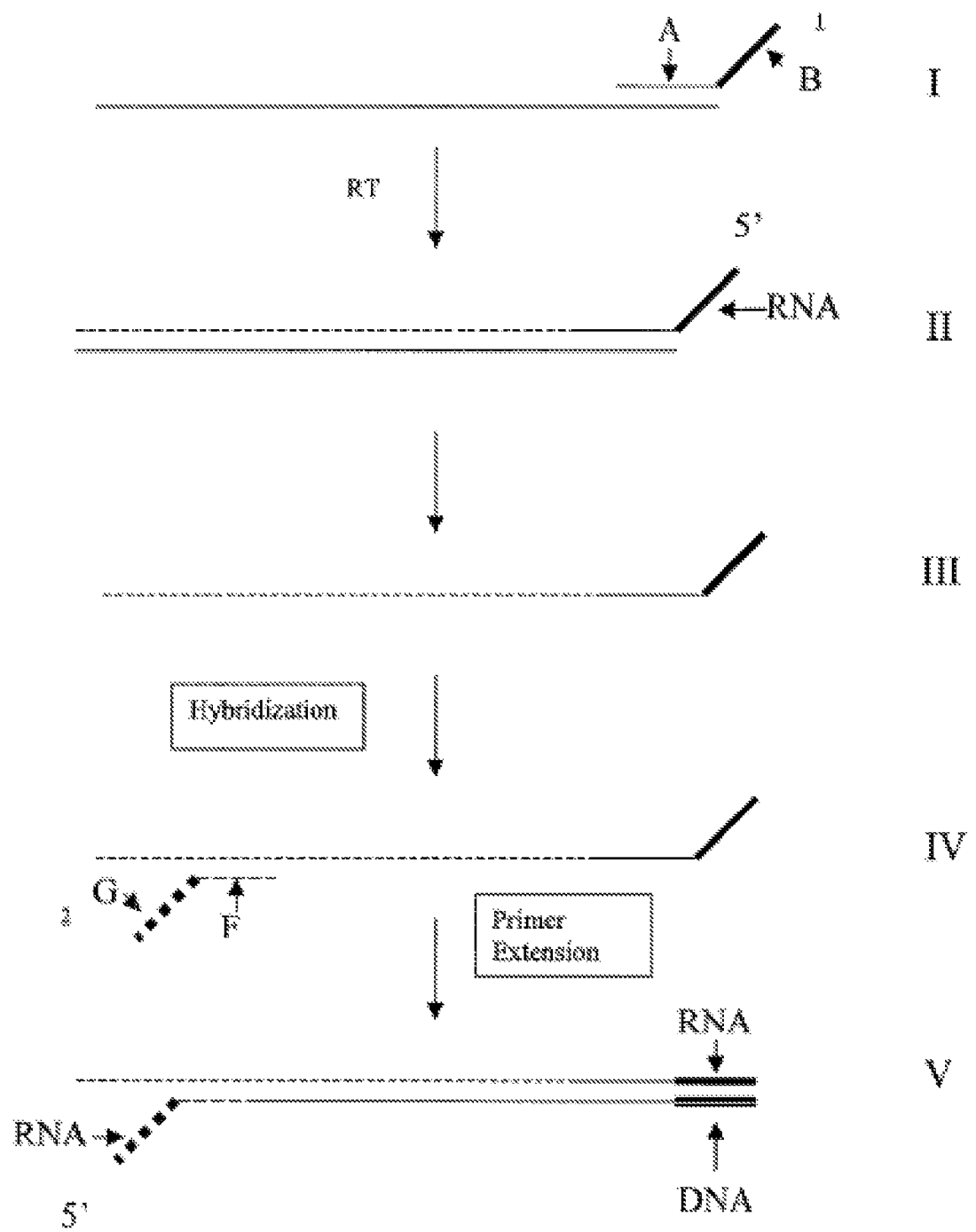
FIGS. 8A-C show a diagrammatic representation of a linear isothermal RNA amplification process using two composite primers and strand displacement to generate multiple copies of single stranded DNA products comprising sequences complementary to the target RNA and sequences identical to the target RNA.
Figure 8B:
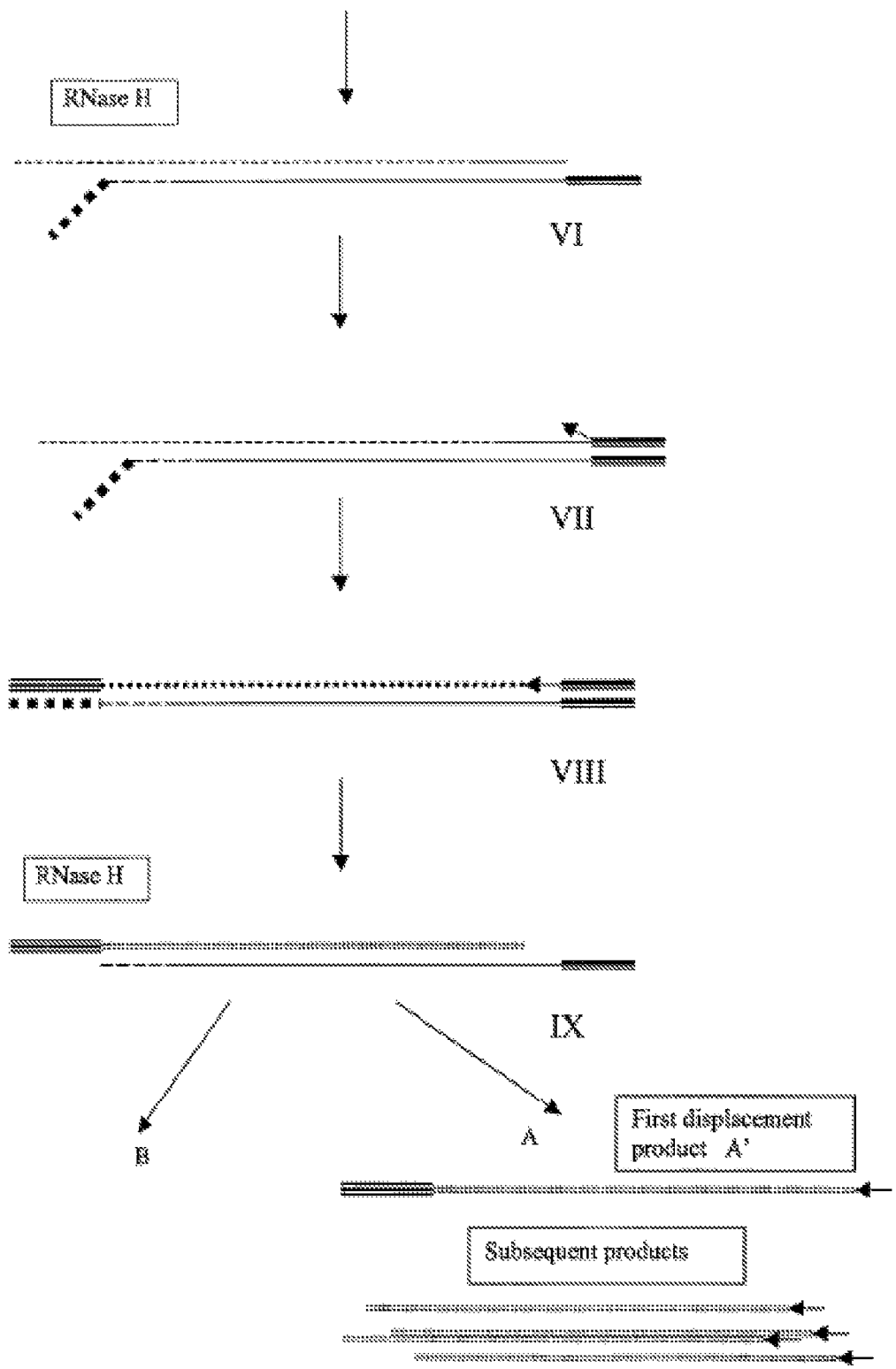
Figure 8C:
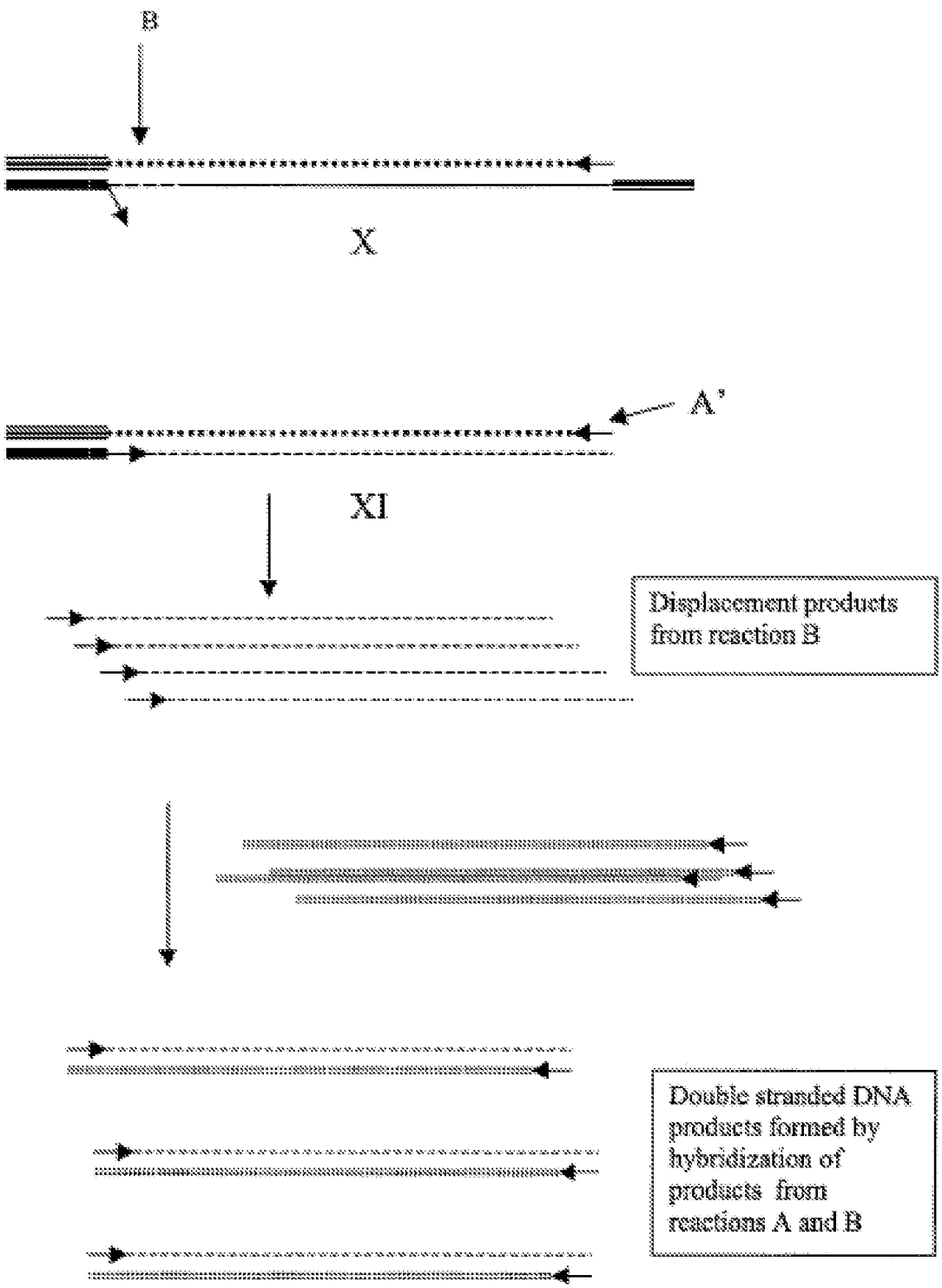

The method involves the following steps: (a) primer extension to form RNA/DNA heteroduplexes of a target RNA and a first strand cDNA; (b) formation of second primer extension products (second strand cDNA) that is of the same sense as the input target RNA and cleavage of RNA present in a RNA/DNA heteroduplex by an agent (such as RNase H) capable of cleaving RNA present in an RNA/DNA heteroduplex, whereby a double stranded complex of first and second primer extension product comprising a 3' single stranded portion is generated (complex IX in FIG. 8, which correspond to complex IX as illustrated in FIG. 1); and (c) a PTO binds to double stranded product IX to form complex X, as shown in FIG. 8. DNA polymerase extends the 3' end of the second primer extension product in complex XIII, along the PTO template to form complex XI comprising a double stranded promoter sequence at one end; and (d) transcription using DNA-dependent RNA polymerase to produce multiple copies of sense RNA products. As illustrated, all steps are isothermal, although the temperatures for each of the steps may or may not be the same.

As illustrated in FIG. 8, a promoter template oligonucleotide, 3 (PTO), can be designed as follows: the 3' portion is the same as the 5' RNA portion of the first composite primer (that hybridizes to template RNA). This design enables the PTO to hybridize to the single stranded 3' portion of the second primer extension product (which is present in a complex with the first primer extension product). The 5'-most portion of the PTO is a promoter sequence for a DNA-dependent RNA polymerase, which, as described above, is used in certain (namely, the other "enhanced" methods) embodiments of the amplification methods of the invention.

Linear mRNA Amplification Using a First Composite Primer, a Second Composite Primer, and a Target RNA The invention provides methods of producing single stranded antisense and sense polynucleotide, generally DNA, copies of an RNA sequence of interest using a first composite primer, a second composite primer which is used to generate the second strand cDNA, and a target RNA. In this aspect of the invention, a first composite primer is used to generate first extension product (generally cDNA), which is a substrate for the linear amplification using a composite primer, as described above. In addition, a second composite primer is used to generate a second strand cDNA which is a substrate for linear amplification, resulting in production of single stranded polynucleotide copies of the RNA sequence of interest.

The method involves the following: (a) formation of a double stranded cDNA comprising a RNA-DNA heteroduplex at each end of the cDNA; and (b) linear amplification of first strand (sense) cDNA and second strand (antisense) cDNA by primer extension from the first composite primer and from the second composite primer (which binds to the first strand cDNA), and strand displacement. Single stranded first and second strand cDNA product is produced, which is useful for, for example, producing cDNA libraries. As is evident, in this aspect of the invention, the second primer extension product is primed by a composite primer.

FIG. 8 illustrates one embodiment of the invention. Two composite primers comprising different "tail" sequences are used to generate a double stranded cDNA comprising a RNA-DNA heteroduplex at each end of the cDNA. Cleavage of RNA by an agent that cleaves RNA from an RNA/DNA heteroduplex permits binding of another first composite primer, another second composite primer (that hybridizes to the first primer extension product), extension and strand displacement, whereby multiple copies of an antisense single stranded product and multiple copies of a sense single stranded DNA product are produced. Combination of sense and antisense single stranded cDNA product is capable of producing double stranded cDNA. The process of the amplification methods of the invention resulting in generation of single stranded cDNA products comprising sequences complementary to an RNA sequence(s) of interest and sequences comprising an RNA sequence(s) of interest is as follows (an embodiment of which is illustrated in FIG. 7):

A) Formation of a Double Stranded cDNA Substrate for Linear Amplification

1. Composite primer 1 binds to an RNA target in a sample by hybridization of the primer portion A (which can be based at least in part on the poly-A sequence of the mRNA), to form complex I.
2. A reverse transcriptase extends the hybridized primer 1 along the target RNA strand to which it is hybridized, to form an RNA/DNA duplex, labeled II. An agent (such as RNase H) degrades the target RNA strand of the hybrid duplex to generate a single stranded first strand cDNA (labeled "III"). The 5' end of III is primer 1.
3. Composite primer 2, binds to the first strand cDNA, III, by hybridization of sequence F, to form complex IV.
4. Composite primer 2 is extended along the cDNA strand III by a DNA polymerase to form a double stranded product (labeled "V") which consists of first and second strand cDNA. Primer extension along the 5' RNA portion of IV by an RNA-dependent DNA polymerase such as a reverse transcriptase results in formation of an RNA/DNA hybrid portion at one end of complex V.
5. An agent (such as RNase H) degrades the RNA portion of the RNA/DNA hybrid at one end of complex V, to create a partial double stranded complex (labeled "VI") with a 3' DNA single stranded end, which has a sequence which is the complement of portion B of the composite primer 1.
6. Composite primer 1 binds to complex VI by hybridization of the RNA portion to the single stranded DNA end, which is complementary to it, to form complex VII.
7. Primer extension of bound primer 1 in complex VII along the sense cDNA strand results in displacement of the previous primer extension product (VII), and replicates portion "G" of the second composite primer, to form complex VIII.
8. An agent (such as RNase H) cleaves the RNA portions of the RNA/DNA heteroduplexes, forming complex VIII. Complex VIII has two RNA/DNA heteroduplexes comprised of composite primer 1 and the complement of composite primer 1 at one end, and the second composite primer and the complement of the second composite primer at the other end. Complex VIII is a substrate for subsequence reactions denoted "A" and "B".

B) Isothermal Linear Amplification
9. In reaction A, a first composite primer binds to complex VIII. Primer extension and displacement produces first displacement product A. RNase cleavage creates a site for binding of a first composite primer, and subsequence primer extension, whereby single stranded antisense DNA product accumulates.
10. In reaction B, a second composite primer binds to complex VIII (or to first displacement product A). Primer extension and displacement produces single stranded sense DNA products.

The single stranded products can be annealed to form a double stranded complex of first and second strand cDNA, or can be prevented from annealing (or subsequently denatured) to produce a mixture of single stranded first and second strand cDNA.

Components and Reaction Conditions Used in the Methods of the Invention
Template Nucleic Acid The RNA target to be amplified includes RNAs from any source in purified or unpurified form, which can be RNA such as total RNA, tRNA, mRNA, rRNA, mitochondrial RNA, chloroplast RNA, DNA-RNA hybrids, or mixtures thereof, from any source and/or species, including human, animals, plants, and microorganisms such as bacteria, yeasts, viruses, viroids, molds, fungi, plants, and fragments thereof. RNAs can be obtained and purified using standard techniques in the art. Amplification of a DNA target (including genomic DNA target) would require initial transcription of the DNA target into RNA form, which can be achieved using methods disclosed in Kurn, U.S. Pat. No. 6,251,639 B1, and by other techniques (such as expression systems) known in the art. Amplification of a DNA-RNA hybrid would require denaturation of the hybrid to obtain a ssRNA, or denaturation followed by transcription of the DNA strand to obtain an RNA. The target RNA can be only a minor fraction of a complex mixture such as a biological sample and can be obtained from various biological material by procedures well known in the art. The target RNA can be known or unknown and may contain more than one desired specific nucleic acid sequence of interest, each of which may be the same or different from each other. Therefore, the amplification process is useful not only for producing large amounts of one specific nucleic acid sequence, but also for amplifying simultaneously more than one different specific nucleic acid sequence located on the same or different nucleic acid molecules.

The initial step of the amplification of a target RNA sequence is rendering the target single stranded. If the target nucleic acid is double stranded (e.g., RNA/DNA hybrid) the initial step could be target denaturation. Denaturation may also be carried out to remove secondary structure present in a RNA target molecule. The denaturation step may be thermal denaturation or any other method known in the art.

Composite Primer

The methods of the invention employ a composite primer that is composed of RNA and DNA portions. As described herein, when used for hybridizing and initiating the methods of RNA amplification as described herein, the composite primer generally comprises a DNA portion which hybridizes to the RNA target (which, as described herein, can have any of a number of sequence permutations, depending on the nature of the RNA (whether a species or a population) designed to be amplified). When used to amplify a cDNA strand produced by the methods of the invention described herein, the composite primer is designed such that subsequent displacement of the primer extension product by binding of a new (additional) composite primer and the extension of the new primer by the polymerase can be achieved. In addition, cleavage of the RNA portion of the primer extension product leads to generation of amplification product which is not a substrate for amplification by the composite primer. It is understood that, in the following section that generally describes aspects of the composite primers used in the methods of the invention, characteristics described may be applicable to the primers if used for hybridizing and initiating the RNA amplification (production of first extension product) and/or for linear displacement amplification.

Composite primers for use in the methods and compositions of the invention comprise a sequence capable of hybridizing to a target RNA. The sequence that is capable of hybridizing to the target RNA can be based on the particular sequence of a specific target RNA (for e.g., the mRNA of a particular gene), or be based on a more general sequence type known to be present in a plurality of RNA species, such as the poly-A tail sequence generally believed in the art to be present in all eukaryotic mRNA. In addition, the sequence that is capable of hybridizing to the target RNA may comprise a sequence complementary to the poly-A tail of mRNA, and may further comprise an additional random sequence (generally not complementary to a poly-A sequence) at the 3' end of the 3' portion (or a population of random sequences).

The sequence that is capable of hybridizing to the target RNA may also comprise a random sequence. Random primers are well known in the art, see, e.g., and include at least the following: primers hybridizable to two or more sequences in a sample; and primers comprising poly-dT sequences that are hybridizable to a multiplicity of RNAs in a sample (such as all mRNA). For convenience, a single random composite primer is discussed above. However, it is understood that the term "random primer" can refer to a primer that is a member of a population of primers which are collectively designed to a desired and/or significant population of target sequences.

It is also understood that the amplification of a plurality of mRNA species in a single reaction mixture may, but not necessarily, employ a multiplicity of primers (from two to many more). Thus, the invention contemplates the use of a multiplicity of different composite primers (random or non-random) when amplifying a plurality of mRNA species in a single reaction mixture.

In some embodiments, a first composite primer is used in the methods of the invention, including those steps which involve linear displacement amplification (SPIA) of the second cDNA strand. In other embodiments, a first and second, different, composite primer are used in the methods of the invention. The second composite primer is used for the linear displacement amplification (SPIA) step, and may comprise some or all of the sequence of the first composite primer, and the first composite primer may comprise some or all of the sequence of the second composite primer. In some embodiments, the second composite primer comprises a different sequence than the first composite primer.

In some embodiments, a composite primer is designed such that the entire primer hybridizes to the target RNA. In other embodiments, a composite primer comprises a sequence, preferably at the 5' end, that is not hybridizable (under a given set of conditions) to the target (for example, a non-hybridized 5' portion that would constitute a tail when the primer is bound to the target). Individual DNA and RNA portions of the composite primer may be completely or partially hybridizable to the target RNA. For example, the 5' RNA portion of a composite primer may be partially hybridizable and partially nonhybridizable, or the DNA portion of a composite primer may be partially hybridizable and partially nonhybridizable, or both. Put another way, DNA portions can constitute part of a "tail" and RNA portions can be partially or completely hybridizable to target RNA. For example, the 5' RNA portion of a composite primer may be partially hybridizable and partially nonhybridizable, or the DNA portion of a composite primer may be partially hybridizable and partially nonhybridizable, or both.

For use in linear displacement amplification, a composite primer comprises at least one RNA portion that is capable of (a) binding (hybridizing) to a sequence on the second strand cDNA (interchangeably called "second primer extension product" or "composite primer extension product") independent of hybridization of the DNA portion(s) to a sequence on the same second strand cDNA; and (b) being cleaved with an agent such as a ribonuclease when hybridized to the second primer or fragment extension product. The composite primers bind to the second strand cDNA to form a partial heteroduplex in which only the RNA portion of the primer is cleaved upon contact with an agent which cleaves RNA in an RNA/DNA hybrid, such as an enzyme, such as a ribonuclease (such as RNase H), while the second strand cDNA remains intact, thus enabling annealing of another composite primer.

When used for the linear displacement amplification described herein, the composite primers also comprise a 3' DNA portion that is capable of hybridization to a sequence on the second strand cDNA such that its hybridization to the second strand cDNA is favored over that of the nucleic acid strand that is displaced from the second strand cDNA by the DNA polymerase. Such primers can be rationally designed based on well known factors that influence nucleic acid binding affinity, such as sequence length and/or identity, as well as hybridization conditions. In a preferred embodiment, hybridization of the 3' DNA portion of the composite primer to its complementary sequence in the second strand cDNA favored over the hybridization of the homologous sequence in the 5' end of the displaced strand to the second strand cDNA.

Generation of primers suitable for extension by polymerization is well known in the art, such as described in PCT Pub. No. WO99/42618 (and references cited therein). The composite primer comprises a combination of RNA and DNA (see definition above), with the 3'-end nucleotide being a nucleotide suitable for nucleic acid extension. The 3'-end nucleotide can be any nucleotide or analog that when present in a primer, is extendable by a DNA polymerase. Generally, the 3'-end nucleotide has a 3'-OH. Suitable primers include those that comprise at least one portion of RNA and at least one portion of DNA. For example, composite primers can comprise a 5'-RNA portion and a 3'-DNA portion (in which the RNA portion is adjacent to the 3'-DNA portion); or 5'- and 3'-DNA portions with an intervening RNA portion. Accordingly, in one embodiment, the composite primer comprises a 5' RNA portion and a 3'-DNA portion, preferably wherein the RNA portion is adjacent to the 3'-DNA portion. In another embodiment, the composite primer comprises 5'- and 3'-DNA portions with at least one intervening RNA portion (i.e., an RNA portion between the two DNA portions). In yet another embodiment, the composite primer of the invention comprises a 3'-DNA portion and at least one intervening RNA portion (i.e., an RNA portion between DNA portions).

The length of an RNA portion in a composite primer comprising a 3'-DNA portion and an RNA portion can be preferably from about 1 to about 50, more preferably from about 3 to about 20, even more preferably from about 4 to about 15, and most preferably from about 5 to about 10 nucleotides. In some embodiments of a composite primer comprising a 3'-DNA portion and an RNA portion, an RNA portion can be at least about any of 1, 3, 4, 5 nucleotides, with an upper limit of about any of 10, 15, 20, 25, 3, 50 nucleotides.

The length of the 5'-RNA portion in a composite primer comprising a 5'-RNA portion and a 3'-DNA portion can be preferably from about 3 to about 50 nucleotides, more preferably from about 5 to about 20 nucleotides, even more preferably from about 7 to about 18 nucleotides, preferably from about 8 to about 17 nucleotides, and most preferably from about 10 to about 15 nucleotides. In other embodiments of a composite primer comprising a 5'-RNA portion and a 3'-DNA portion, the 5'-RNA portion can be at least about any of 3, 5, 7, 8, 10 nucleotides, with an upper limit of about any of 15, 17, 18, 20, 50 nucleotides. In one embodiment, the composite primer has an RNA portion of about 14 nucleotides.

In embodiments of a composite primer comprising a 5'-RNA portion and a 3'-DNA portion further comprising non-5'-RNA portion(s), a non-5'-RNA portion can be preferably from about 1 to about 7 nucleotides, more preferably from about 2 to about 6 nucleotides, and most preferably from about 3 to about 5 nucleotides. In certain embodiments of a composite primer comprising a 5'-RNA portion and a 3'-DNA portion further comprising non-5'-RNA portion(s), a non-5'-RNA portion can be at least about any of 1, 2, 3, 5, with an upper limit of about any of 5, 6, 7, 10 nucleotides.

In embodiments of a composite primer comprising a 5'-RNA portion and a 3'-DNA portion, in which the 5'-RNA portion is adjacent to the 3'-DNA portion, the length of the 5'-RNA portion can be preferably from about 3 to about 50 nucleotides, more preferably from about 5 to about 20 nucleotides, even more preferably from about 7 to about 18 nucleotides, preferably from about 8 to about 17 nucleotides, and most preferably from about 10 to about 15 nucleotides. In certain embodiments of a composite primer comprising a 5'-RNA portion and a 3'-DNA portion, in which the 5'-RNA portion is adjacent to the 3'-DNA portion, the 5'-RNA portion can be at least about any of 3, 5, 7, 8, 10 nucleotides, with an upper limit of about any of 15, 17, 18, 20, 50 nucleotides.

The length of an intervening RNA portion in a composite primer comprising 5'- and 3'-DNA portions with at least one intervening RNA portion can be preferably from about 1 to about 7 nucleotides, more preferably from about 2 to about 6 nucleotides, and most preferably from about 3 to about 5 nucleotides. In some embodiments of a composite primer comprising 5'- and 3'-DNA portions with at least one intervening RNA portion, an intervening RNA portion can be at least about any of 1, 2, 3, 5 nucleotides, with an upper limit of about any of 5, 6, 7, 10 nucleotides. The length of an intervening RNA portion in a composite primer comprising a 3'-DNA portion and at least one intervening RNA portion can be preferably from about 1 to about 7 nucleotides, more preferably from about 2 to about 6 nucleotides, and most preferably from about 3 to about 5 nucleotides. In some embodiments of a composite primer comprising a 3'-DNA portion and at least one intervening RNA portion, an intervening RNA portion can be at least about any of 1, 2, 3, 5 nucleotides, with an upper limit of about any of 5, 6, 7, 10 nucleotides. In a composite primer comprising a 3'-DNA portion and at least one intervening RNA portion, further comprising a 5'-RNA portion, the 5'-RNA portion can be preferably from about 3 to about 25 nucleotides, more preferably from about 5 to about 20 nucleotides, even more preferably from about 7 to about 18 nucleotides, preferably from about 8 to about 17 nucleotides, and most preferably from about 10 to about 15 nucleotides. In some embodiments of a composite primer comprising a 3'-DNA portion and at least one intervening RNA portion, further comprising a 5'-RNA portion, the 5'-RNA portion can be at least about any of 3, 5, 7, 8, 10 nucleotides, with an upper limit of about any of 15, 17, 18, 20 nucleotides.

The length of the 3'-DNA portion in a composite primer comprising a 3'-DNA portion and an RNA portion can be preferably from about 1 to about 20, more preferably from about 3 to about 18, even more preferably from about 5 to about 15, and most preferably from about 7 to about 12 nucleotides. In some embodiments of a composite primer comprising a 3'-DNA portion and an RNA portion, the 3'-DNA portion can be at least about any of 1, 3, 5, 7, 10 nucleotides, with an upper limit of about any of 10, 12, 15, 18, 20, 22 nucleotides.

The length of the 3'-DNA portion in a composite primer comprising a 5'-RNA portion and a 3'-DNA portion can be preferably from about 1 to about 20 nucleotides, more preferably from about 3 to about 18 nucleotides, even more preferably from about 5 to about 15 nucleotides, and most preferably from about 7 to about 12 nucleotides. In some embodiments of a composite primer comprising a 5'-RNA portion and a 3'-DNA portion, the 3' DNA portion can be at least about any of 1, 3, 5, 7, 10 nucleotides, with an upper limit of about any of 10, 12, 15, 18, 20, 22 nucleotides.

In embodiments of a composite primer comprising a 5'-RNA portion and a 3'-DNA portion, further comprising non-3'-DNA portion(s), a non-3'-DNA portion can be preferably from about 1 to about 10 nucleotides, more preferably from about 2 to about 8 nucleotides, and most preferably from about 3 to about 6 nucleotides. In some embodiments of a composite primer comprising a 5'-RNA portion and a 3'-DNA portion, further comprising non-3'-DNA portion(s), a non-3'-DNA portion can be at least about any of 1, 2, 3, 5 nucleotides, with an upper limit of about any of 6, 8, 10, 12 nucleotides.

In embodiments of a composite primer comprising a 5'-RNA portion and a 3'-DNA portion in which the 5'-RNA portion is adjacent to the 3'-DNA portion, the length of the 3'-DNA portion can be preferably from about 1 to about 20 nucleotides, more preferably from about 3 to about 18 nucleotides, even more preferably from about 5 to about 15 nucleotides, and most preferably from about 7 to about 12 nucleotides. In certain embodiments of the primer comprising a 5'-RNA portion and a 3'-DNA portion in which the 5'-RNA portion is adjacent to the 3'-DNA portion, the 3'-DNA portion can be at least about any of 1, 3, 5, 7, 10 nucleotides, with an upper limit of about any of 10, 12, 15, 18, 20, 22 nucleotides.

The length of a non-3'-DNA portion in a composite primer comprising 5'- and 3'-DNA portions with at least one intervening RNA portion can be preferably from about 1 to about 10 nucleotides, more preferably from about 2 to about 8 nucleotides, and most preferably from about 3 to about 6 nucleotides. In some embodiments of a primer comprising 5'- and 3'-DNA portions with at least one intervening RNA portion, a non-3'-DNA portion can be at least about any of 1, 2, 3, 5 nucleotides, with an upper limit of about any of 6, 8, 10, 12 nucleotides.

The length of the 3'-DNA portion in a composite primer comprising 5'- and 3'-DNA portions with at least one intervening RNA portion can be preferably from about 1 to about 20 nucleotides, more preferably from about 3 to about 18 nucleotides, even more preferably from about 5 to about 15 nucleotides, and most preferably from about 7 to about 12 nucleotides. In some embodiments of a composite primer comprising 5'- and 3'-DNA portions with at least one intervening RNA portion, the 3'-DNA portion can be at least about any of 1, 3, 5, 7, 10 nucleotides, with an upper limit of about any of 10, 12, 15, 18, 20, 22 nucleotides.

The length of a non-3'-DNA portion (i.e., any DNA portion other than the 3'-DNA portion) in a composite primer comprising a 3'-DNA portion and at least one intervening RNA portion can be preferably from about 1 to about 10 nucleotides, more preferably from about 2 to about 8 nucleotides, and most preferably from about 3 to about 6 nucleotides. In some embodiments of a composite primer comprising a 3'-DNA portion and at least one intervening RNA portion, a non-3'-DNA portion can be at least about any of 1, 3, 5, 7, 10 nucleotides, with an upper limit of about any of 6, 8, 10, 12 nucleotides. The length of the 3'-DNA portion in a composite primer comprising a 3'-DNA portion and at least one intervening RNA portion can be preferably from about 1 to about 20 nucleotides, more preferably from about 3 to about 18 nucleotides, even more preferably from about 5 to about 15 nucleotides, and most preferably from about 7 to about 12 nucleotides. In some embodiments of a composite primer comprising a 3'-DNA portion and at least one intervening RNA portion, the 3'-DNA portion can be at least about any of 1, 3, 5, 7, 10 nucleotides, with an upper limit of about any of 10, 12, 15, 18, 20, 22 nucleotides. It is understood that the lengths for the various portions can be greater or less, as appropriate under the reaction conditions of the methods of this invention.

In some embodiments, the 5'-DNA portion of a composite primer includes the 5'-most nucleotide of the primer. In some embodiments, the 5'-RNA portion of a composite primer includes the 5' most nucleotide of the primer. In other embodiments, the 3'-DNA portion of a composite primer includes the 3' most nucleotide of the primer. In other embodiments, the 3'-DNA portion is adjacent to the 5'-RNA portion and includes the 3' most nucleotide of the primer (and the 5'-RNA portion includes the 5' most nucleotide of the primer).

The total length of the composite primer can be preferably from about 10 to about 50 nucleotides, more preferably from about 15 to about 30 nucleotides, and most preferably from about 20 to about 25 nucleotides. In some embodiments, the length can be at least about any of 10, 15, 20, 25 nucleotides, with an upper limit of about any of 25, 30, 50, 60 nucleotides. It is understood that the length can be greater or less, as appropriate under the reaction conditions of the methods of this invention.

To achieve hybridization to a target nucleic acid (which, as is well known and understood in the art, depends on other factors such as, for example, ionic strength and temperature), the portion of the primer that is hybridizable to the target RNA is preferably of at least about 60%, more preferably at least about 75%, even more preferably at least about 90%, and most preferably at least about 95% complementarity to the target nucleic acid.

As described herein, one or more composite primers may be used in an amplification reaction.

Second Primer

The second primer in the methods of the invention (which primes generation of the second primer extension product, interchangeably referred to as second strand cDNA) comprises a sequence (which may or may not be the whole of the primer) that is hybridizable (under a given set of conditions) to a first strand cDNA (interchangeably called first primer extension product) at a site on the first strand cDNA such that the second strand cDNA would include the RNA sequence of interest. In some embodiments, the hybridizable sequence of the second primer is designed based on a known sequence of the desired binding site on a first strand cDNA. In other embodiments, the hybridizable sequence is based on random sequences, for example, known in the art to be suitable for random priming of first strand cDNAs generated from a plurality of RNA species. In other embodiments, the second primer comprises a strand switch oligonucleotide, described in U.S. Pat. Nos. 5,962,271 and 5,962,272, which is hybridizable to the Cap sequences present on mRNA and causes the reverse transcriptase to switch from the mRNA template to the switch oligonucleotide, permitting generation of a second strand cDNA primed by the "switch oligonucleotide". Alternatively, a homopolymeric tail is added to the 3' terminus of the first primer extension product, and the second primer comprises the complement of the homopolymeric tail.

In some embodiments, the second primer comprises DNA. In other embodiments, the second primer consists of DNA. In other embodiments, as described herein, the second primer is a fragment of the target RNA, with the fragment being generated by cleavage of the RNA target.

In some embodiments, the second primer (which primes generation of the second strand cDNA) is a composite primer (as described above). In these embodiments, the method involves the following: (a) formation of a double stranded cDNA comprising a RNA-DNA heteroduplex at one end of the cDNA; and (b) linear amplification of first strand (sense) cDNA, whereby multiple copies of single stranded first strand cDNA is generated.

To achieve hybridization to a first strand cDNA (which, as is well known and understood in the art, depends on other factors such as, for example, ionic strength and temperature), the sequence of the second primer that is hybridizable to the first strand cDNA is preferably of at least about 60%, more preferably at least about 75%, even more preferably at least about 90%, and most preferably at least about 95% complementarity to the first strand cDNA.

In certain embodiments (typically, but not necessarily, ones that include transcription), the second primer may also comprise a sequence, preferably a sequence at the 5' end (which generally includes the 5' most nucleotide), that is not hybridizable to a first strand cDNA under a given set of conditions. This sequence enables the creation of a defined end sequence for the 5' end of the second strand cDNA (and thus, subsequently the 3' end of the single stranded DNA products). Having a defined end sequence at the 3' end of the single stranded DNA products is particularly advantageous with respect to hybridization (in embodiments that include a transcription step) of a propromoter polynucleotide to displaced first primer extension products in subsequent steps. In certain embodiments, a 5' non-hybridizable sequence comprises a sequence the complement of which is hybridizable by a propromoter polynucleotide. Single stranded DNA products comprising a 3' defined end sequence are also useful for hybridization to a complementary oligonucleotide attached to a binding partner or substrate, for example, a generic microarray as described herein. Accordingly, the invention provides methods of making these products with a 3' defined end, as described herein.

In one embodiment, the second primer comprises DNA. In another embodiment, the second primer comprises RNA. In yet another embodiment, the second primer comprises DNA and RNA.

In some embodiments, the second primer is provided by self priming (for example, by a hairpin loop) at the 3' end of the composite primer extension product. In these embodiments, a sequence at the 3' end of the composite primer extension product hybridizes to another sequence in the composite primer extension product itself, for example as described in U.S. Pat. No. 6,132,997. In these embodiments, said sequence at the 3' of the composite primer extension product is generally cleaved (for example, with 51 nuclease) following its hybridization to the composite primer extension product and/or its extension along the composite primer extension product. U.S. Pat. No. 6,132,997.

In some embodiments, the second primer is provided by one or more target RNA fragments. Such a target RNA fragment can be generated as a result of incomplete degradation of a target RNA in a complex of target RNA and first primer extension product by an agent (such as an enzyme) that cleaves RNA in an RNA/DNA hybrid, such that one or more RNA fragments remain bound to the first primer extension product.

Polynucleotide Comprising a Propromoter and a Region which Hybridizes to a Primer Extension Product Some embodiments employ a propromoter polynucleotide comprising a propromoter and a region which hybridizes to a primer extension product. In some embodiments, the propromoter polynucleotide is provided as a PTO, as described in greater detail below.

Propromoter Template Oligonucleotide

In some embodiments, the methods employ a promoter sequence for transcription which is provided by a propromoter template oligonucleotide (PTO).

A PTO for use in the methods and compositions of the invention is a single-stranded polynucleotide, generally DNA, comprising a propromoter sequence that is designed for formation of a double stranded promoter of an RNA polymerase, and a portion capable of hybridizing to the 3' end of a primer extension product. In an embodiment of the invention, the portion capable of hybridizing to the 3' end of a primer extension product comprises a sequence the complement of which is hybridizable to a defined end sequence of the second primer extension product (and thus, subsequently the 3' end of the single stranded DNA products). In another embodiment, the portion capable of hybridizing to the 3' end of a primer extension product comprises a random sequence. In another embodiment, the portion capable of hybridizing to the 3' end of a primer extension product comprises a sequence the complement of which is capable of hybridizing to sequences found at the 3' end of a multiplicity of first strand cDNAs.

In a preferred embodiment, the propromoter sequence is located in the 5' portion of the oligonucleotide and the hybridizing sequence is located in the 3' portion of the oligonucleotide. In one embodiment, and most typically, the promoter and hybridizing sequences are different sequences. In another embodiment, the promoter and hybridizing sequences overlap in sequence identity. In yet another embodiment, the promoter and hybridizing sequences are the same sequence, and thus are in the same location on the PTO. In the embodiments wherein hybridization of the PTO to the primer extension product results in a duplex comprising an overhang (the 5' end of the PTO that does not hybridize to the displaced primer extension product, typically comprising all or part of the propromoter sequence), DNA polymerase fills in the overhang to create a double stranded promoter capable of effecting transcription by a suitable RNA polymerase.

Promoter sequences that allow transcription of a template DNA are known in the art and have been discussed above. Preferably, the promoter sequence is selected to provide optimal transcriptional activity of the particular RNA polymerase used. Criteria for such selection, i.e., a particular promoter sequence particularly favored by a particular RNA polymerase, is also known in the art. For example, the sequences of the promoters for transcription by T7 DNA dependent RNA polymerase and SP6 are known in the art. The promoter sequence can be from a prokaryotic or eukaryotic source.

In some embodiments, the PTO comprises an intervening sequence between a propromoter sequence and a portion capable of hybridizing to the 3' end of the primer extension product. Suitable length of the intervening sequence can be empirically determined, and can be at least about 1, 2, 4, 6, 8, 10, 12, 15 nucleotides. Suitable sequence identity of the intervening sequence can also be empirically determined, and the sequence is designed to preferably, but not necessarily, enhance degree of amplification as compared to omission of the sequence. In one embodiment, the intervening sequence is a sequence that is designed to provide for enhanced, or more optimal, transcription by the RNA polymerase used. Generally, the sequence is not related (i.e., it does not substantially hybridize) to the target nucleic acid. More optimal transcription occurs when transcriptional activity of the polymerase from a promoter that is operatively linked to said sequence is greater than from a promoter that is not so linked. The sequence requirements for optimal transcription are generally known in the art as previously described for various DNA dependent RNA polymerases, such as in U.S. Pat. Nos. 5,766,849 and 5,654,142, and can also be empirically determined.

In another embodiment, the PTO comprises a sequence that is 5' to the propromoter sequence, i.e., the PTO comprises additional nucleotides (which may or may not be transcriptional regulatory sequences) located 5' to the propromoter sequence. Generally, but not necessarily, the sequence is not hybridizable (under a given set of conditions) to the primer extension product.

In one embodiment, the PTO cannot function efficiently as a primer for nucleic acid extension. Techniques for blocking the primer function of the PTO include any that prevent addition of nucleotides to the 3' end of the PTO by a DNA polymerase. Such techniques are known in the art, including, for example, substitution or modification of the 3' hydroxyl group, or incorporation of a modified nucleotide, such as a dideoxynucleotide, in the 3'-most position of the PTO that is not capable of anchoring addition of nucleotides by a DNA polymerase. It is possible to block the 3' end using a label, or a small molecule which is a member of a specific binding pair, such as biotin. It is also possible to render the 3' end non-extendable by addition of nucleotides which cannot hybridize to a primer extension product, either due to non-complementarity or due to structural modifications which do not support hydrogen bonding. In other embodiments, the PTO is not blocked.

The length of the portion of the PTO that hybridizes to a primer extension product of interest is preferably from about 5 to about 50 nucleotides, more preferably from about 10 to about 40 nucleotides, even more preferably from about 15 to about 35 nucleotides, and most preferably from about 20 to 30 nucleotides. In some embodiments, the hybridizing portion is at least about any of the following: 3, 5, 10, 15, 20; and less than about any of the following: 30, 40, 50, 60. The complementarity of the hybridizing portion is preferably at least about 25%, more preferably at least about 50%, even more preferably at least about 75%, and most preferably at least about 90%, to its intended binding sequence on the primer extension product of interest.

DNA Polymerase, an Agent Capable of Cleaving an RNA-DNA Hybrid, and RNA Polymerase The amplification methods of the invention employ the following enzymes: an RNA-dependent DNA polymerase, a DNA-dependent DNA polymerase, an agent capable of cleaving an RNA strand of an RNA-DNA hybrid (for example, a ribonuclease such as RNase H), and, in some aspects a DNA-dependent RNA polymerase. One or more of these activities may be found and used in a single enzyme. For example, RNase H activity may be supplied by an RNA-dependent DNA polymerase (such as reverse transcriptase) or may be provided in a separate enzyme. Reverse transcriptases useful for this method may or may not have RNase H activity.

One aspect of the invention is the formation of double stranded cDNA from a primer-RNA complex. This process generally utilizes the enzymatic activities of an RNA-dependent DNA polymerase, a DNA-dependent DNA polymerase and a agent capable of cleaving an RNA/DNA hybrid (such as RNase H).

RNA-dependent DNA polymerases for use in the methods and compositions of the invention are capable of effecting extension of a primer according to the methods of the invention. Accordingly, a preferred RNA-dependent DNA polymerase is one that is capable of extending a nucleic acid primer along a nucleic acid template that is comprised at least predominantly of ribonucleotides. Suitable RNA-dependent DNA polymerases for use in the methods and compositions of the invention include reverse transcriptase. Many reverse transcriptases, such as those from avian myeoloblastosis virus (AMV-RT), and Moloney murine leukemia virus (MMLV-RT) comprise more than one activity (for example, polymerase activity and ribonuclease activity) and can function in the formation of the double stranded cDNA molecules. However, in some instances, it is preferable to employ a reverse transcriptase which lacks the RNase H activity. Reverse transcriptase devoid of RNase H activity are known in the art, including those comprising a mutation of the wild type reverse transcriptase where the mutation eliminates the RNase H activity. In these cases, the addition of an RNase H from other sources, such as that isolated from *E. coli*, can be employed for the formation of the double stranded cDNA.

DNA-dependent DNA polymerases for use in the methods and compositions of the invention are capable of effecting extension of the composite primer according to the methods of the invention. Accordingly, a preferred polymerase is one that is capable of extending a nucleic acid primer along a nucleic acid template that is comprised at least predominantly of deoxynucleotides. The formation of the double stranded cDNA can be carried out by reverse transcriptase which comprises both RNA-dependent DNA polymerase and DNA-dependent DNA polymerase activities. Amplification of an RNA sequence according to methods of the invention involves the use of a DNA polymerase that is able to displace a nucleic acid strand from the polynucleotide to which the displaced strand is bound, and, generally, the more strand displacement capability the polymerase exhibits (i.e., compared to other polymerases which do not have as much strand displacement capability) is preferable. Preferably, the DNA polymerase has high affinity for binding at the 3'-end of an oligonucleotide hybridized to a nucleic acid strand. Preferably, the DNA polymerase does not possess substantial nicking activity. Generally, the DNA polymerase preferably has little or no 5'→3' exonuclease activity so as to minimize degradation of primer, or primer extension polynucleotides. Generally, this exonuclease activity is dependent on factors such as pH, salt concentration, whether the template is double stranded or single stranded, and so forth, all of which are familiar to one skilled in the art. Mutant DNA polymerases in which the 5'→3' exonuclease activity has been deleted, are known in the art and are suitable for the amplification methods described herein. Mutant DNA polymerases which lack both 5' to 3' nuclease and 3' to 5' nuclease activities have also been described, for example, exo$^{-/-}$ Klenow DNA polymerase. It is preferred that the DNA polymerase displaces primer extension products from the template nucleic acid in at least about 25%, more preferably at least about 50%, even more preferably at least about 75%, and most preferably at least about 90%, of the incidence of contact between the polymerase and the 5' end of the primer extension product. In some embodiments, the use of thermostable DNA polymerases with strand displacement activity is preferred. Such polymerases are known in the art, such as described in U.S. Pat. No. 5,744,312 (and references cited therein). Preferably, the DNA polymerase has little to no proofreading activity Suitable DNA polymerases for use in the methods and compositions of the invention include those disclosed in U.S. Pat. Nos. 5,648,211 and 5,744,312, which include exo$^-$ Vent (New England Biolabs), exo$^-$ Deep Vent (New England Biolabs), Bst (BioRad), exo$^-$ Pfu (Stratagene), Bca (Panvera), sequencing grade Taq (Promega), exo$^{-/-}$ Xlenow DNA polymerase, and thermostable DNA polymerases from thermoanaerobacter thermohydrosulfuricus.

The ribonuclease for use in the methods and compositions of the invention is capable of cleaving ribonucleotides in an RNA/DNA hybrid. Preferably, the ribonuclease cleaves ribonucleotides in an RNA/DNA hybrid regardless of the identity and type of nucleotides adjacent to the ribonucleotide to be cleaved. It is preferred that the ribonuclease cleaves independent of sequence identity. Examples of suitable ribonucleases for the methods and compositions of the invention are well known in the art, including ribonuclease H(RNase H) including Hybridase.

The DNA-dependent RNA polymerases for use in the methods and compositions of the invention are known in the art. Either eukaryotic or prokaryotic polymerases may be used. Examples include T7, T3 and SP6 RNA polymerases. Generally, the RNA polymerase selected is capable of transcribing from the promoter sequence provided by the propromoter polynucleotides as described herein. Generally, the RNA polymerase is a DNA-dependent polymerase, which is preferably capable of transcribing from a single stranded DNA template so long as the promoter region is double stranded.

In general, the enzymes used in the methods and compositions of the invention should not produce substantial degradation of the nucleic acid components of said methods and compositions.

Reaction Conditions and Detection

Appropriate reaction media and conditions for carrying out the methods of the invention are those that permit nucleic acid amplification according to the methods of the invention. Such media and conditions are known to persons of skill in the art, and are described in various publications, such as U.S. Pat. Nos. 5,554,516; 5,716,785; 5,130,238; 5,194,370; 6,090,591; 5,409,818; 5,554,517; 5,169,766; 5,480,784; 5,399,491; 5,679,512; and PCT Pub. No. WO99/42618. For example, a buffer may be Tris buffer, although other buffers can also be used as long as the buffer components are non-inhibitory to enzyme components of the methods of the invention. The pH is preferably from about 5 to about 11, more preferably from about 6 to about 10, even more preferably from about 7 to about 9, and most preferably from about 7.5 to about 8.5. The reaction medium can also include bivalent metal ions such as $Mg^{2+}$ or $Mn^{2+}$, at a final concentration of free ions that is within the range of from about 0.01 to about 15 mM, and most preferably from about 1 to 10 mM. The reaction medium can also include other salts, such as KCl or NaCl, that contribute to the total ionic strength of the medium. For example, the range of a salt such as KCl is preferably from about 0 to about 125 mM, more preferably from about 0 to about 100 mM, and most preferably from about 0 to about 75 mM. The reaction medium can further include additives that could affect performance of the amplification reactions, but that are not integral to the activity of the enzyme components of the methods. Such additives include proteins such as BSA, single strand binding proteins (for e.g., T4 gene 32 protein), and non-ionic detergents such as NP40 or Triton. Reagents, such as DTT, that are capable of maintaining enzyme activities can also be included. Such reagents are known in the art. Where appropriate, an RNase inhibitor (such as Rnasin) that does not inhibit the activity of the RNase employed in the method can also be included. Any aspect of the methods of the invention can occur at the same or varying temperatures. Preferably, the amplification reactions (particularly, primer extension other than the first and second strand cDNA synthesis steps, and strand displacement) are performed isothermally, which avoids the cumbersome thermocycling process. The amplification reaction is carried out at a temperature that permits hybridization of the oligonucleotides (primer and/or PTO) of the invention to the template polynucleotide and primer extension products, and that does not substantially inhibit the activity of the enzymes employed. The temperature can be in the range of preferably about 25° C. to about 85° C., more preferably about 30° C. to about 80° C., and most preferably about 37° C. to about 75° C. In some embodiments that include RNA transcription, the temperature for the transcription steps is lower than the temperature(s) for the preceding steps. In these embodiments, the temperature of the transcription steps can be in the range of preferably about 25° C. to about 85° C., more preferably about 30° C. to about 75° C., and most preferably about 37° C. to about 70° C.

Nucleotide and/or nucleotide analogs, such as deoxyribonucleoside triphosphates, that can be employed for synthesis of the primer extension products in the methods of the invention are provided in the amount of from preferably about 50 to about 2500 μM, more preferably about 100 to about 2000 μM, even more preferably about 200 to about 1700 μM, and most preferably about 250 to about 1500 μM. In some embodiments, a nucleotide or nucleotide analog whose presence in the primer extension strand enhances displacement of the strand (for example, by causing base pairing that is weaker than conventional AT, CG base pairing) is included. Such nucleotide or nucleotide analogs include deoxyinosine and other modified bases, all of which are known in the art. Nucleotides and/or analogs, such as ribonucleoside triphosphates, that can be employed for synthesis of the RNA transcripts in the methods of the invention are provided in the amount of from preferably about 0.25 to about 6 mM, more preferably about 0.5 to about 5 mM, even more preferably about 0.75 to about 4 mM, and most preferably about 1 to about 3 mM.

The oligonucleotide components of the amplification reactions of the invention are generally in excess of the number of target nucleic acid sequence to be amplified. They can be provided at about or at least about any of the following: 10, $10^2$, $10^4$, $10^6$, $10^8$, $10^{10}$, $10^{12}$ times the amount of target nucleic acid. Composite primers and PTO can each be provided at about or at least about any of the following concentrations: 50 nM, 100 nM, 500 nM, 1000 nM, 2500 nM, 5000 nM.

In one embodiment, the foregoing components are added simultaneously at the initiation of the amplification process. In another embodiment, components are added in any order prior to or after appropriate timepoints during the amplification process, as required and/or permitted by the amplification reaction. Such timepoints, some of which are noted below, can be readily identified by a person of skill in the art. The enzymes used for nucleic acid amplification according to the methods of the invention can be added to the reaction mixture either prior to the target nucleic acid denaturation step, following the denaturation step, or following hybridization of the primer to the target RNA, as determined by their thermal stability and/or other considerations known to the person of skill in the art. The first strand cDNA (composite primer extension product) and the second strand cDNA (second primer extension product) synthesis reactions can be performed consecutively, followed by the amplification steps (binding by another composite primer, primer extension and strand displacement). In these embodiments, the reaction conditions and components may be varied between the different reactions.

The amplification process can be stopped at various timepoints, and resumed at a later time. Said timepoints can be readily identified by a person of skill in the art. One timepoint is at the end of first strand cDNA synthesis. Another timepoint is at the end of second strand cDNA synthesis. Methods for stopping the reactions are known in the art, including, for example, cooling the reaction mixture to a temperature that inhibits enzyme activity or heating the reaction mixture to a temperature that destroys an enzyme. Methods for resuming the reactions are also known in the art, including, for example, raising the temperature of the reaction mixture to a temperature that permits enzyme activity or replenishing a destroyed (depleted) enzyme. In some embodiments, one or more of the components of the reactions is replenished prior to, at, or following the resumption of the reactions. For example, it may be necessary to replenish the composite primer prior to beginning the linear amplification reaction if the same composite primer is being used. Alternatively, the reaction can be allowed to proceed (i.e., from start to finish) without interruption.

The reaction can be allowed to proceed without purification of intermediate complexes, for example, to remove primer. Products can be purified at various timepoints, which can be readily identified by a person of skill in the art. One timepoint is at the end of first strand cDNA synthesis. Another timepoint is at the end of second strand cDNA synthesis. We have observed that routine purification of the complex of first and second cDNA results in slightly higher amplification efficiency in subsequent linear amplification steps.

The detection of the amplification product is indicative of the presence of the target sequence. Quantitative analysis is also feasible. Direct and indirect detection methods (including quantitation) are well known in the art. For example, by comparing the amount of product amplified from a test sample containing an unknown amount of a polynucleotide containing a target sequence to the product of amplification of a reference sample that has a known quantity of a polynucleotide that contains the target sequence, the amount of target sequence in the test sample can be determined. The amplification methods of the invention can also be extended to analysis of sequence alterations and sequencing of the target nucleic acid. Further, detection could be effected by, for example, examination of translation products from RNA amplification products.

Compositions and Kits of the Invention

The invention also provides compositions and kits used in the methods described herein. The compositions may be any component(s), reaction mixture and/or intermediate described herein, as well as any combination. For example, the invention provides a composition comprising a composite primer and a second primer, wherein the second primer is a random primer. In some embodiments, the second primer comprises DNA. In other embodiments, the second primer consists of DNA. In still another example, the composition comprises a composite primer and a second primer that comprises a non-target sequence that is included for the purpose of generating displaced primer extension products to which a propromoter polynucleotide can hybridize. This second primer may also be a random primer.

In some embodiments, the composite primer comprises an RNA portion adjacent to the DNA portion. In another embodiment, the composite primer comprises 5'- and 3'-DNA portions with at least one intervening RNA portion. In other embodiments, the composite primer comprises a poly-dT portion. In another example, the invention comprises a composite primer that is a random primer. In some embodiments, the random composite primer or composite primer comprising a poly-dT portion further comprise a portion not hybridizable to a target (under conditions where a portion of the primer hybridizes to target). In other examples, the invention provides a composition comprising a composite primer that is further derivatized by attachment of a moiety capable of effecting attachment of a polynucleotide comprising the composite primer to a solid substrate used in preparing nucleic acid microarrays. In some embodiments, the composite primer is further derivatized by attachment of a positively charged moiety such as an amine.

In some embodiments, the invention provides a composition comprising a composite primer and a polynucleotide comprising a propromoter sequence, such as a PTO (i.e., any of those embodiments described herein). With respect to compositions containing a random primer, these compositions may also contain a plurality of random primers (i.e., a population of random primers having different sequences).

In certain embodiments, the composition comprises (a) a composite primer; (b) a second primer (which can be a random primer); and (c) a reverse transcriptase. In yet other embodiments, the composition comprises (a) a composite primer; (b) a second primer (which can be a random primer); (c) a reverse transcriptase; and (d) a DNA polymerase. In some embodiments, the composition comprises (a) a composite primer; (b) a second primer (which can be a random primer); and (c) a polynucleotide comprising a propromoter sequence (which can be a PTO). Any of the above compositions may further comprise target RNA (which comprises an RNA sequence of interest) and/or any of the enzymes described herein (such as DNA polymerase, for example, reverse transcriptase, RNase H, and/or RNA polymerase). The compositions are generally in lyophilized or aqueous form, preferably in a suitable buffer.

The invention also provides compositions comprising the amplification products described herein. Accordingly, the invention provides a population of DNA or RNA molecules which are copies or the complement of a target sequence, which are produced by any of the methods described herein (or compositions comprising the products).

In another aspect, the invention provides a population of sense polynucleotide (preferably, DNA) molecules and antisense polynucleotide (preferably, DNA) molecules which are copies and complements of a target sequence, which are produced by any of the methods described herein. The invention also includes compositions and various configurations (such as arrays) of these populations, which may be homogeneous (same sequence) or heterogeneous (different sequence). These populations may be any assembly of sequences obtained from the methods described herein, including based on mRNA, as well as certain species or classes of mRNA.

The compositions are generally in a suitable medium, although they can be in lyophilized form. Suitable media include, but are not limited to, aqueous media (such as pure water or buffers).

The invention provides kits for carrying out the methods of the invention. Accordingly, a variety of kits are provided in suitable packaging. The kits may be used for any one or more of the uses described herein, and, accordingly, may contain instructions for any one or more of the following uses: amplifying an RNA sequence; sequencing of an RNA sequence of interest; detection of sequence mutation based on amplifying an RNA sequence (e.g., genotyping or nucleic acid mutation detection); determining presence or absence of a sequence of interest; methods of expression profiling; methods of subtractive hybridization; methods of preparing a subtractive hybridization probe; methods of differential amplification; methods of preparation of libraries (including cDNA and differential expression libraries); methods of preparation of an immobilized nucleic acid (which can be a nucleic acid immobilized on a micro array), and methods of characterizing amplified nucleic acid products generated by the methods of the invention.

The kits of the invention comprise one or more containers comprising any combination of the components described herein, and the following are examples of such kits. A kit may comprise any of the composite primers described herein. In some embodiments, a kit comprises two or more composite primers and second primers, which may or may not be separately packaged. A kit may comprise a composite primer and a polynucleotide comprising a propromoter sequence (which may be a PTO). A kit may further comprise a second primer (which can be a random primer). The composite primer may be labeled or unlabeled. Kits may also optionally further include any of one or more of the enzymes described herein (for example, RNA-dependent DNA polymerase such as reverse transcriptase, and ribonuclease such as RNase H), as well as deoxynucleoside triphosphates (labeled or unlabeled) and/or ribonucleoside triphosphates (labeled or unlabeled). Kits may also include one or more suitable buffers (as described herein). Kits useful for nucleic acid sequencing may optionally include labeled or unlabeled nucleotide analogs that upon incorporation into a primer extension product or RNA transcript effect termination of nucleotide polymerization. One or more reagents in the kit can be provided as a dry powder, usually lyophilized, including excipients, which on dissolution will provide for a reagent solution having the appropriate concentrations for performing any of the methods described herein. Each component can be packaged in separate containers or some components can be combined in one container where cross-reactivity and shelf life permit.

The kits of the invention may optionally include a set of instructions, generally written instructions, although electronic storage media (e.g., magnetic diskette or optical disk) containing instructions are also acceptable, relating to the use of components of the methods of the invention for the intended nucleic acid amplification, and/or, as appropriate, for using the amplification products for purposes such as nucleic acid sequencing and detection of sequence mutation. The instructions included with the kit generally include information as to reagents (whether included or not in the kit) necessary for practicing the methods of the invention, instructions on how to use the kit, and/or appropriate reaction conditions. For example, kits of the invention can comprise: a composite primer (which can comprise a poly-dT portion and/or can be a random primer), a second primer (which can be a random primer), and instructions for using the primers to amplify RNA according to methods of the invention. In another example, kits of the invention comprise a composite primer (which can comprise a poly-dT portion and/or can be a random primer), and instructions for using the primers to amplify RNA according methods of the invention. In another example, kits of the invention comprise: a composite primer, a second primer (which can be a random primer), and instructions for generating double stranded complementary DNA from an RNA target and/or amplifying RNA according to methods of the invention. In yet another example, any of these kits further comprises a propromoter polynucleotide, and instructions for producing a duplex of primer extension product and the propromoter polynucleotide such that a double stranded promoter region is generated and/or amplifying RNA according to methods of the invention. In another example, kits of the invention comprise a composite primer (which can comprise a poly-dT portion, and/or can be a random primer) capable of generating a first strand cDNA, a second composite primer capable of hybridizing to a first strand cDNA, and instructions for using the primers to generate double stranded cDNA according to any of the methods of the invention. In another example, the kits of the invention comprise a double stranded cDNA complex (comprising first and second strand cDNA) comprising a 3' single stranded DNA portion. In yet another example, any of these kits further comprises one or more controls (which can be, for example, RNA template, composite primers, and/or double stranded cDNA complex (comprising first and second strand cDNA) comprising a 3' single stranded DNA portion).

The component(s) of the kit may be packaged in any convenient, appropriate packaging. The components may be packaged separately, or in one or multiple combinations. Where kits are provided for practicing amplification methods of the invention that involve transcription, the RNA polymerase (if included) is preferably provided separately from the components used in the steps prior to the transcription steps.

The relative amounts of the various components in the kits can be varied widely to provide for concentrations of the reagents that substantially optimize the reactions that need to occur to practice the methods disclosed herein and/or to further optimize the sensitivity of any assay.

The invention also provides systems for effecting the methods described herein. These systems comprise various combinations of the components discussed above. For example, in some embodiments, the invention provides a system suitable for producing target polynucleotide sequence (or amplifying target polynucleotide sequence) comprising (a) a composite primer (any of those described herein), (b) DNA polymerase; and (c) ribonuclease. In some embodiments, the system further comprises a polynucleotide comprising a propromoter sequence (which may be a PTO) and a DNA-dependent RNA polymerase. In other embodiments, the system further comprises an RNA-dependent DNA polymerase. Any of the systems embodiments may also comprise a template (target) sequence, as described herein. A system generally includes one or more apparatuses for performing the amplification methods of the invention. Such apparatuses include, for example, heating devices (such as heating blocks or water baths) and apparatuses which effect automation of one or more steps of the methods described herein. The methods of the invention are particularly suitable for use with miniaturized devices, as thermal cycling is not required for any of the steps. A non-limiting example of suitable devices includes the BioAnalyzer (Agilant and Caliper) and the eSensor.

The invention also provides reaction mixtures (or compositions comprising reaction mixtures) which contain various combinations of components described herein. Examples of reaction mixtures have been described. In some embodiments, the invention provides reaction mixtures comprising (a) a target RNA; (b) a composite primer comprising a 3' DNA portion and an RNA portion; (c) a second primer; and (d) DNA polymerase. As described herein, any of the composite primers may be in the reaction mixture (or a plurality of composite primers), including a composite primer that comprises a 5' RNA portion which is adjacent to the 3' DNA portion. The reaction mixture could also further comprise an enzyme which cleaves RNA from an RNA/DNA hybrid, such as RNase H. A reaction mixture of the invention can also further comprise a polynucleotide comprising a propromoter sequence as described herein. Another example of a reaction mixture is (a) a displaced primer extension product (and, as such, contains at its 5' end a sequence complementary to the 3' DNA portion of the composite primer, but not a sequence complementary to the RNA portion of the composite primer); (b) a polynucleotide comprising a propromoter sequence (for example, a PTO); and (c) RNA polymerase. Other reaction mixtures are described herein and are encompassed by the invention.

The invention also includes compositions comprising any of the complexes (which are intermediates in the methods described herein) described herein. Examples of such complexes are schematically depicted in FIGS. 1-8. As an example, one complex of the invention is a complex comprising: (a) a target RNA strand; and (b) a composite primer, said composite primer comprising a 3' DNA portion and an RNA portion. The composite primer may have an RNA portion which is 5' and adjacent to the 3" DNA portion. As another example, a complex of the invention is a complex comprising: (a) a composite primer extension product; and (b) a target RNA strand. In still another example, a complex of the invention is a complex comprising: (a) a first primer extension product, wherein the first primer is a composite primer comprising an RNA portion and a 3' DNA portion; and (b) a second primer. In again another example, a complex of the invention is a complex comprising: (a) a first primer extension product, wherein the first primer is a composite primer comprising an RNA portion and a 3' DNA portion; and (b) a second primer extension product. In yet another example, a complex of the invention is a complex comprising: (a) a displaced primer extension product, wherein the primer is a composite primer comprising an RNA portion and a 3' DNA portion; and (b) a propromoter polynucleotide (such as a PTO).

In yet another example, a complex of the invention is a double stranded cDNA complex further comprising a RNA/DNA portion at one end, prepared by any of the methods described herein. In some embodiments, the double stranded cDNA complex further comprises a second RNA/DNA portion at a second end. In yet another example, the complex of the invention is a first and second primer extension product comprising a 3' single stranded DNA portion comprising a 3' single stranded DNA portion produced by any of the methods described herein. In some embodiments, the composition further comprises a second 3' single stranded region. In another example, the complex of the invention is (a) a complex of first and second primer extension product comprising a 3' single stranded DNA portion, and (b) a composite primer hybridized to second primer extension product. In another example, the complex of the invention is a complex of a first strand cDNA and a second strand cDNA (that is generated by extension along first strand cDNA of a primer). In some embodiments, the primer comprises a fragment of template RNA hybridized to the first strand cDNA. In some embodiment, the primer is DNA.

Methods Using the Amplification Methods and Compositions of the Invention

The methods and compositions of the invention can be used for a variety of purposes. For purposes of illustration, methods of sequencing, genotyping (nucleic acid mutation detection), determining the presence or absence of a sequence of interest, preparation of an immobilized nucleic acid (which can be a nucleic acid immobilized on a microarray), and characterizing nucleic acids using the amplified nucleic acid products generated by the methods of the invention, are described. Methods of expression profiling, methods of subtractive hybridization and the preparation of probes for subtractive hybridization, and methods of preparing libraries (which can be cDNA and/or differential hybridization libraries) are also described.

Sequencing of RNA Targets Using the Methods of the Invention

The amplification methods of the invention are useful, for example, for sequencing of an RNA sequence of interest. The sequencing process is carried out by amplifying a target RNA containing the sequence of interest by any of the methods described herein. Addition of nucleotides during primer extension is analyzed using methods known in the art, for example, incorporation of a terminator nucleotide or sequencing by synthesis (e.g. pyrosequencing).

In embodiments wherein the end product is in the form of displaced DNA primer extension products, in addition to the nucleotides, such as natural deoxyribonucleotide triphosphates (dNTPs), that are used in the amplification methods, appropriate nucleotide triphosphate analogs, which may be labeled or unlabeled, that upon incorporation into a primer extension product effect termination of primer extension, may be added to the reaction mixture. Preferably, the dNTP analogs are added after a sufficient amount of reaction time has elapsed since the initiation of the amplification reaction such that a desired amount of second primer extension product or fragment extension product has been generated. Said amount of the time can be determined empirically by one skilled in the art.

In embodiments wherein the end product is in the form of RNA products, sequencing can be based on premature (deliberate) termination of RNA transcription. The inclusion of rNTP analogs, which may be labeled or unlabeled, that upon incorporation into an RNA transcript effects termination of rNTP polymerization in the reaction mixture, will result in production of truncated RNA products, which result from blocking of the RNA polymerase at sites of incorporation of the analogs.

Suitable analogs (dNTP and rNTP) include those commonly used in other sequencing methods and are well known in the art. Examples of dNTP analogs include dideoxyribonucleotides. Examples of rNTP analogs (such as RNA polymerase terminators) include 3'-dNTP. Sasaki et al., Biochemistry (1998) 95:3455-3460. These analogs may be labeled, for example, with fluorochromes or radioisotopes. The labels may also be labels which are suitable for mass spectroscopy. The label may also be a small molecule which is a member of a specific binding pair, and can be detected following binding of the other member of the specific binding pair, such as biotin and streptavidin, respectively, with the last member of the binding pair conjugated to an enzyme that catalyzes the generation of a detectable signal that could be detected by methods such as colorimetry, fluorometry or chemiluminescence. All of the above examples are well known in the art. These are incorporated into the primer extension product or RNA transcripts by the polymerase and serve to stop further extension along a template sequence. The resulting truncated polymerization products are labeled. The accumulated truncated products vary in length, according to the site of incorporation of each of the analogs, which represent the various sequence locations of a complementary nucleotide on the template sequence.

Analysis of the reaction products for elucidation of sequence information can be carried out using any of various methods known in the art. Such methods include gel electrophoresis and detection of the labeled bands using appropriate scanner, sequencing gel electrophoresis and detection of the radiolabeled band directly by phosphorescence such as Molecular Dynamics reader, capillary electrophoresis adapted with a detector specific for the labels used in the reaction, and the like. The label can also be a ligand for a binding protein which is used for detection of the label in combination with an enzyme conjugated to the binding protein, such as biotin-labeled chain terminator and streptavidin conjugated to an enzyme. The label is detected by the enzymatic activity of the enzyme, which generates a detectable signal. As with other sequencing methods known in the art, the sequencing reactions for the various nucleotide types (A, C, G, T or U) are carried out either in a single reaction vessel, or in separate reaction vessels (each representing 1 of the various nucleotide types). The choice of method to be used is dependent on practical considerations readily apparent to one skilled in the art, such as the nucleotide tri phosphate analogs and/or label used. Thus, for example, when each of the analogs is differentially labeled, the sequencing reaction can be carried out in a single vessel. The considerations for choice of reagent and reaction conditions for optimal performance of sequencing analysis according to the methods of the invention are similar to those for other previously described sequencing methods. The reagent and reaction conditions should be as described above for the nucleic acid amplification methods of the invention.

Mutation Detection, Including Mutation Detection Based on Single Stranded Conformation Polymorphism Utilizing the Amplification Methods of the Invention The DNA or RNA amplification products generated according to the methods of the invention are also suitable for analysis for the detection of any alteration in the target nucleic acid sequence, as compared to a reference nucleic acid sequence which is identical to the target nucleic acid sequence other than the sequence alteration. The sequence alterations may be sequence alterations present in the genomic sequence or may be sequence alterations which are not reflected in the genomic DNA sequences, for example, alterations due to post transcriptional alterations, and/or mRNA processing, including splice variants. Sequence alterations (interchangeably called "mutations") include deletion, substitution, insertion and/or transversion of one or more nucleotide.

The DNA or RNA products of the amplification methods are suitable for single stranded conformation polymorphism (SSCP or rSSCP) based mutation detection. The amplification methods of the invention can be directly linked to appropriate means for detecting single stranded conformation polymorphism, such as an electrophoretic separation method for the identification of specific mobility pattern of the single stranded DNA or RNA products for the elucidation of the presence of specific sequence feature(s), and/or the presence of any difference in a test nucleic acid as compared to a reference nucleic acid.

Methods based on gel electrophoresis or capillary electrophoresis can be used for the detection and analysis of the various single stranded conformational isomers. Alternatively, it is also likely that cleavage of the single stranded DNA or RNA product using nucleases which recognize sequence dependent secondary structures may be useful for the determination of sequence specific conformation polymorphism. Such nucleases are known in the art, such as the Cleavase assay (Third Wave). The electrophoretic methods are potentially more suitable for high throughput mutation, or genotyping, detection methods.

The determination of sequence specific electrophoretic pattern for a given nucleic acid sequence is useful for, for example, the detection of specific alleles of a test sequence. Furthermore, it is expected that an electrophoretic mobility pattern for the various alleles could be well differentiated, thus allowing the detection of two alleles in a nucleic acid sample from a single individual, as required for heterozygous genotype, or multiple alleles. Any alteration in the test nucleic acid sequence, such as base substitution, insertions or deletion, could be detected using this method. The method is expected to be useful for detection of specific single base polymorphism, SNP, and the discovery of new SNPs. Thus, the invention also provides methods for detecting a polynucleotide comprising a single nucleotide polymorphism, comprising: (a) amplifying a target polynucleotide using any of the methods described herein; and (b) analyzing the amplification products for single stranded conformation, wherein a difference in conformation as compared to a reference single stranded polynucleotide indicates a single nucleotide polymorphism in the target polynucleotide, whereby a polynucleotide comprising a single nucleotide polymorphism is detected.

Other art recognized methods of analysis for the detection of any alteration in the target nucleic acid sequence, as compared to a reference nucleic acid sequence, are suitable for use with the single stranded nucleic acid products of the amplification methods of the invention. Such methods are well-known in the art, and include various methods for the detection of specific defined sequences including methods based on allele specific primer extension, allele specific probe ligation, differential probe hybridization, and limited primer extension. See, for example, Kurn et al, U.S. Pat. No. 6,251,639 B1; U.S. Pat. Nos. 5,888,819; 6,004,744; 5,882,867; 5,854,033; 5,710,028; 6,027,889; 6,004,745; 5,763,178; 5,011,769; 5,185,243; 4,876,187; 5,882,867; 5,731,146; WO US88/02746; WO 99/55912; WO92/15712; WO 00/09745; WO 97/32040; WO 00/56925; and U.S. Pat. No. 5,660,988. Thus, the invention also provides methods for detection of a mutation in an RNA sequence of interest comprising a single nucleotide polymorphism, comprising: (a) amplifying a target RNA using any of the methods described herein; and (b) analyzing the amplification products for presence of an alteration (mutation) as compared to a reference single stranded polynucleotide.

Methods of Determining the Presence or Absence of a Sequence of Interest

The unique properties of the second composite primer for use in the isothermal amplification methods of the invention provide the basis for an isothermal method for the detection of defined mutations (defined in the sense that location of the mutation is defined), or polymorphic sites (such as SNPs), in a target nucleic acid sequence. The method is useful for genotyping, detection of mutation leading to drug resistance and the like.

The RNA portion(s) of the composite primer is designed to be hybridizable to the sequence of the test target RNA in which the presence of a sequence alteration is suspected. Stated alternatively, the primer comprises an RNA portion(s) that comprises a sequence that is hybridizable to the reference RNA sequence (for example, a wild type sequence) against which the sequence in the test target RNA is to be compared. In some embodiments, the altered sequence (i.e., the sequence comprising a sequence alteration) and the reference sequence are alleles. The sequence alteration may be a single nucleotide substitution, a deletion or insertion.

In another embodiment, the RNA portion(s) of the composite primer is designed to be hybridizable to the altered sequence suspected to be present in the test target RNA. Stated alternatively, the primer comprises an RNA portion(s) that comprises a sequence that is hybridizable to the test target RNA, and thus is not hybridizable to the reference sequence (for example, a wild type sequence) against which the sequence in the test target RNA is to be compared. In some embodiments, the altered sequence (i.e., the sequence comprising a sequence alteration) and the reference sequence are alleles.

The RNA portion, generally 5' RNA portion, of the composite primer comprises a sequence which is hybridizable to a known normal wild type sequence, or a known mutant or a polymorphic genotype. Generally, a suitable composite primer comprises an RNA portion that allows the primer to preferentially hybridize to a target nucleic acid if the target nucleic sequence comprises a sequence hybridizable to the RNA portion of the primer compared to if there is a mismatch (i.e., the primer has the mutated sequence and the target does not, or vice versa), wherein the target nucleic acid has a bound primer extension product and has had its 5'-RNA portion cleaved. The presence of sequence alteration does not generally prevent the initial step of the amplification methods, such that a double stranded complex of first and second primer extension products comprising RNA/DNA heteroduplex. A ribonuclease, such as RNase H, then cleaves the RNA portion of the RNA/DNA heteroduplex. While it is likely that the presence of a mismatched base pair will affect the pattern of cleavage of the RNA/DNA hybrid, the cleavage is nonetheless likely to take place. The next step of binding of another composite primer to the complex by hybridization of the 5' RNA portion will be inhibited, preferably prevented, by a mismatch. This effect is dependent on factors such as the size of the hybridizing oligonucleotide and the stringency of the reaction condition. These factors are considered in the design of the composite primer, according to techniques well known and routine in the art. It is also possible that the mismatch will inhibit cleavage of the RNA portion(s) of the composite primer, thus preventing the amplification of the second primer extension product. Another possibility is that the mismatch will result in lower efficiency of cleavage of the RNA portion of the primer thus resulting in lower efficiency of amplification or production of less amplification product. The inability of the composite primer to hybridize to the target at this step of the amplification prevents further steps of primer extension strand displacement and production of multiple copies of the amplification products. It is understood that the detection of mutation by the methods of the present invention can be based on absence or presence of single stranded amplification products, or quantitative comparisons of amount of accumulated primer extension product. For example, when the composite primer comprises the reference sequence (for example, wild type), the presence of a mutation in a target strand may lead to no detectable amplification products; alternatively, it may lead to detectable products, but less than those produced from a template strand without the mutation.

When the composite primer comprises an RNA portion, generally a 5' RNA portion, that is fully hybridizable to a mutant genotype, amplification of a sequence which is of the normal genotype will be prevented, while a mutant genotype target will be amplified. Thus, in this case the detection and/or quantitative determination of multiple copies of the amplification product will be indicative of the presence of a target sequence of the mutant genotype. For example, parallel reactions that include either the nucleic acid sample of interest or reference sample of target nucleic with a wild type sequence could be run. Accumulation of more primer extension products in the former compared to the latter reaction would be indicative of the presence of a mutant genotype in the sample of interest. Alternatively, when the composite primer comprises a 5' RNA sequence that is fully hybridizable to a normal genotype sequence of the test target, amplification of a target sequence of the mutant genotype is prevented, and the detection and/or quantitative determination of amplification products is indicative of a normal genotype.

Any of the amplification methods of the present invention are suitable for detection of mutation as described above.

Accordingly, the invention provides a method of determining presence or absence of a sequence of interest, said method comprising (i) amplifying a target RNA containing the sequence of interest, said amplification comprising extending a composite primer hybridized to cleaved complex of first and second primer extension product prepared by any of the methods described herein, wherein the sequence of the RNA portion of the composite primer is known, and (ii) comparing the amplification products if any from step (i) with the amount of amplification products from a reference template wherein (1) production of detectably fewer amplification products from the template as compared to the amount of amplification products from the reference template which comprises a region hybridizable to the RNA portion of the composite primer indicates that the second primer extension product does not comprise a sequence hybridizable to the RNA portion of the composite primer and is a sequence variant with respect to the sequence hybridizable to the RNA portion of the composite primer; or (2) production of detectably more amplification products from the template as compared to the amount of amplification products from the reference template which does not comprise a region which is hybridizable to the RNA portion of the composite primer indicates that the second primer extension product comprises a sequence hybridizable to the RNA portion of the composite primer and is not a sequence variant with respect to the sequence hybridizable to the RNA portion of the composite primer.

Method of Preparing Nucleic Acids Immoblized to a Substrate, Including a Microarray of Nucleic Acids The single stranded products of some of the amplification methods of the invention are suitable for immobilizing to a surface. The single stranded products are particularly suitable for preparing microarrays comprising the single stranded amplification products.

Single stranded amplification products can be attached to a solid or semi-solid support or surface, which may be made, e.g., from glass, plastic (e.g., polystyrene, polypropylene, nylon), polyacrylamide, nitrocellulose, or other materials.

Several techniques are well-known in the art for attaching nucleic acids to a solid substrate such as a glass slide. One method is to incorporate modified bases or analogs that contain a moiety that is capable of attachment to a solid substrate, such as an amine group, a derivative of an amine group or another group with a positive charge, into the amplified nucleic acids. The amplified product is then contacted with a solid substrate, such as a glass slide, which is coated with an aldehyde or another reactive group which will form a covalent link with the reactive group that is on the amplified product and become covalently attached to the glass slide. Microarrays comprising the amplified products can be fabricated using a Biodot (BioDot, Inc. Irvine, Calif.) spotting apparatus and aldehyde-coated glass slides (CEL Associates, Houston, Tex.). Amplification products can be spotted onto the aldehyde-coated slides, and processed according to published procedures (Schena et al., *Proc. Natl. Acad. Sci. U.S.A.* (1995) 93:10614-10619). Arrays can also be printed by robotics onto glass, nylon (Ramsay, G., *Nature Biotechnol.* (1998), 16:40-44), polypropylene (Matson, et al., *Anal Biochem.* (1995), 224(1):110-6), and silicone slides (Marshall, A. and Hodgson, J., *Nature Biotechnol.* (1998), 16:27-31). Other approaches to array assembly include fine micropipetting within electric fields (Marshall and Hodgson, supra), and spotting the polynucleotides directly onto positively coated plates. Methods such as those using amino propyl silicon surface chemistry are also known in the art, as disclosed at http://www.cmt.corning.com and http://cmgm.stanford.edu/pbrown/.

One method for making microarrays is by making high-density polynucleotide arrays. Techniques are known for rapid deposition of polynucleotides (Blanchard et al., *Biosensors & Bioelectronics*, 11:687-690). Other methods for making microarrays, e.g., by masking (Maskos and Southern, *Nuc. Acids. Res.* (1992), 20:1679-1684), may also be used. In principle, and as noted above, any type of array, for example, dot blots on a nylon hybridization membrane, could be used. However, as will be recognized by those skilled in the art, very small arrays will frequently be preferred because hybridization volumes will be smaller.

The amplified polynucleotides may be spotted as a matrix on substrates comprising paper, glass, plastic, polystyrene, polypropylene, nylon, polyacrylamide, nitrocellulose, silicon, optical fiber or any other suitable solid or semi-solid (e.g., thin layer of polyacrylamide gel (Khrapko, et al., *DNA Sequence* (1991), 1:375-388) surface.

An array may be assembled as a two-dimensional matrix on a planar substrate or may have a three-dimensional configuration comprising pins, rods, fibers, tapes, threads, beads, particles, microtiter wells, capillaries, cylinders and any other arrangement suitable for hybridization and detection of target molecules. In one embodiment the substrate to which the amplification products are attached is magnetic beads or particles. In another embodiment, the solid substrate comprises an optical fiber. In yet another embodiment, the amplification products are dispersed in fluid phase within a capillary which, in turn, is immobilized with respect to a solid phase.

Characterization of Nucleic Acids

The amplification products obtained by the methods of the invention are amenable to further characterization. The single stranded nature of some products of the methods facilitates characterization. The methods of the invention producing single stranded products are particularly amenable to quantitative analysis, as sufficient single stranded DNA and RNA products are produced which generally accurately reflect the representation of the various mRNA in the starting material.

The amplified polynucleotide products, either DNA or RNA (i.e., products of any of the amplification methods described herein), can be analyzed using, for example, probe hybridization techniques known in the art, such as Southern and Northern blotting, and hybridizing to probe arrays. They can also be analyzed by electrophoresis-based methods, such as differential display and size characterization, which are known in the art. In addition, the single stranded DNA and RNA products may serve as starting material for other starting material for other analytical and/or quantification methods known in the art, such as real time PCR, quantitative TaqMan, quantitative PCR using molecular beacons, methods described in Kurn, U.S. Pat. No. 6,251,639, etc. Thus, the invention includes those further analytical and/or quantification methods as applied to any of the products of the methods herein.

In one embodiment, the amplification methods of the invention are utilized to generate multiple copies of single stranded products, and analyzing single stranded products by contact with a probe.

In one embodiment, the amplification methods of the invention are utilized to generate multiple copies of single stranded polynucleotide (generally, DNA) products that are labeled by using composite primers that are labeled (in the portion(s) that is not cleaved). In another embodiment, the amplification methods of the invention are utilized to generate multiple copies of single stranded polynucleotide (DNA or RNA) products that are labeled by the incorporation of labeled nucleotides during DNA or RNA polymerization. For example, amplification according to the methods of the invention can be carried out with suitable labeled dNTPs or rNTPs. These labeled nucleotides can be directly attached to a label, or can comprise a moiety which could be attached to a label. The label may be attached covalently or non-covalently to the amplification products. Suitable labels are known in the art, and include, for example, a ligand which is a member of a specific binding pair which can be detected/quantified using a detectable second member of the binding pair. Thus, amplification of total mRNA according to the methods of the invention in the presence of, for example, Cy3-dUTP or Cy5-dUTP results in the incorporation of these nucleotides into the amplification products.

The labeled amplified products are particularly suitable for analysis (for example, detection and/or quantification) by contacting them with, for example, microarrays (of any suitable surface, which includes glass, chips, plastic), beads, or particles, that comprise suitable probes such as cDNA and/or oligonucleotide probes. Thus, the invention provides methods to characterize (for example, detect and/or quantify) an RNA sequence of interest by generating labeled polynucleotide (generally, DNA or RNA) products using amplification methods of the invention, and analyzing the labeled products. Analysis of labeled products can be performed by, for example, hybridization of the labeled amplification products to, for example, probes immobilized at, for example, specific locations on a solid or semi-solid substrate, probes immobilized on defined particles, or probes immobilized on blots (such as a membrane), for example arrays, which have been described above. Other methods of analyzing labeled products are known in the art, such as, for example, by contacting them with a solution comprising probes, followed by extraction of complexes comprising the labeled amplification products and probes from solution. The identity of the probes provides characterization of the sequence identity of the amplified products, and thus by extrapolation the identity of the target RNA present in a sample. Hybridization of the labeled products is detectable, and the amount of specific labels that are detected is proportional to the amount of the labeled amplification products of a specific RNA sequence of interest. This measurement is useful for, for example, measuring the relative amounts of the various RNA species in a sample, which are related to the relative levels of gene expression, as described herein. The amount of labeled products (as indicated by, for example, detectable signal associated with the label) hybridized at defined locations on an array can be indicative of the detection and/or quantification of the corresponding target RNA species in the sample.

In another aspect, the invention provides a method of quantitating single stranded polynucleotide (generally, DNA or RNA) comprising use of an oligonucleotide (probe) of defined sequence (which may be immobilized, for example, on a microarray). In this aspect of the invention, labeled single stranded polynucleotide (generally, DNA or RNA) products comprising defined sequences at the 5' and/or 3' ends (introduced using tailed first or second primers, as described herein) are hybridizable to a defined oligonucleotides, wherein the oligonucleotide comprises the complement of the defined sequence introduced at the 5' and/or 3' end). In some embodiments, specific mRNA species are amplified using a composite and/or second primer tailed with a defined sequence that is hybridizable to a sequence immobilized on the array (depending whether the defined sequence is introduced in the composite or second primer). For example, in one embodiment, a first composite primer comprises a 3' portion which is hybridizable to a sequence of a specific RNA species, and a 5' portion that is not hybridizable to a specific RNA template, but is hybridizable to a defined oligonucleotide. In another embodiment, a second primer comprises a 3' portion which is hybridizable to a sequence of a first primer extension product, and a 5' portion that is not hybridizable to a first primer extension product, but comprises a sequence of a defined oligonucleotide. Multiple copies of single stranded labeled DNA or RNA products are produced which are hybridizable to oligonucleotide. It is understood that although a single RNA species is discussed above, multiple species may be amplified simultaneously, each with a composite primer or second primer comprising a tail hybridizable to a different defined oligonucleotide.

Determination of Gene Expression Profile

The amplification methods of the invention are particularly suitable for use in determining the levels of expression of one or more genes in a sample since the methods described herein are capable of amplifying one or more, preferably a plurality of target RNAs in the same sample. As described above, amplification products can be detected and quantified by various methods, as described herein and/or known in the art. Since RNA is a product of gene expression, the levels of the various RNA species, such as mRNAs, in a sample is indicative of the relative expression levels of the various genes (gene expression profile). Thus, determination of the amount of RNA sequences of interest present in a sample, as determined by quantifying amplification products of the sequences, provides for determination of the gene expression profile of the sample source.

Accordingly, the invention provides methods of determining gene expression profile in a sample, said method comprising: amplifying single stranded product from at least one RNA sequence of interest in the sample, using any of the methods described herein; and determining amount of amplification products of each RNA sequence of interest, wherein each said amount is indicative of amount of each RNA sequence of interest in the sample, whereby the expression profile in the sample is determined. Generally, labeled products are generated. In one embodiment, the target RNA is mRNA. In yet another embodiment, the composite primer comprises a poly-dT sequence (such that in RNA in a sample is amplified). It is understood that amount of amplification product may be determined using quantitative and/or qualitative methods. Determining amount of amplification product includes determining whether amplification product is present or absent. Thus, an expression profile can includes information about presence or absence of one or more RNA sequence of interest. "Absent" or "absence" of product, and "lack of detection of product" as used herein includes insignificant, or de minimus levels.

The methods of expression profiling are useful in a wide variety of molecular diagnostic, and especially in the study of gene expression in essentially any mammalian cell (including a single cell) or cell population. A cell or cell population (e.g. a tissue) may be from, for example, blood, brain, spleen, bone, heart, vascular, lung, kidney, pituitary, endocrine gland, embryonic cells, tumors, or the like. Expression profiling is also useful for comparing a control (normal) sample to a test sample, including test samples collected at different times, including before, after, and/or during development, a treatment, and the like.

Method of Preparing a Library

The single stranded DNA and RNA products of the methods of the invention are useful in preparing libraries, including cDNA libraries and subtractive hybridization libraries. Using the methods of the invention, libraries may be prepared from limited amount of starting material, for example, mRNA extracted from limited amount of tissue or even single cells. Accordingly, in one aspect, the methods of the invention provides preparing a library from the single stranded DNA or RNA products of the invention. In another aspect, the invention provides methods of preparing a library from the double stranded cDNA produced by the methods of the invention comprising two composite primers. Method for preparing libraries from double stranded cDNA are well known in the art. In still another aspect, the invention provides methods for making a library, said method comprising: preparing a subtractive hybridization probe using any of the methods described herein.

In some embodiments, the first composite primer is hybridizable to the poly-A sequence found in essentially all mRNAs. In other embodiments, the first composite primer is a random primer.

Methods of Subtractive Hybridization

The amplification methods of the invention are particularly suitable for use in subtractive hybridization methods, in which (at least) a first and second target RNA population is compared, since the methods described herein are capable of amplifying multiple target RNAs in the same sample, and the methods of the invention are suitable for producing large amounts of single stranded antisense nucleic acid suitable for use as "driver" in subtractive hybridization. For example, two nucleic acid populations, one sense and one antisense, can be allowed to mix together with one population present in molar excess ("driver"). Sequence present in both populations will form hybrids, while sequences present in only one population remain single-stranded. Thereafter, various well known techniques are used to separate the unhybridized molecules representing differentially expressed sequences. See, e.g., Hamson et al., U.S. Pat. No. 5,589,339; Van Gelder, U.S. Pat. No. 6,291,170.

Accordingly, the invention provides methods for performing subtractive hybridization, said methods comprising: (a)

preparing multiple DNA copies of the complement of at least one RNA sequences of interest from a first RNA population using any of the amplification methods described herein; and (b) hybridizing the multiple copies to a second mRNA population, whereby a subpopulation of the second mRNA population forms a complex with a nucleotide DNA copy. The invention also provides methods for performing subtractive hybridization, said methods comprising: hybridizing multiple copies of the complement of at least one RNA sequences of interest from a first RNA population using any of the amplification methods described herein to a second mRNA population, whereby a subpopulation of the second mRNA population forms a complex with a copy. In some embodiments, "driver" single stranded anti-sense DNA product of the methods of the invention is combined with tester (sense) mRNA species. In some embodiments, "driver" single stranded antisense nucleic acid (generally, DNA) product is produced using the methods of the invention described herein, and a first composite primer hybridizable to the poly-A sequence (amplifying essentially all mRNA species). In other embodiment, the first composite primer is a random primer.

In another aspect, the invention provides methods of differential amplification in which single stranded driver (anti-sense) DNA sequences that hybridize with tester mRNA sequence are subjected to cleavage by an agent that cleaves RNA present in a DNA/RNA hybrid, such as RNase H. Cleavage of the mRNA results in the inability to generate single stranded DNA product from the test mRNA strands. Conversely, non-cleaved tester (i.e., tester mRNA that did not hybridize to driver DNA molecules) may serve as a substrate for subsequent amplification. Amplified differentially expressed products have many uses, including as a differential expression probe, to produce differential expression libraries Accordingly, the invention provides methods for differential amplification of one or more RNA sequence of interest, said method comprising: (a) preparing multiple polynucleotide (generally, DNA) copies of the complement of at least one RNA sequences of interest from a first RNA population using any of the amplification methods described herein; (b) hybridizing the multiple copies to a second mRNA population, whereby a subpopulation of the second mRNA population forms a complex with a DNA copy; (c) cleaving RNA in the complex of step (b) with an enzyme that cleaves RNA from an RNA/DNA hybrid; and (d) amplifying an unhybridized subpopulation of the second mRNA population, whereby multiple copies of single stranded DNA complementary to the unhybridized subpopulation of the second mRNA population are generated. In some embodiments, step (d) is performed using any of the amplification methods described herein. In some embodiments, the methods comprise hybridizing multiple polynucleotide (generally, DNA) copies of the complement of at least one RNA sequences of interest from a first RNA population using any of the amplification methods described herein to a second mRNA population, whereby a subpopulation of the second mRNA population forms a complex with a DNA copy; (b) cleaving RNA in the complex of step (a) with an enzyme that cleaves RNA from an RNA/DNA hybrid; and (c) amplifying an unhybridized subpopulation of the second mRNA population, whereby multiple copies of single stranded DNA complementary to the unhybridized subpopulation of the second mRNA population are generated.

The following Examples are provided to illustrate, but not limit, the invention.

EXAMPLES

Example 1

Amplification of Total Poly-A mRNA

Poly-A mRNA from MOLT-4 cell line (CLONTECH 6587-1) was used as a target for amplification. The process of amplification was in three steps: 1) synthesis of first cDNA strand; 2) synthesis of second cDNA strand to produce a double stranded cDNA from the total mRNA of the sample; and 3) amplification of the total mRNA. The double stranded cDNA product comprises at one end an RNA/DNA heteroduplex, which is a substrate for RNase H. The sequence of the two strands of this heteroduplex portion is not related to the target, and is incorporated through utilization of a composite (first) primer.

Primer Sequences:

```
                                           (SEQ ID NO: 1)
MTA1:  GACGGAUGCGGUCUTTTTTTT (SEQ ID NO: 2)
MTA2:  GACGGAUGCGGUCUTTTTTTTN (SEQ ID NO: 3)
MTA3:  GACGGAUGCGGUCUTTTTTTTNN
``` wherein italicized nucleotides denote ribonucleotides and "N" denotes a degenerate nucleotide (i.e., it can be A, T, C or G).

Step 1: Synthesis of the First Strand cDNA from Poly A mRNA 0.1 µg of total poly-A mRNA was mixed with the following reagents in a total volume of 10 ul:
 0.2 µl primer MTA3 (100 µM)
 0.5 µl dNTPs (25 mM)
 0.1 µl Rnasin
 0.1 µl DTT
 2 µl 5× AMV reverse transcriptase reaction buffer
 DEPC treated water to 10 µl total volume The reaction mixture was incubated for 2 min at 75° C., and then cooled to 37° C. 1 µl AMV reverse transcriptase (USB 70041Y, 15 U/µl) was added to each reaction and the reaction mixture was further incubated at this temperature for 60 min.

Step 2: Second Strand cDNA Synthesis

The first strand cDNA reaction mixture was mixed with 10 µl of the second strand cDNA synthesis mixture containing the following:
 1 µl 10× Klenow reaction buffer
 0.1 µl dNTPs (25 mM)
 0.5 µl Klenow (USB 2141Y 5 U/µl) DNA polymerase
 8.4 µl water The reaction mixture was incubated for 30 min at 37° C., followed by heating to 75° C. for 5 min to stop the reactions by inactivating the enzymes.

Step 3: Amplification of Total cDNA

Two composite primers were tested—MTA1 and MTA2.

The reactions were carried out in a total volume of 20 comprising the following:
 1 µl cDNA reaction
 0.2 µl MTA1 or MTA2 primer (both are at 100 µM)
 0.2 µl 25 mM dNTPs
 0.1 µl Rnasin
 0.1 µl DTT
 17.2 µl water The mixture above was incubated at 94° C. for 20 seconds and then cooled to 50° C. A mixture of 2 U BCA, 0.02 U Hybridase (RNase H) and 0.4 μg T4 Gene 32 protein (single stranded DNA binding protein) was added, and the reaction mixture was incubated at 50° C. for 60 min.

5 μl of each reaction mixture was analyzed by electrophoresis on 5-20% PAGE (Novex). Successful amplification was indicated by the reaction products of the amplified total mRNA appearing as a smear, which was expected due to amplification of a plurality of mRNA species. No product was observed in reactions carried out without one of the following components: a. input double stranded cDNA; b. primer for first strand synthesis; and c. input mRNA for the first strand cDNA synthesis.

Example 2

Characterization of Products of Step 2 and Step 3 Reactions of Example 1

In the amplification reactions of Example 1, a "unique" sequence (i.e., a sequence not hybridizable to the RNA template) is expected to be created at the 3'-end of the second strand cDNA due to the "unique" sequence of the 5' RNA portion of the composite primer used. This sequence (of the 3'-end of the second strand cDNA) is complementary to the 5'-RNA portion of the composite primer and is not related to sequences in the target RNA. To determine the presence of this sequence in the second strand cDNA that is obtained, PCR amplification of the reaction products (as found in reaction mix of step 2 of Example 1) was performed using a primer which is complementary to the expected sequence at the 3'-end of the second strand cDNA, as a forward primer, and a G3PDH-specific primer as a reverse PCR primer. This primer pair would be expected to amplify a specific product from a double stranded cDNA that has the "unique" sequence. It would not, however, be expected to generate a specific product from PCR amplification of the anti-sense DNA products (as found in the reaction mix of step 3 of Example 1), because these products would not be expected to contain the "unique" sequence (which is introduced by the RNA portion of the composite primer which is cleaved by RNase H). Since the reaction mix of step 3 of Example 1 contains predominantly amplified DNA products (that should not contain the "unique" sequence), PCR amplification of this reaction mix would be expected to be much less efficient (and thus generate substantially less products) than PCR amplification of the reaction mix of step 2 (which contains primarily double stranded cDNA product).

PCR reactions were carried out as follows:
Each 50 μl of PCR reaction contains:
0.4 μM of each primer (Biosource International)
100 μM of each dNTP (Epicenter)
2 mM Magnesium chloride (Epicenter)
1-2 units Polymerase (either MasterAmp taq or MasterAmp Tfl, both from Epicenter)
5 μl 10× buffer as supplied with the enzyme.
Either 0.5 μl of a linear amplification reaction from the third step in Example 1, or a 1:20 dilution of the cDNA generated in step 2 in Example 1.

The PCR amplification cycles were 94° C. for 30 seconds, 51° C. for 30 seconds, and 72° C. for 30 seconds. Generally, the samples were cycled 20 or 25 times. There was a final 5-minute extension at 72° C. before the samples were held at 4° C.

Similar experiments were carried out with primer specific to the T-cell receptor specific mRNA (TCR) which is expressed by the MOLT4 cell line.

Expected PCR Product Size (Base Pairs) Using the G3PDH Primers.

| REV PRIMER | FORWARD PRIMER G3PDH3 | FORWARD PRIMER dMTA1 |
| --- | --- | --- |
| G3PDH5-2 | 18 | 62 |
| G3PDH5-3 | 110 | 156 |
| G3PDH5-4 | 157 | 203 |
| G3PDH5 | 253 | 299 |
| G3PDH5-6 | 309 | 354 |
| G3PDH5-7 | 361 | 405 |

Primer Sequences (SEQ ID NO: 4)
G3PDH5: 5' TTT CCT GGT ATG ACA ACG AA (SEQ ID NO: 5)
G3PDH5-4: 5' CCA GCA AGA GCA CAA GAG GA (SEQ ID NO: 6)
G3PDH3: 5' GAT GGT ACA TGA CAA GGT (SEQ ID NO: 7)
dMTA1: 5' GAC GGA TGC GGT CTT TTT TTT Expected PCR Product Size (Base Pairs) Using T-Cell Receptor Primers

|  | TCR3 | DMTA1 |
| --- | --- | --- |
| TCR5-2 | 160 | Approx. 440 |
| TCR5 | 238 | Approx. 500 |

Primer Sequences (SEQ ID NO: 8)
TCR5: 5' CCC GCA ACC ACT TCC GCT GTC (SEQ ID NO: 9)
TCR5-2: 5' CAA ACC CGT CAC CCA GAT CGT (SEQ ID NO: 10)
TCR3: 5' CAA CAC AAG GGC GCT GAC C The results show that the unique sequence is incorporated into the second strand cDNA, as indicated by the presence of a product that was about 250 base pairs in length when the step 2 reaction mix was PCR amplified using primers DMTA1 and G3PDH5 (amplification of a sequence of G3PDH mRNA), and a product of about 400 base pairs in length when using primers DMTA1 and TCR5-2 (amplification of a sequence of TCR beta chain mRNA). PCR amplification of the step 3 reaction mix with the same primer pairs, on the other hand, showed a greatly reduced amount of amplification products. Thus, the results demonstrated the incorporation of the "unique" sequence (of the RNA portion of the composite primer used in Example 1) into the double stranded cDNA products generated, and the absence of the sequence in the final amplified DNA products (due to cleavage of the RNA portion).

Example 3

Amplification of Total mRNA Starting with a Total RNA Preparation

The ability to amplify total mRNA from a preparation of total RNA greatly simplifies the process by eliminating the mRNA purification step. Experimental demonstration of amplifying total mRNA from a total RNA preparation using methods of the invention was carried out using commercial total RNA preparation from breast cancer tumor (CLONTECH; cat. no.: 64015-1). The process of amplification of total mRNA was carried out in three steps as described in the following.

Primer Sequence:

(SEQ ID NO: 11)
MTB2: *GAC GGA UGC GGU C*UTTTTTTTTTTTTTNN (SEQ ID NO: 12)
BA5: AAC TAC CTT CAA CTC CAT CA (SEQ ID NO: 13)
BA3. GGA CTC GTC ATA CTC CTG C wherein italicized nucleotides denote ribonucleotides and "N" denotes a degenerate nucleotide (i.e., it can be A, T, C or G).

Step 1: First Strand cDNA Synthesis

Each reaction mixture comprised the following:
4 µl of a 5× buffer (250 mM Tris-HCl, pH 8.3; 375 mM KCl, 15 mM MgCl2)
MTB2 primer @1 µM
25 mM dNTPs
0.2 µl RNasin Ribonuclease Inhibitor (Promega N2511, 40 u/µl)
1 µl 0.1 M DTT
5 µg, 1 µg, 0.2 µg or 40 ng of total RNA per reaction
DEPC-treated water to a total volume of 19 µl The reaction mixtures were incubated at 75° C. for 2 minutes, and then cooled down to 42° C. SuperScript II RNase Reverse Transcriptase (200 U, BRL 18064-022) was added to each reaction, and the reactions were incubated at 42° C. for 50 minutes.

Step 2: Synthesis of Second Strand cDNA

10 µl of the first strand cDNA synthesis reaction mixture was aliquoted to individual reaction tubes. 20 µl of second strand synthesis stock reaction mixture was added to each tube. The second strand synthesis stock reaction mixture contained the following:

2 µl of 10× Klenow reaction buffer (10× buffer: 500 mM Tris-HCl, pH 8.0; 100 mM MgCl$_2$, 500 mM NaCl)
2 U Klenow DNA polymerase (BRL 18012-021)
0.1 µl of AMV reverse transcriptase (BRL 18020-016, 25 U/µl)
0.2 µl of *E coli* Ribonuclease H (BRL 18021-014, 4 U/µl)
0.2 µl (25 mM) dNTPs
0 or 0.2 µl of Ecoli DNA ligase (BRL 18052-019, 10 U/µl)

The reaction mixtures were incubated at 37° C. for 30 minutes. The reactions were stopped by heating to 75° C. for 5 minutes to inactivate the enzymes.

Step 3: Amplification of Total cDNA

Amplification was carried out using 1 pl of the second strand cDNA reaction mixture above, using the MTA1 composite primer in the presence of T4 gene 32 protein at 50° C. for 60 min.

Each reaction mixture contained the following:
2 µl of 10× buffer (200 mM Tris-HCl, pH 8.5, 50 mM MgCl$_2$, 1% NP-40)
0.2 µl of dNTPs (25 mM)
0.2 µl of MTA1 (100 µM)
1 µl of the second strand cDNA synthesis mixture
0.1 µl Rnasin
0.1 µl DTT (0.1M)
DEPC-treated water to a total volume of 18.8 µl The reaction mixtures were incubated at 94° C. for 20 seconds, and then cooled down to 50° C. 2 U Bca (Takara Cat.#2710A), 0.02 U Hybridase Thermostable Rnase H (Epicentre H39100), and 0.4 µg T4 Gene 32 Protein (USB 70029Z) were added, and the reactions were further incubated at this temperature for 60 min.

The step 3 reaction mix (expected to contain amplified DNA products) was analyzed by gel electrophoresis (5-20% PAGE, Novex). Successful amplification was indicated by the amplification products of the total mRNA appearing as a smear, which was expected due to amplification of a plurality of mRNA species in the sample.

The incorporation of a "unique" (defined) sequence (complementary to the 5'-end RNA portion of the composite primer used) into the second strand cDNA was demonstrated by PCR amplification using specific primer pairs. Aliquots of the step 2 and step 3 reaction mixes were subjected to PCR amplification using primers G3PDH5-4/G3PDH3 or BA5/BA3 (beta actin), using conditions as described in Example 2. PCR amplification of step 2 reaction mixes resulted in substantial amounts of products of the correct size, whereas amplification of step 3 reaction mixes resulted in substantial smaller amounts of the same products. Thus, the results demonstrated the incorporation of the "unique" sequence (of the RNA portion of the composite primer used in this Example) into the double stranded cDNA products, and the absence of the sequence in the final amplified DNA products (due to cleavage of the RNA portion).

Example 4

Preparation of Double Stranded cDNA Comprising an Appended Defined Sequence in the Second Strand cDNA from Total RNA Preparation and Purified mRNA Total RNA (1 ug) prepared from the HCT116 cell line, or mRNA (100 ng) prepared from MOLT4 cell line (Clontech) was used as a target for production of the intermediate double stranded cDNA product comprising an appended defined sequence in the second strand cDNA. The appended sequence is incorporated through utilization of a composite (first) primer.

The process of preparing the first and second strand cDNA was carried out essentially as described in Example 1 and 3, and generally included the following steps: (1) synthesis of first cDNA strand; (2) synthesis of second cDNA strand to produce a double stranded cDNA comprising at one end an RNA/DNA heteroduplex which is a substrate for Rliase H. Double stranded cDNA intermediate products are expected to comprise cDNA copies of multiple RNA from the target RNA sample, each cDNA with the same appended defined sequence. The sequence of the appended defined sequence is expected to be the complement of the sequence of the 5' RNA portion of the composite (first) primer that hybridizes to target RNA.

PCR experiments were performed to confirm the presence of second strand cDNA comprising (a) second strand cDNA copy of a sequence of the GAPDH mRNA known to be represented in the mRNA of both RNA target samples and (b) the defined sequence (i.e., the complement of the 5' RNA portion of the first composite primer) at the 3' end. The PCR primer pairs used were as follows:

1) A primer complementary to the unique sequence (DMTA1) and a primer complementary to the sequence of the GAPDH mRNA (GAPDH5-4) for generation of a 203 bp product that is dependent on appending of the sequence at the 3' end of the second cDNA strand.

2) Two primers complementary to the sequence of the GAPDH mRNA, GAPDH3 and primer GAPDH5-4, used for generation of a 157 bp product specific for GAPDH and is independent of appending the unique sequence at the 3' end of the second cDNA strand.

Figure 9:
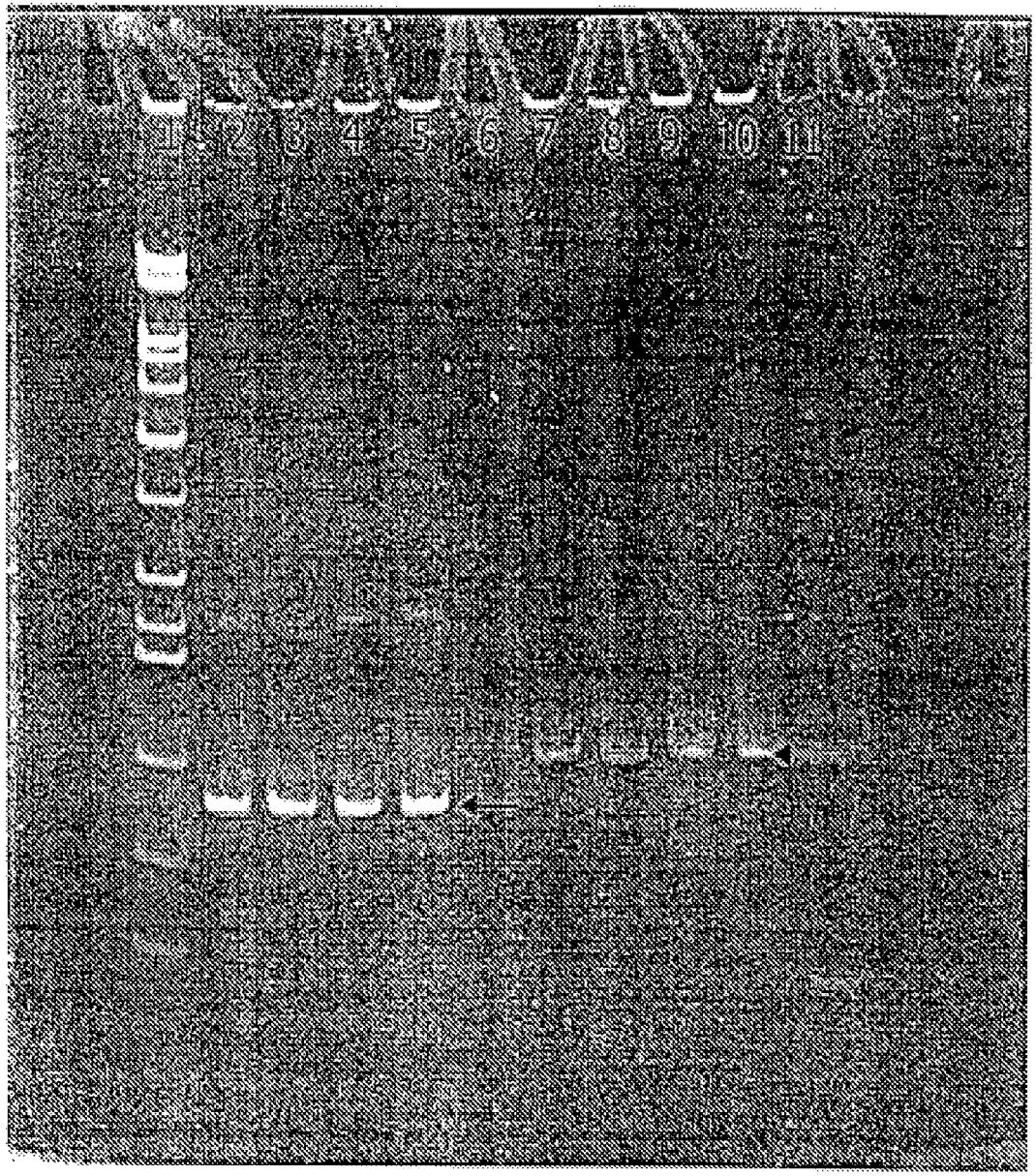
FIG. 9 shows a photograph of a gel showing PCR products amplified from double stranded cDNA comprising an appended defined sequence on the second strand cDNA prepared using linear isothermal RNA amplification.

PCR was performed as described in Examples 1 and 2 using two separate preparation of cDNA from each starting template, as described above. PCR reactions were analyzed using gel electrophoresis. The results are shown in FIG. 9. Lanes correspond to the reaction mixtures containing the following templates and primer pairs:

| 1.  | marker         |                  |
|-----|----------------|------------------|
| 2.  | cDNA from HCT116 | GAPDH3/GAPDH5-4 |
| 3.  | cDNA from HCT116 | GAPDH3/GAPDH5-4 |
| 4.  | cDNA from MOLT4  | GAPDH3/GAPDH5-4 |
| 5.  | cDNA from MOLT4  | GAPDH3/GAPDH5-4 |
| 6.  | no template     | GAPDH3/GAPDH5-4 |
| 7.  | cDNA from HCT116 | dMTA1/GAPDH5-4  |
| 8.  | cDNA from HCT116 | dMTA1/GAPDH5-4  |
| 9.  | cDNA from MOLT4  | dMTA1/GAPDH5-4  |
| 10. | cDNA from MOLT4  | dMTA1/GAPDH5-4  |
| 11. | no template     | dMTA1/GAPDH5-4  |

Arrows mark the position of expected per product.

As expected, a longer product was produced in HCT116 and MOLT4 samples amplified using primer pair (1), and a sorter product was generated in HCT116 and MOLT4 samples amplified using primer pair (2). No product was produced in control samples lacking template. This example demonstrates efficient appending of a defined sequence at the 3' end of the second cDNA using the methods described herein.

Example 5

Amplification of Total polyA mRNA and Quantification of Products Using Real Time PCR 200 ng of total RNA from Human Colon Tumor Total RNA, (Clontech Catalog No. 64014-1), was used as a target for amplification. The preparation of first and second strand cDNA and subsequent amplification step was carried out essentially as described in Example 3 with the following modifications:

(1) The reaction mixture for second strand cDNA synthesis contained Klenow DNA polymerase (which lacks 3' and 5' exonuclease activities), and lacked ligase.

(2) Amplification of the resultant cDNA was carried out using Bst polymerase (4 units, NEB) instead of Bca polymerase Quantification was determined for the cDNA intermediates (second strand cDNA) and the antisense amplification products using four different primer pairs corresponding to four different mRNAs, and Real Time PCR according to the following protocol:

cDNA or amplification products were diluted 1:10 or 1:100 in TE buffer.

Reaction mixtures for Real Time PCR were set to a total volume of 20 ul, as follows:

For each reaction

10 µl of 2×ABI SYBR Green master mix (ABI Cat #4309155)

0.6 µl of 10 µM forward primer 0.6 µl of 10 µM reverse primer

1 µl template (dilution of either cDNA or amplification products specified above)

7.8 µl of H$_2$O

The following primer pairs were used for quantification of four specific expressed genes in either cDNA or amplification products generated as described above:

```
G6PD
                                          (SEQ ID NO: 14)
G6PD5 5' AGGCAGCCTCTCTGCTATAAGAAA 3'

(SEQ ID NO: 15)
G6PD3 5' GCAGGGCATTGAGGTTGG 3'

LGALS1
                                          (SEQ ID NO: 16)
LGALS15 5' ATGGCAGCTGACGGTGACTT 3'

(SEQ ID NO: 17)
LGALS13 5' CATGGGCTGGCTGATTT 3'

MT2A
                                          (SEQ ID NO: 18)
MT2A5 5' CGCCTGATGCTGGGACAG 3'

(SEQ ID NO: 19)
MT2A3 5' GTTGTACATAAAAAATCCAGGTTTGTG 3'

RPL27
                                          (SEQ ID NO: 20)
RPL275 5' GATCCTGCTCTTAAACGCAAGG 3'

(SEQ ID NO: 21)
RPL273 5' TGCCTGTCTTGTATCTCTCTTCAAAC 3'
```

PCR reaction were performed in an iCycler (BioRad), using the following thermocycling protocol:

94° C. for 10 min to activate the DNA polymerase 40 cycles of: 94° C. for 30 seconds followed by 60° C. for 30 seconds.

Data analysis was carried out as recommended by the manufacturer.

Figure 10:
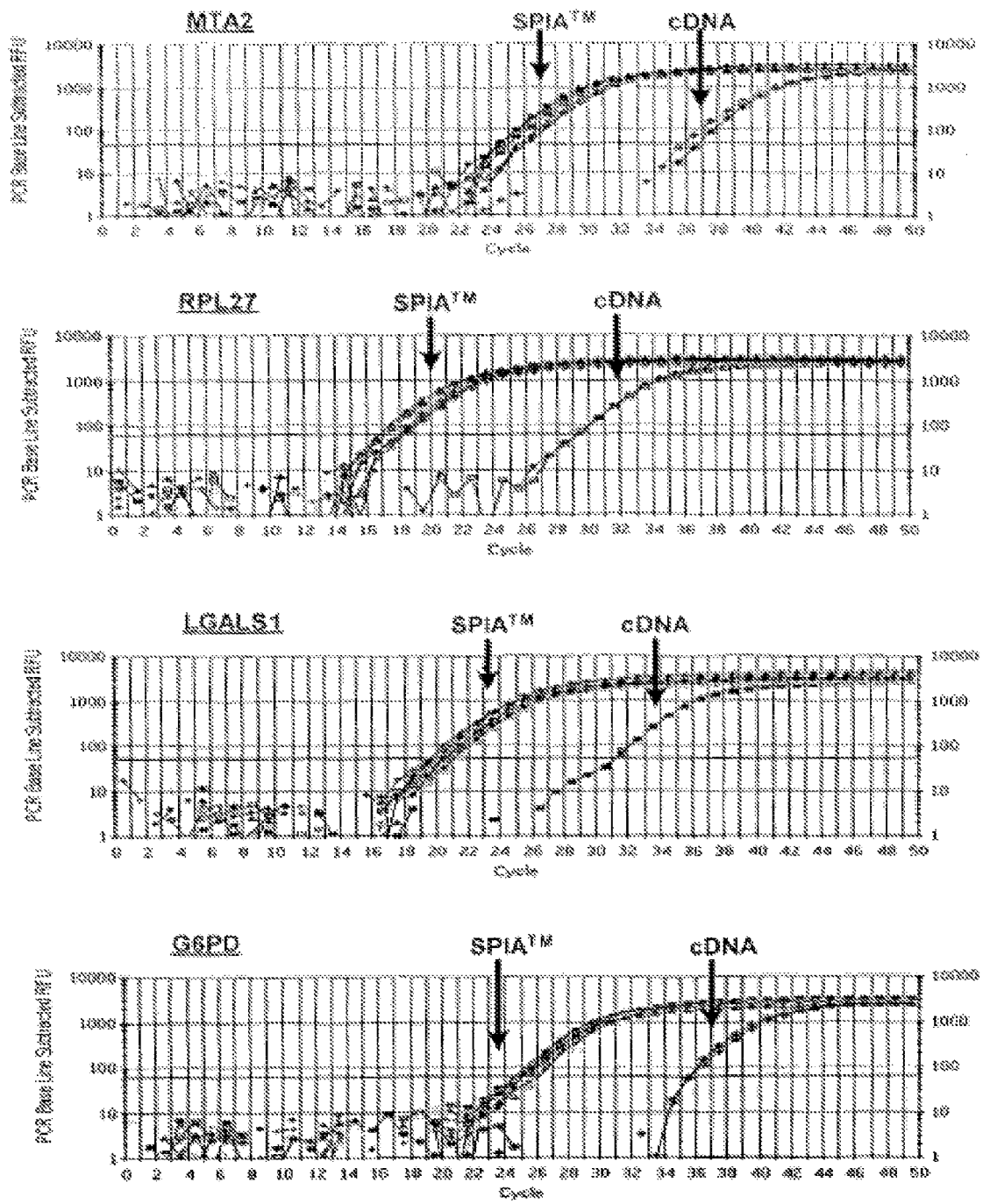
FIG. 10 shows graphs depicting results of real-time PCR experiments quantifying products generated using linear isothermal RNA amplification.

FIG. 10 show 4 traces of fluorescence reading as a function of cycle number for PCR reaction quantifying cDNA product (by amplifying the second strand cDNA) or the corresponding SPIA amplification products (by amplifying accumulated second strand cDNA). The panels depict the results of quantification experiments performed using (from top to bottom): MTA2, RPL27, LGALS1, and G6PD primer pairs, respectively. Each panel shows the results of 6 experiments using amplification product preparation (labeled "SPIA") and 2 experiments using cDNA product preparation (labeled "cDNA"). The X axis is PCR cycles and the Y axis is PCR baseline subtracted RFU.

The level of amplification of each of the gene products using the method of the invention is defined by the different number of PCR cycles required for generation of fluorescence signal (termed "CT") above a defined threshold, between reaction carried out using cDNA product template and reactions carried out using the corresponding amplification products as template. Table 1 shows a calculation of a "delta CT" value for each gene product (reflecting the comparison between CT values corresponding to reactions carried out using cDNA product template and reactions carried out using the corresponding amplification products as template), and which revealed that regardless of their expression level in the input total RNA, mRNAs corresponding to the four gene products in the sample are equally amplified by the method of the invention.

TABLE 1

Calculation of delta CT value for each gene product

| Gene | cDNA CT | SPIA CT | delta CT |
|------|---------|---------|----------|
| MT2A | 37 | 26 | 11 |
| RPL27 | 30 | 19 | 11 |
| LGAL | 31 | 21 | 10 |
| G6PD | 35 | 26 | 9 |

Although the foregoing invention has been described in some detail by way of illustration and example for purposes of clarity of understanding, it will be apparent to those skilled in the art that certain changes and modifications may be practiced. Therefore, the descriptions and examples should not be construed as limiting the scope of the invention, which is delineated by the appended claims.

What is claimed is:

1. A composition comprising at least one RNA template and a plurality of primers, wherein the primers are composite primers that comprise a 5' RNA portion and a 3' DNA portion, wherein the 3' DNA portion comprises a random sequence, and wherein the random sequence in at least one of the plurality of primers is complementary to a sequence in the at least one RNA template.

2. The composition of claim 1, further comprising an RNA-dependent DNA polymerase.

3. The composition of claim 1, further comprising a DNA-dependent DNA polymerase.

4. The composition of claim 1, further comprising an enzyme that cleaves RNA from an RNA/DNA hybrid.

5. The composition of 4, wherein the enzyme is RNaseH.

6. The composition of claim 1, further comprising a labeled dNTP.

7. The composition of claim 6, wherein the labeled dNTP consists of a label selected from a group consisting of fluorescent dyes, radioisotopes, enzymes, steroids, colorimetric labels, ligands, and anti-ligands.

8. The composition of claim 1, wherein the RNA portion of the primers consists of about 10 to about 20 nucleotides and the DNA portion of the primers consists of about 5 to about 20 nucleotides.

9. The composition of claim 1, wherein the 5' RNA portion of the primers is adjacent to the 3' DNA portion.

10. The composition of claim 1, wherein the primers are tailed primers that comprise a 5' portion that is not hybridizable to the at least one RNA template under conditions in which the primers hybridize to the at least one RNA template.

11. The composition of claim 1, wherein the random sequence of the 3'DNA portion of the primers comprises at least 1 random nucleotide at the 3' end.

12. The composition of claim 1, wherein the at least one RNA template is selected from a group consisting of total RNA, tRNA, mRNA, rRNA, mitochondrial RNA, chloroplast RNA, DNA-RNA hybrids, viral RNA, cell free RNA, and mixtures thereof.

13. The composition of claim 1, wherein the 5' RNA portion comprises a defined sequence.

14. The composition of claim 1, wherein the plurality of primers comprises a first pool of composite primers, and a second pool of composite primers, wherein the first pool of composite primers comprises a mixture of composite primers which comprise the same 5' RNA portion and a multiplicity of random sequences in the 3' DNA portion, and wherein the second pool of composite primers comprises a mixture of composite primers which comprise the same 5' RNA portion and a multiplicity of random sequences in the 3' DNA portion, wherein the 5' RNA portion and 3' DNA portion of the first pool of composite primers is different from the second pool of composite primers.

15. The composition of claim 1, further comprising an additional composite primer comprising a 5' RNA portion and a 3' DNA portion, wherein the 3' DNA portion of the composite primer comprises a poly-dT sequence.

\* \* \* \* \*